United States Patent
Bacque et al.

(10) Patent No.: US 8,846,670 B2
(45) Date of Patent: Sep. 30, 2014

(54) 1,2,3,4-TETRAHYDRO-PYRIMIDO(1,2-A)PYRIMIDIN-6-ONE DERIVATIVES, PREPARATION THEREOF, AND PHARMACEUTICAL USE THEREOF

(75) Inventors: Eric Bacque, Paris (FR); Maurice Brollo, Paris (FR); Annie Clauss, Paris (FR); Youssef El Ahmad, Paris (FR); Bruno Filoche-Romme, Paris (FR); Frank Halley, Paris (FR); Karl Andreas Karlsson, Paris (FR); Gilbert Marciniak, Paris (FR); Baptiste Ronan, Paris (FR); Laurent Schio, Paris (FR); Bertrand Vivet, Paris (FR); Fabrice Viviani, Paris (FR); Andre Zimmermann, Paris (FR)

(73) Assignee: Sanofi, Paris (FR)

( * ) Notice: Subject to any disclaimer, the term of this patent is extended or adjusted under 35 U.S.C. 154(b) by 334 days.

(21) Appl. No.: 13/381,790

(22) PCT Filed: Jul. 1, 2010

(86) PCT No.: PCT/FR2010/051374
§ 371 (c)(1),
(2), (4) Date: Apr. 20, 2012

(87) PCT Pub. No.: WO2011/001113
PCT Pub. Date: Jan. 6, 2011

(65) Prior Publication Data
US 2012/0208810 A1  Aug. 16, 2012

Related U.S. Application Data

(60) Provisional application No. 61/241,098, filed on Sep. 10, 2009.

(30) Foreign Application Priority Data

Jul. 2, 2009  (FR) ................................. 09 03237
Oct. 9, 2009  (FR) ................................. 09 57069

(51) Int. Cl.
*A61K 31/5377* (2006.01)
*A61K 31/519* (2006.01)
*C07D 413/14* (2006.01)
*C07D 487/04* (2006.01)
*C07D 239/06* (2006.01)
*C07D 239/42* (2006.01)

(52) U.S. Cl.
CPC .......... *C07D 487/04* (2013.01); *A61K 31/5377* (2013.01); *A61K 31/519* (2013.01); *C07D 413/14* (2013.01); *C07D 239/06* (2013.01); *C07D 239/42* (2013.01)

USPC ........................................ 514/233.2; 544/117

(58) Field of Classification Search
CPC ............... C07D 413/14; C07D 487/04; A61K 31/5377; A61K 31/519
USPC ........................................ 544/117; 514/233.2
See application file for complete search history.

(56) References Cited

FOREIGN PATENT DOCUMENTS

| FR | 2 378 792 A1 | 8/1978 |
|----|---|---|
| WO | WO02/18386 A1 | 3/2002 |
| WO | WO03/027116 A2 | 4/2003 |
| WO | WO03/072579 A1 | 9/2003 |
| WO | WO2006/109081 A1 | 10/2006 |
| WO | WO2008/148074 A2 | 12/2008 |

OTHER PUBLICATIONS

Cancer and Metastasis Reviews (1998), 17(1), 91-106.*
Science (1999), vol. 286, 531-537.*
International Search Report dated Jan. 5, 2011 issued in PCT/FR2010/051374.
Wee, Susan, et. al., "PTEN-deficient cancers depend on PIK3CB", PNAS, vol. 105, No. 35, pp. 13057-13062, Sep. 2, 2008.

* cited by examiner

*Primary Examiner* — Rebecca Anderson
(74) *Attorney, Agent, or Firm* — Scully, Scott, Murphy & Presser, P.C.

(57) ABSTRACT

The invention relates to compounds of the formula:

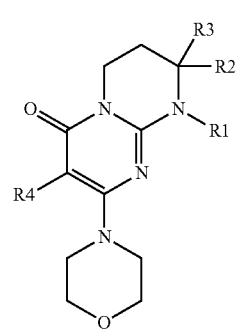

(I)

or their racemic, enantiomeric or diastereoisomeric isomers, or pharmaceutically acceptable salts of the compounds of formula I or the racemic, enantiomeric or diastereoisomeric isomers.

17 Claims, No Drawings

1,2,3,4-TETRAHYDRO-PYRIMIDO(1,2-A)PYRIMIDIN-6-ONE DERIVATIVES, PREPARATION THEREOF, AND PHARMACEUTICAL USE THEREOF

CROSS-REFERENCE TO RELATED APPLICATIONS

This application claims the benefit of U.S. Provisional Application No. 61/241,098 filed on Sep. 10, 2009.

The present invention relates to novel chemical compounds (1,2,3,4-tetrahydropyrimido{1,2-a}pyrimidin-6-one), derived from pyrimidinones, to the process for the preparation thereof, to the novel intermediates obtained, to the use thereof as medicaments, to the pharmaceutical compositions containing them and to the novel use of such derivatives.

The present invention thus also relates to the use of said derivatives for the preparation of a medicament for use in treating humans.

More particularly, the invention relates to novel pyrimidinone derivatives and to the pharmaceutical use thereof for the prevention and treatment of conditions capable of being modulated by inhibition of the PI3K/AKT/mTOR pathway. AKT is a key participant in this signalling pathway. A high level of AKT phosphorylation is the marker of the activation of the pathway, which is found in many human cancers.

The products of the present invention may thus in particular be used for the prevention or treatment of conditions capable of being modulated by inhibition of AKT phosphorylation (P-AKT). The inhibition of P-AKT may especially be obtained by inhibition of the PI3K/AKT/mTOR pathway, and in particular by inhibition of kinases belonging to this pathway, for instance receptor tyrosine kinases such as EGFR, IGFR, ErbB2,3'-phosphoinositide-dependent protein kinase-1 (PDK1), the PI3K phosphoinositide kinase, the AKT serine-threonine kinase, or the mTOR kinase.

The inhibition and regulation of the PI3K/AKT/mTOR pathway constitutes in particular a new and powerful mechanism of action for the treatment of a large number of cancer diseases including solid and liquid tumours.

Such conditions that can be treated by the products of the present application are solid or liquid human tumours.

This invention also relates to novel pyrimidinone derivatives and to the pharmaceutical use thereof for the prevention and treatment of conditions affected by the modulation of autophagy. The inhibition and regulation of autophagy constitutes a new mechanism of action for the treatment of a large number of cancer diseases, including solid and liquid tumours.

This invention also relates to novel pyrimidinone derivatives and to the pharmaceutical use thereof for the treatment of parasitic diseases such as malaria, sleeping sickness, Chagas disease or leishmaniasis.

Role of the PI3K/AKT/mTOR Pathway

The PI3K/AKT/mTOR signalling pathway is a complex network which regulates multiple cell functions, such as growth, survival, proliferation and cell motility, which are key processes in tumorigenesis.

This signalling pathway is an important target in the treatment of cancer since most of its effectors are altered in human tumours. The principal effectors contribute to the activation of the pathway are i) oncogenes, such as ErbB1 (EGFR), ErbB2 (HER2), PIK3CA and AKT, activated by mutation, amplification or overexpression; ii) a deficiency in tumour suppressor genes such as PTEN, TSC½, LKB and PML, which are inactivated following mutations or deletions (Jiang L-Z & Liu L-Z, Biochim Biophys Acta, 2008, 1784:150; Vivanco I & Sawyers C L, 2002, Nat Rev Cancer, 2:489; Cully M et al., Nature Rev. Cancer, 2006, 6:184).

The activation of the oncogenes of this signalling pathway is found in many human cancer diseases:

PIK3CA activating mutations are present in 15-30% of colon, breast, endometrial, liver, ovarian and prostate cancers (TL Yuan and L C Cantley, Oncogene, 2008, 27:5497; Y. Samuels et al. Science, 2004, 304:554; K E. Bachman et al. Cancer Biol Ther, 2004, 3:772; Acta Neuropathol. 2005, 109:639);

amplifications, activating mutations and overexpressions of RTKs such as EGFR and HER2 in brain, breast and lung (NSCLC) cancers;

amplification and activating overexpression of AKT in brain, lung (NSCLC), breast, kidney, ovarian and pancreatic cancers (Testa J R. and Bellacosa A., Proct. Natl. Acad. Sci. USA 2001, 98:10983; Cheng et al., Proct. Natl. Acad. Sci. USA 1992, 89: 9267; Bellacosa et al., Int. J. Cancer, 1995, 64:280; Cheng et al., Proct. Natl. Acad. Sci. USA 1996, 93:3636; Yuan et al., Oncogene, 2000, 19:2324).

Deficiency in the tumour suppressor genes of this signalling pathway is also found in many human cancer diseases:

deletion of PTEN in 50% of lung (NSCLC), liver, kidney, prostate, breast, brain, pancreatic, endometrial and colon cancers (Maxwell G L et al. Canc. Res. 1998, 58:2500; Zhou X-P et al. Amer. J. Pathol., 2002, 161: 439; Endersby R & Baker S J, Oncogene, 2008, 27:5416; Li et al. Science, 1997, 275:1943; Steack P A et al., Nat. Genet., 1997, 15:356);

mutations in TSC½ in more than 50% of tuberous scleroses;

mutations or deletions in LKB1 (or STK11) which predispose to gastrointestinal tract cancers and to pancreatic cancer and which are found in particular in 10-38% of lung adenocarcinomas (Shah U. et al. Cancer Res. 2008, 68:3562);

modifications of PML in particular by translocation in human tumours (Gurrieri C et al, J. NAtl Cancer Inst. 2004, 96:269).

In addition, this signalling pathway is a major factor for resistance to chemotherapy, to radiotherapy and to targeted therapies such as EGFR and HER2 inhibitors, for example (C. Sawyers et al. Nat Rev 2002).

Role of AKT

AKT (protein kinase B; PKB) is a serine-threonine kinase which occupies a central place in one of the major cell signalling pathways, the PI3K/AKT pathway. AKT is in particular involved in the growth, proliferation and survival of tumour cells. AKT activation occurs in two steps, (1) by phosphorylation of threonine 308 (P-T308) by PDK1 and (2) by phosphorylation of serine 473 (P-S473) by mTORC2 (or mTOR-Rictor complex), resulting in complete activation. AKT in turn regulates a large number of proteins, including mTOR (mammalian target of Rapamycin), BAD, GSK3, p21, p27, FOXO or FKHRL1 (Manning B D & Cantley L C, Cell, 2007 129:1261). The activation of AKT promotes the internalisation of nutrients, thereby triggering a process of anabolising metabolisation supporting cell growth and proliferation. In particular, AKT controls the initiation of protein synthesis through a cascade of interactions that occurs by means of TSC½ (tuberous sclerosis complex), Rheb and TOR, so as to result in two essential targets of the signalling pathway, p70S6K and 4EBP. AKT also induces inhibiting phosphorylation of the Forkhead transcription factor and inactivation of GSK3β, which result in the inhibition of apoptosis and in progression of the cell cycle (Franke T F, Oncogene, 2008, 27:6473). AKT is therefore a target for anticancer therapy and the inhibition of AKT activation by inhibition of the phosphorylation thereof may induce apoptosis of malignant cells and, by the same token, provide a treatment for cancer.

Receptor Tyrosine Kinases Such as IGF1R

Abnormally high levels of protein kinase activity have been implicated in many diseases resulting from abnormal cell functions. This may originate either directly or indirectly from a dysfunction in the mechanisms for controlling the kinase activity, related to for example an inappropriate mutation, overexpression or activation of the enzyme, or owing to an overproduction or underproduction of cytokines or of growth factors, also involved in the transduction of upstream or downstream signals of kinases. In all these cases, a selective inhibition of the action of kinases leads to the hope of a beneficial effect.

The insulin-like growth factor type 1 receptor (IGF-I-R) is a transmembrane receptor tyrosine kinase which binds firstly to IGFI, but also to IGFII and to insulin with a weaker affinity. The binding of IGF1 to its receptor leads to oligomerization of the receptor, activation of the tyrosine kinase, intermolecular autophosphorylation and phosphorylation of cell substrates (principal substrates: IRS1 and Shc). The receptor activated by its ligand induces a mitogenic activity in normal cells. However, IGF-I-R plays an important role in "abnormal" growth.

Several clinical reports underline the important role of the IGF-I pathway in the development of human cancers:

IGF-I-R is often found overexpressed in many tumour types (breast, colon, lung, sarcoma, prostate, multiple myeloma) and its presence is often associated with a more aggressive phenotype.

High concentrations of circulating IGF1 are strongly correlated with a risk of prostate, lung and breast cancer.

Furthermore, it has been widely documented that IGF-I-R is necessary for the establishment and maintenance of the transformed phenotype in vitro just as in vivo [Baserga R, Exp. Cell. Res., 1999, 253, pages 1-6]. The kinase activity of IGF-I-R is essential for the transforming activity of several oncogenes: EGFR, PDGFR, SV40 virus broad T antigen, activated Ras, Raf, and v-Src. The expression of IGF-I-R in normal fibroblasts induces a neoplastic phenotype, which can subsequently lead to tumour formation in vivo. IGF-I-R expression plays an important role in substrate-independent growth. IGF-I-R has also been shown to be a protector in chemotherapy- and radiation-induced apoptosis and cytokine-induced apoptosis. Furthermore, the inhibition of endogenous IGF-I-R by a dominant negative, the formation of a triple helix or the expression of an antisense causes a suppression of the transforming activity in vitro and a decrease in tumour growth in animal models.

PDK1

3'-Phosphoinositide-dependent protein kinase-1 (PDK1) is one of the essential components of the PI3K-AKT signalling pathway. It is a serine-threonine (Ser/Thr) kinase, the role of which is to phosphorylate and activate other Ser/Thr kinases of the AGC family that are involved in the control of cell growth, proliferation and survival and in the regulation of the metabolism. These kinases include protein kinase B (PKB or AKT), SGK (or serum and glucocorticoid regulated kinase), RSK (or p90 ribosomal S6 kinase), p70S6K (or p70 ribosomal S6 kinase) and also various isoforms of protein kinase C (PKC) (Vanhaesebroeck B. & Alessi D R., Biochem J, 2000, 346:561). One of the key roles of PDK1 is therefore the activation of AKT: in the presence of PIP3, which is the second messenger generated by PI3K, PDK-1 is recruited to the plasma membrane via its PH (pleckstrin homology) domain and phosphorylates AKT on threonine 308 located in the activation loop, which is an essential modification for AKT activation. PDK1 is expressed ubiquitously and is a constitutively active kinase. PDK1 is a key element in the PI3K/AKT signalling pathway for regulating key processes in tumorigenesis, such as cell proliferation and survival. Since this pathway is activated in more than 50% of human cancers, PDK1 represents a target for anticancer therapy. The inhibition of PDK1 should result in an effective inhibition of the proliferation and survival of cancer cells and therefore provide a therapeutic benefit for human cancers (Bayascas J R, Cell cycle, 2008, 7:2978; Peifer C. & Alessi D R, ChemMedChem, 2008, 3:1810).

Phosphoinositide 3-Kinases (PI3Ks)

The PI3K lipid kinase is an important target in this signalling pathway for oncology. The class I PI3Ks are divided up into class Ia (PI3Kα,β,δ) activated by receptor tyrosine kinases (RTKs), G protein-coupled receptors (GPCRs), GTPases of the family Rho and p21-Ras, and class Ib (PI3Kγ) activated by GPCRs and p21-Ras. The class Ia PI3Ks are heterodimers which consist of a catalytic subunit p110α, β or δ and a regulatory subunit p85 or p55. The class Ib (p110γ) is monomeric. The class I PI3Ks are lipid/protein kinases which are activated by RTKs, GPCRs or Ras after recruitment of the membrane. These class I PI3Ks phosphorylate phosphatidylinositol 4,5-diphosphate (PIP2) on position 3 of the inositol so as to give phosphatidylinositol 3,4,5-triphosphate (PIP3), a key secondary messenger in this signalling pathway. In turn, PIP3 recruits AKT and PDK1 to the membrane, where they bind via their pleckstrin homology domain (PH domain), resulting in activation of AKT by PDK1 phosphorylation on threonine 308. AKT phosphorylates many substrates, thus playing a key role in many processes resulting in cell transformation, such as cell proliferation, growth and survival, and also angiogenesis.

The class I PI3Ks are implicated in human cancers: somatic mutations of the PIK3CA gene, which encodes PI3Kα, are found in 15-35% of human tumours, with in particular two principal oncogenic mutations, H1047R (in the kinase domain), and E545K/E542K (in the helical domain), (Y. Samuels et al. Science, 2004, 304:554; T L Yuan and L C Cantley, Oncogene, 2008, 27:5497). PI3K inhibitors are expected to be effective in the treatment of many human cancers exhibiting genetic alterations resulting in the activation of the PI3K/AKT/mTOR pathway (Vogt P. et al., Virology, 2006, 344:131; Zhao L & Vogt P K, Oncogene, 2008, 27:5486).

mTOR mTOR (mammalian target of rapamycin) is a serine-threonine kinase related to the lipid kinases of the PI3K family. mTOR has been implicated in various biological processes, including cell growth, proliferation, motility and survival. mTOR is a multifunctional kinase which integrates both the signals coming from growth factors and those coming from nutrients in order to regulate protein translation, nutrient uptake, autophagy and mitochondrial function. mTOR exists in the form of two different complexes, called mTORC1 and mTORC2. mTORC1 contains the raptor subunit and mTORC2 contains the rictor subunit. These two complexes are regulated differently: mTORC1 phosphorylates the S6 kinase (S6K) and 4EBP1, thus stimulating translation and ribosome biogenesis so as to facilitate cell growth and progression in the cell cycle. S6K also acts in a feedback pathway for reducing the activation of AKT. mTORC1 is sensitive to rapamycin, whereas mTORC2 is generally insensitive to rapamycin. mTORC2 appears to modulate growth factor signalling by phosphorylating AKT on serine residue 473. mTOR has been implicated in various pathological conditions, including in particular cancer, diabetes, obesity, cardiovascular diseases and neurological disorders. mTOR modulates many biological processes, including translation, autophagy and ribosome biogenesis by integrating intracellular and extracellular signals such as the signals transported by growth factors, nutrients, energy levels and cell stress (Guertin D. A. and Sabatini D., Cancer Cell, 2007, 12: 9; Menon S, and Manning B. D., Oncogene, 2009, 27:S43).

The Role of Autophagy

Autophagy is a lysosome-dependent intracellular degradation mechanism (organelles, long-lived proteins, etc.). The autophagy process involves the formation of particular vesicles called autophagosomes. The class III PI3K lipid kinase (Vps34) is involved in the formation of autophagosomes. This class III PI3K phosphorylates phosphatidylinositol (PI) on position 3 of the inositol so as to give phosphatidylinositol-3-triphosphate (PI3P). PI3P is a key second messenger in autophagosome formation via the recruitment of proteins such as WIPI, DFCP1 and Alfy. Autophagy is a cell survival mechanism which enables the cell to survive in a situation of stress, for instance in the face of a metabolic stress. In the case of cancer, autophagy is implicated in the resistance of tumour cells in the face of environmental stresses such as: hypoxia, oxidative stresses, nutrient deficiency, but also in the face of therapeutic stresses: treatments with anticancer agents, ionizing radiation.

Application in Antimalarial Chemotherapy

Malaria is one of the primary infectious causes of mortality in the world and, each year, affects 100 to 200 million individuals. The strong resurgence of the disease observed over the last few years is due to several factors, including:

the vectors, namely anopheles mosquitoes, which become resistant to the conventional cheap insecticides, the increase in the population in the areas at risk, and, mainly, the resistance of numerous strains of *Plasmodium falciparum*, which is a parasite responsible for the lethal forms of the disease, to the conventional medicaments used, such as chloroquine and mefloquine.

The propagation of the resistance among the strains of *Plasmodium*, in particular *P. falciparum*, to most of the antimalarial medicaments demonstrates the urgent need to develop new compounds having a new mode of action and thus enabling a decrease in the risk of cross resistance. Human kinases are targets that have been validated in the treatment of many pathological conditions, and the kinome of *P. falciparum* has been proposed as a reservoir of new targets for the development of new medicaments which have not yet been explored in the treatment of malaria.

The *Plasmodium falciparum* kinome is composed of 64 kinases, some of which are orthologues of human kinases. Kinase signalling pathway inhibitors have been tested for their ability to inhibit, in vitro and in vivo, the growth of *P. falciparum* and of other pathogenic species responsible for malaria.

The molecules of the invention inhibit the growth of *P. falciparum* (highly chloroquine-resistant strain Fcm29-Cameroon) at 1 µM and 0.1 µM in an in vitro test using infected human erythrocytes, as indicated in Table 2.

Similar kinomes are present in all the *Plasmodium* species, such as *P. falciparum, P. vivax, P. malariae, P. ovale* and *P. knowlesi*. The compounds of the invention can therefore be used in the treatment of malaria induced by all the parasites mentioned above. In addition, the kinases are found in other parasites, such as *Trypanosoma* (for example, *T. brucei, T. cruzei*) and *Leishmania* (for example, *L. major, L. donovani*). The compounds of the invention can therefore be used in the treatment of sleeping sickness, Chagas disease, the various forms of leishmaniasis and other parasitic infections.

Kinase-inhibiting morpholino-pyrimidinone derivatives are known to those skilled in the art.

Application WO 2008/148074 describes produces which have an mTOR-inhibiting activity. These products are pyrido[1,2-a]pyrimidin-4-ones which differ from the products of the present invention owing to their entirely aromatic nature and their substitutions.

Application WO 2008/064244 describes the application of the PI3Kβ-inhibiting products TGX-221 and TGX-155 that are of use in the treatment of cancer, and in particular of breast cancer. These products are pyrido[1,2-a]pyrimidin-4-ones previously described in applications WO 2004/016607 and WO 2001/053266, which differ from the products of the present invention owing to their entirely aromatic nature and their substitutions.

Applications WO 2006/109081, WO 2006/109084 and WO 2006/126010 describe DNA-PK-inhibiting products that are of use in the treatment of ATM-deficient cancers. These products are pyrido[1,2-a]pyrimidin-4-ones which differ from the products of the present invention owing to their entirely aromatic nature and their substitutions.

Application WO 2003/024949 describes DNA-PK-inhibiting products that are of use in the treatment of ATM-deficient cancers. These products are pyrido[1,2-a]pyrimidin-4-ones which differ from the products of the present invention owing to their entirely aromatic nature and their substitutions.

The subject of the present invention is the products of formula (I):

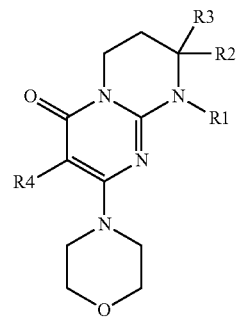

in which:
R1 represents an -L-aryl or -L-heteroaryl radical, such that L represents:
either a single bond,
or a linear or branched alkyl radical containing from 1 to 6 carbon atoms and optionally substituted with a hydroxyl radical,
or a CO or —CO-Alk- group,
or an L'-X group where L' represents a linear or branched alkyl radical containing from 1 to 6 carbon atoms, and X an oxygen or sulphur atom;
the aryl and heteroaryl radicals being optionally substituted with one or more radicals, which may be identical or different, chosen from halogen atoms and hydroxyl, CN, nitro, —COON, —COOalk, —NRxRy, —CONRxRy, —NRxCORy, —NRxCO$_2$Rz, —CORy, alkoxy, phenoxy, alkylthio, alkyl, cycloalkyl and heterocycloalkyl radicals;
the latter alkoxy, phenoxy, alkylthio, alkyl and heterocycloalkyl radicals being themselves optionally substituted with one or more radicals, which may be identical or different, chosen from halogen atoms and NRvRw;

it being possible for the heterocycloalkyl and heteroaryl radicals to additionally contain an oxo radical;

R2 represents a hydrogen atom or an alkyl radical;

R3 represents an alkyl radical optionally substituted with one or more halogen atoms;

R4 represents a hydrogen atom or a halogen atom;

NRxRy being such that Rx represents a hydrogen atom or an alkyl radical and Ry represents a hydrogen atom or a cycloalkyl radical or an alkyl radical optionally substituted with one or more radicals, which may be identical or different, chosen from hydroxyl, alkoxy, NRvRw and heterocycloalkyl radicals; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;

NRvRw being such that Rv represents a hydrogen atom or an alkyl radical and Rw represents a hydrogen atom or a cycloalkyl radical or an alkyl radical optionally substituted with one or more radicals, which may be identical or different, chosen from hydroxyl, alkoxy and heterocycloalkyl radicals; or Rv and Rw form, with the nitrogen atom to which they are attached, a cyclic radical containing from 3 to 10 ring members and optionally one or more other heteroatoms chosen from O, S, NH and N-alkyl, this cyclic radical being optionally substituted;

the cyclic radicals that Rx and Ry or Rv and Rw, respectively, can form with the nitrogen atom to which they are attached, being optionally substituted with one or more radicals, which may be identical or different, chosen from halogen atoms, and alkyl, hydroxyl, oxo, alkoxy, $NH_2$, NHalk and $N(alk)_2$ radicals;

Rz represents the values of Ry except for hydrogen;

Rx, Ry and Rz, in the —NRxCORy, —CORy and $NRxCO_2Rz$ radicals, being chosen from the meanings indicated above for Rx, Ry and Rz;

said products of formula (I) being in all the possible racemic, enantiomeric and diastereoisomeric isomer forms, and also the addition salts with inorganic and organic acids or with inorganic and organic bases, of said products of formula (I).

A subject of the present invention is thus the products of formula (I) as defined above, in which:

R1 represents an -L-aryl or -L-heteroaryl radical, such that L represents:

either a single bond, or a linear or branched alkyl radical containing from 1 to 6 carbon atoms and optionally substituted with a hydroxyl radical, or a CO group, or an L'-X group where L' represents a linear or branched alkyl radical containing from 1 to 6 carbon atoms, and X an oxygen or sulphur atom;

the aryl and heteroaryl radicals being optionally substituted with one or more radicals, which may be identical or different, chosen from halogen atoms and hydroxyl, CN, nitro, —COOH, —COOalk, —NRxRy, —CONRxRy, —NRxCORy, —NRxCO₂Rz, —CORy, alkoxy, phenoxy, alkylthio, alkyl, cycloalkyl and heterocycloalkyl radicals;

the latter alkoxy, phenoxy, alkylthio, alkyl and heterocycloalkyl radicals being themselves optionally substituted with one or more radicals, which may be identical or different, chosen from halogen atoms and NRvRw;

it being possible for the heterocycloalkyl and heteroaryl radicals to also contain an oxo radical;

R2 represents a hydrogen atom or an alkyl radical;

R3 represents an alkyl radical optionally substituted with one or more halogen atoms;

R4 represents a hydrogen atom or a halogen atom;

NRxRy being such that Rx represents a hydrogen atom or an alkyl radical and Ry represents a hydrogen atom or a cycloalkyl radical or an alkyl radical optionally substituted with one or more radicals, which may be identical or different, chosen from hydroxy, alkoxy, NRvRw or heterocycloalkyl radicals; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;

NRvRw being such that Rv represents a hydrogen atom or an alkyl radical and Rw represents a hydrogen atom or a cycloalkyl radical or an alkyl radical optionally substituted with one or more radicals, which may be identical or different, chosen from hydroxyl, alkoxy and heterocycloalkyl radicals; or Rv and Rw form, with the nitrogen atom to which they are attached, a cyclic radical containing from 3 to 10 ring members and optionally one or more other heteroatoms chosen from O, S, NH and N-alkyl, this cyclic radical being optionally substituted;

the cyclic radicals that Rx and Ry or Rv and Rw, respectively, can form with the nitrogen atom to which they are attached, being optionally substituted with one or more radicals, which may be identical or different, chosen from halogen atoms, and alkyl, hydroxyl, oxo, alkoxy, $NH_2$, NHalk and $N(alk)_2$ radicals;

Rz represents the values of Ry except for hydrogen;

Rx, Ry and Rz in the —NRxCORy, —CORy and $NRxCO_2Rz$ radicals being chosen from the meanings indicated above for Rx, Ry and Rz;

said products of formula (I) being in all the possible racemic, enantiomeric and diastereoisomeric isomer forms, and also the addition salts with inorganic and organic acids or with inorganic and organic bases, of said products of formula (I).

In the products of formula (I):

the term "alkyl (or alk) radical" denotes the linear, and where appropriate branched, radicals methyl, ethyl, propyl, isopropyl, butyl, isobutyl, sec-butyl, tert-butyl, pentyl, isopentyl, hexyl, isohexyl and also heptyl, octyl, nonyl and decyl, and also the linear or branched positional isomers thereof: the alkyl radicals containing from 1 to 6 carbon atoms and more particularly the alkyl radicals containing from 1 to 4 carbon atoms of the above list are preferred;

the term "alkoxy radical" denotes the linear, and where appropriate branched, radicals methoxy, ethoxy, propoxy, isopropoxy, linear, secondary or tertiary butoxy, pentoxy or hexoxy, and also the linear or branched positional isomers thereof: the alkoxy radicals containing from 1 to 4 carbon atoms of the above list are preferred;

the term "alkylthio radical" denotes the linear, and where appropriate branched, radicals methylthio, ethylthio, propylthio, isopropylthio, linear, secondary or tertiary butylthio, pentylthio or hexylthio, and also the linear or branched positional isomers thereof: the alkylthio radicals containing from 1 to 4 carbon atoms of the above list are preferred;

the term "halogen atom" denotes chlorine, bromine, iodine or fluorine atoms, and preferably the chlorine, bromine or fluorine atom;

the term "cycloalkyl radical" denotes a saturated carbocyclic radical containing 3 to 10 carbon atoms and thus denotes in particular cyclopropyl, cyclobutyl, cyclopentyl and cyclohexyl radicals, and most particularly cyclopropyl, cyclopentyl and cyclohexyl radicals;

in the —O-cycloalkyl radical, cycloalkyl is as defined above;

the term "heterocycloalkyl radical" thus denotes a monocyclic or bicyclic carbocyclic radical containing from 3 to 10 ring members, interrupted with one or more heteroatoms, which may be identical or different, chosen from oxygen, nitrogen or sulphur atoms: mention may, for example, be made of morpholinyl, thiomorpholinyl, homomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, tetrahydropyran, oxodihydropyridazinyl or else oxetanyl radicals, all these radicals being optionally substituted; mention may in particular be made of morpholinyl, thiomorpholinyl, homomorpholinyl, piperazinyl, piperidyl, homopiperazinyl or else pyrrolidinyl radicals;

the terms "aryl" and "heteroaryl" denote monocyclic or bicyclic, respectively carbocyclic and heterocyclic, unsaturated or partially unsaturated radicals containing at most 12 ring members, that may optionally contain a —C(O) ring member, the heterocyclic radicals containing one or more heteroatoms, which may be identical or different, chosen from O, N, or S, with N, where appropriate, being optionally substituted;

the term "aryl radical" thus denotes monocyclic or bicyclic radicals containing 6 to 12 ring members, such as, for example, phenyl, naphthyl, biphenyl, indenyl, fluorenyl and anthracenyl radicals, more particularly phenyl and naphthyl radicals, and even more particularly the phenyl radical. It may be noted that a carbocyclic radical containing a —C(O) ring member is, for example, the tetralone radical;

the term "heteroaryl radical" thus denotes monocyclic or bicyclic radicals containing 5 to 12 ring members: monocyclic heteroaryl radicals such as, for example, the radicals: thienyl, such as 2-thienyl and 3-thienyl, furyl, such as 2-furyl or 3-furyl, pyranyl, pyrrolyl, pyrrolinyl, pyrazolinyl, imidazolyl, pyrazolyl, pyridyl, such as 2-pyridyl, 3-pyridyl and 4-pyridyl, pyrazinyl, pyrimidinyl, pyridazinyl, oxazolyl, thiazolyl, isothiazolyl, diazolyl, thiadiazolyl, thiatriazolyl, oxadiazolyl, isoxazolyl, such as 3- or 4-isoxazolyl, furazanyl, free or salified tetrazolyl, all these radicals being optionally substituted, among which are more particularly the radicals: thienyl, such as 2-thienyl and 3-thienyl, furyl, such as 2-furyl, pyrrolyl, pyrrolinyl, pyrazolinyl, imidazolyl, pyrazolyl, oxazolyl, isoxazolyl, pyridyl and pyridazinyl, these radicals being optionally substituted; bicyclic heteroaryl radicals such as, for example, the radicals: benzothienyl, such as 3-benzothienyl, benzothiazolyl, quinolyl, isoquinolyl, dihydroquinolyl, quinolone, tetralone, adamentyl, benzofuryl, isobenzofuryl, dihydrobenzofuran, ethylenedioxyphenyl, thianthrenyl, benzopyrrolyl, benzimidazolyl, benzoxazolyl, thionaphthyl, indolyl, azaindolyl, indazolyl, purinyl, thienopyrazolyl, tetrahydroindazolyl, tetrahydrocyclopentapyrazolyl, dihydrofuropyrazolyl, tetrahydropyrrolopyrazolyl, oxotetrahydropyrrolo-pyrazolyl, tetrahydropyranopyrazolyl, tetrahydropyridinopyrazolyl or oxodihydropyridinopyrazolyl, all these radicals being optionally substituted.

As examples of heteroaryl or bicyclic radicals, mention may more particularly be made of pyrimidinyl, pyridyl, pyrrolyl, azaindolyl, indazolyl or pyrazolyl, benzothiazolyl or benzimidazolyl radicals optionally substituted with one or more substituents, which may be identical or different, as indicated above.

The carboxyl radical(s) of the products of formula (I) may be salified or esterified with the various groups known to those skilled in the art, among which mention may be made, for example of:

among the salification compounds, inorganic bases such as, for example, an equivalent of sodium, of potassium, of lithium, of calcium, of magnesium or of ammonium, or organic bases such as, for example, methylamine, propylamine, trimethylamine, diethylamine, triethylamine, N,N-dimethylethanolamine, tris (hydroxymethyl)aminomethane, ethanolamine, pyridine, picoline, dicyclohexylamine, morpholine, benzylamine, procaine, lysine, arginine, histidine and N-methylglucamine;

among the esterification compounds, the alkyl radicals for forming alkoxycarbonyl groups, such as, for example, methoxycarbonyl, ethoxycarbonyl, tert-butoxycarbonyl or benzyloxycarbonyl, it being possible for these alkyl radicals to be substituted with radicals chosen, for example, from halogen atoms and hydroxyl, alkoxy, acyl, acyloxy, alkylthio, amino or aryl radicals, as, for example, in chloromethyl, hydroxypropyl, methoxymethyl, propionyloxymethyl, methylthiomethyl, dimethylaminoethyl, benzyl or phenethyl groups.

The addition salts with inorganic or organic acids of the products of formula (I) may, for example, be the salts formed with hydrochloric acid, hydrobromic acid, hydroiodic acid, nitric acid, sulphuric acid, phosphoric acid, propionic acid, acetic acid, trifluoroaectic acid, formic acid, benzoic acid, maleic acid, fumaric acid, succinic acid, tartaric acid, citric acid, oxalic acid, glyoxylic acid, aspartic acid, ascorbic acid, alkoylmonosulphonic acids such as, for example, methanesulphonic acid, ethanesulphonic acid or propanesulphonic acid, alkoyldisulphonic acids such as, for example, methanedisulphonic acid or alpha, beta-ethanedisulphonic acid, arylmonosulphonic acids such as benzenesulphonic acid, and aryldisulphonic acids.

It may be recalled that stereoisomerism can be defined in its broad sense as the isomerism of compounds having the same structural formulae, but the various groups of which are arranged differently in space, such as in particular in monosubstituted cyclohexanes in which the substituent may be in the axial or equatorial position, and the various possible rotational conformations of ethane derivatives. However, another type of stereoisomerism exists, due to the different spatial arrangements of fixed substituents, on double bonds or on rings, which is often referred to as geometrical isomerism or cis-transisomerism. The term "stereoisomers" is used in the present application in its broadest sense and therefore relates to all the compounds indicated above.

A subject of the present invention is the products of formula (I) as defined above, in which:

R1 represents an -L-phenyl or -L-heteroaryl radical, such that L represents:

either a single bond, or a linear or branched alkyl radical containing from 1 to 6 carbon atoms and optionally substituted with a hydroxyl radical, or a CO or —CO-Alk- group, or an L'-X group where L' represents a linear or branched alkyl radical containing from 1 to 6 carbon atoms, and X an oxygen or sulphur atom;

the phenyl and heteroaryl radicals being optionally substituted with one or more radicals, which may be identical or different, chosen from halogen atoms and —NRxRy, alkoxy and alkyl radicals;

the latter alkoxy and alkyl radicals being themselves optionally substituted with one or more radicals chosen from halogen atoms;

R2 represents an alkyl radical;

R3 represents an alkyl radical optionally substituted with one or more halogen atoms;

R4 represents a hydrogen atom or a fluorine atom;

NRxRy being such that Rx represents a hydrogen atom or an alkyl radical and Ry represents a hydrogen atom or an alkyl radical; or Rx and Ry form, with the nitrogen atom to which they are attached, a morpholino radical;

all the above alkyl (alk) or alkoxy radicals being linear or branched and containing from 1 to 6 carbon atoms, said products of formula (I) being in all the possible racemic, enantiomeric and diastereoisomeric forms, and also the addition salts with inorganic and organic acids or with inorganic and organic bases, of said products of formula (I).

In particular, when NRxRy or NRvRw forms a ring as defined above, such an amine ring may be chosen in particular from pyrrolidinyl, pyrazolidinyl, pyrazolinyl, piperidyl, azepinyl, morpholinyl, homomorpholinyl, piperazinyl or homopiperazinyl radicals, these radicals being themselves optionally substituted as indicated above or hereinafter.

The NRxRy or NRvRw ring may more particularly be chosen from the radicals: pyrrolidinyl, morpholinyl optionally substituted with one or two alkyl radicals or piperazinyl optionally substituted on the second nitrogen atom with an alkyl, phenyl or and CH$_2$-phenyl radical, themselves optionally substituted with one or more radicals, which may be identical or different, chosen from halogen atoms and alkyl, hydroxyl and alkoxy radicals.

A subject of the present invention is most particularly the products of formula (I) as defined above, corresponding to the following formulae:

(8S)-9-[2-(4-methoxyphenyl)ethyl]-2-(morpholin-4-yl)-8-(trifluoromethyl)-6,7,8,9-tetrahydro-4H-pyrimido[1,2-a]pyrimidin-4-one 9-[2-(4-methoxyphenyl)ethyl]-2-(morpholin-4-yl)-8-(trifluoromethyl)-6,7,8,9-tetrahydro-4H-pyrimido[1,2-a]pyrimidin-4-one (8S)-2-(morpholin-4-yl)-9-(2-phenylethyl)-8-(trifluoromethyl)-6,7,8,9-tetrahydro-4H-pyrimido[1,2-a]pyrimidin-4-one (8S)-9-benzyl-2-(morpholin-4-yl)-8-(trifluoromethyl)-6,7,8,9-tetrahydro-4H-pyrimido[1,2-a]pyrimidin-4-one (8S)-9-[(2S)-2-hydroxy-2-phenylethyl]-2-(morpholin-4-yl)-8-(trifluoromethyl)-6,7,8,9-tetrahydro-4H-pyrimido[1,2-a]pyrimidin-4-one (8S)-9-[(2R)-2-hydroxy-2-phenylethyl]-2-(morpholin-4-yl)-8-(trifluoromethyl)-6,7,8,9-tetrahydro-4H-pyrimido[1,2-a]pyrimidin-4-one (8S)-9-[(2S)-2-hydroxy-2-(4-methoxyphenyl)ethyl]-2-(morpholin-4-yl)-8-(trifluoromethyl)-6,7,8,9-tetrahydro-4H-pyrimido[1,2-a]pyrimidin-4-one (8S)-2-(morpholin-4-yl)-9-[(1R)-1-phenylethyl]-8-(trifluoromethyl)-6,7,8,9-tetrahydro-4H-pyrimido[1,2-a]pyrimidin-4-one (8S)-9-[1-(4-methoxyphenyl)ethyl]-2-(morpholin-4-yl)-8-(trifluoromethyl)-6,7,8,9-tetrahydro-4H-pyrimido[1,2-a]pyrimidin-4-one (8S)-9-[(1S)-1-(4-bromophenyl)ethyl]-2-(morpholin-4-yl)-8-(trifluoromethyl)-6,7,8,9-tetrahydro-4H-pyrimido[1,2-a]pyrimidin-4-one (8S)-9-[(1R)-1-(4-bromophenyl)ethyl]-2-(morpholin-4-yl)-8-(trifluoromethyl)-6,7,8,9-tetrahydro-4H-pyrimido[1,2-a]pyrimidin-4-one (8S)-2-(morpholin-4-yl)-9-phenyl-8-(trifluoromethyl)-6,7,8,9-tetrahydro-4H-pyrimido[1,2-a]pyrimidin-4-one (8S)-9-(4-fluorophenyl)-2-(morpholin-4-yl)-8-(trifluoromethyl)-6,7,8,9-tetrahydro-4H-pyrimido[1,2-a]pyrimidin-4-one (8S)-9-(3-fluorophenyl)-2-(morpholin-4-yl)-8-(trifluoromethyl)-6,7,8,9-tetrahydro-4H-pyrimido[1,2-a]pyrimidin-4-one (8S)-9-(2-fluorophenyl)-2-(morpholin-4-yl)-8-(trifluoromethyl)-6,7,8,9-tetrahydro-4H-pyrimido[1,2-a]pyrimidin-4-one (8S)-9-[(1R)-1-(3-fluorophenyl)ethyl]-2-(morpholin-4-yl)-8-(trifluoromethyl)-6,7,8,9-tetrahydro-4H-pyrimido[1,2-a]pyrimidin-4-one (8S)-9-(4-fluorobenzyl)-2-(morpholin-4-yl)-8-(trifluoromethyl)-6,7,8,9-tetrahydro-4H-pyrimido[1,2-a]pyrimidin-4-one (8S)-2-(morpholin-4-yl)-9-(phenylcarbonyl)-8-(trifluoromethyl)-6,7,8,9-tetrahydro-4H-pyrimido[1,2-a]pyrimidin-4-one (8S)-2-(morpholin-4-yl)-9-(pyridin-3-yl)-8-(trifluoromethyl)-6,7,8,9-tetrahydro-4H-pyrimido[1,2-a]pyrimidin-4-one (8S)-2-(morpholin-4-yl)-9-(pyridin-4-yl)-8-(trifluoromethyl)-6,7,8,9-tetrahydro-4H-pyrimido[1,2-a]pyrimidin-4-one (8S)-2-(morpholin-4-yl)-9-(pyridin-4-yl)-8-(trifluoromethyl)-6,7,8,9-tetrahydro-4H-pyrimido[1,2-a]pyrimidin-4-one (8S)-9-(4-methylphenyl)-2-(morpholin-4-yl)-8-(trifluoromethyl)-6,7,8,9-tetra-hydro-4H-pyrimido[1,2-a]pyrimidin-4-one (8S)-9-(2-chlorobenzyl)-2-(morpholin-4-yl)-8-(trifluoromethyl)-6,7,8,9-tetra-hydro-4H-pyrimido[1,2-a]pyrimidin-4-one (8S)-9-(3-fluorobenzyl)-2-(morpholin-4-yl)-8-(trifluoromethyl)-6,7,8,9-tetra-hydro-4H-pyrimido[1,2-a]pyrimidin-4-one (8S)-9-[2-(2-methoxyphenyl)ethyl]-2-(morpholin-4-yl)-8-(trifluoromethyl)-6,7,8,9-tetrahydro-4H-pyrimido[1,2-a]pyrimidin-4-one (8S)-9-[2-(3-methoxyphenyl)ethyl]-2-(morpholin-4-yl)-8-(trifluoromethyl)-6,7,8,9-tetrahydro-4H-pyrimido[1,2-a]pyrimidin-4-one (8S)-9-(3-methoxybenzyl)-2-(morpholin-4-yl)-8-(trifluoromethyl)-6,7,8,9-tetrahydro-4H-pyrimido[1,2-a]pyrimidin-4-one (8S)-9-(4-methoxyphenyl)-2-(morpholin-4-yl)-8-(trifluoromethyl)-6,7,8,9-tetrahydro-4H-pyrimido[1,2-a]pyrimidin-4-one (8S)-9-[(2-fluorophenyl)carbonyl]-2-(morpholin-4-yl)-8-(trifluoromethyl)-6,7,8,9-tetrahydro-4H-pyrimido[1,2-a]pyrimidin-4-one (8S)-9-(3,5-difluorobenzyl)-2-(morpholin-4-yl)-8-(trifluoromethyl)-6,7,8,9-tetrahydro-4H-pyrimido[1,2-a]pyrimidin-4-one (8S)-9-(2,4-difluorobenzyl)-2-(morpholin-4-yl)-8-(trifluoromethyl)-6,7,8,9-tetrahydro-4H-pyrimido[1,2-a]pyrimidin-4-one (8S)-2-(morpholin-4-yl)-9-(2,3,4-trifluorobenzyl)-8-(trifluoromethyl)-6,7,8,9-tetrahydro-4H-pyrimido[1,2-a]pyrimidin-4-one (8S)-9-[(5-chloro-1-benzothiophen-3-yl)methyl]-2-(morpholin-4-yl)-8-(trifluoromethyl)-6,7,8,9-tetrahydro-4H-pyrimido[1,2-a]pyrimidin-4-one (8S)-9-[(1R or 1S)-1-(4-fluorophenyl)ethyl]-2-(morpholin-4-yl)-8-(trifluoro-methyl)-6,7,8,9-tetrahydro-4H-pyrimido[1,2-a]pyrimidin-4-one (8S)-9-[(1R or 1S)-1-(4-fluorophenyl)ethyl]-2-(morpholin-4-yl)-8-(trifluoro-methyl)-6,7,8,9-tetrahydro-4H-pyrimido[1,2-a]pyrimidin-4-one (8S)-9-(3-methylphenyl)-2-(morpholin-4-yl)-8-(trifluoromethyl)-6,7,8,9-tetra-hydro-4H-pyrimido[1,2-a]pyrimidin-4-one (8S)-9-(4-chlorophenyl)-2-(morpholin-4-yl)-8-(trifluoromethyl)-6,7,8,9-tetra-hydro-4H-pyrimido[1,2-a]pyrimidin-4-one (8S)-2-(morpholin-4-yl)-8-(trifluoromethyl)-9-[4-(trifluoromethyl)phenyl]-6,7,8,9-tetrahydro-4H-pyrimido[1,2-a]pyrimidin-4-one (8S)-9-[(1R or 1S)-1-(2-fluorophenyl)ethyl]-2-(morpholin-4-yl)-8-(trifluoro-methyl)-6,7,8,9-tetrahydro-4H-pyrimido[1,2-a]pyrimidin-4-one (8S)-9-[(1R or 1S)-1-(2-fluorophenyl)ethyl]-2-(morpholin-4-yl)-8-(trifluoro-methyl)-6,7,8,9-tetrahydro-4H-pyrimido[1,2-a]pyrimidin-4-one (8S)-9-[2-(3-fluorophenyl)ethyl]-2-(morpholin-4-yl)-8-(trifluoromethyl)-6,7,8,9-tetrahydro-4H-pyrimido[1,2-a]pyrimidin-4-one (8S)-9-benzyl-3-fluoro-2-(morpholin-4-yl)-8-(trifluoromethyl)-6,7,8,9-tetra-hydro-4H-pyrimido[1,2-a]pyrimidin-4-one (8S)-9-(3,5-difluorophenyl)-2-(morpholin-4-yl)-8-(trifluoromethyl)-6,7,8,9-tetrahydro-4H-pyrimido[1,2-a]pyrimidin-4-one (8S)-9-[(2,6-difluorophenyl)carbonyl]-2-(morpholin-4-yl)-8-(trifluoromethyl)-6,7,8,9-tetrahydro-4H-pyrimido[1,2-a]pyrimidin-4-one (8S)-9-[(2,4-difluorophenyl)carbonyl]-2-(morpholin-4-yl)-8-(trifluoromethyl)-6,7,8,9-tetrahydro-4H-pyrimido[1,2-a]pyrimidin-4-one (8S)-2-(morpholin-4-yl)-9-(phenylacetyl)-8-(trifluoromethyl)-6,7,8,9-tetra-hydro-4H-pyrimido[1,2-a]pyrimidin-4-one (8S)-9-[2-(3-chlorophenyl)ethyl]-2-(morpholin-4-yl)-8-(trifluoromethyl)-6,7,8,9-tetrahydro-4H-pyrimido[1,2-a]pyrimidin-4-one 9-((R)-2-benzo[b]thiophen-2-yl-2-hydroxyethyl)-2-morpholin-4-yl-8-(S)-trifluoromethyl-6,7,8,9-tetrahydropyrimido[1,2-a]pyrimidin-4-one 9-[(S)-2-hydroxy-2-(3-hydroxyphenyl)ethyl]-2-morpholin-4-yl-8-(S)— trifluoromethyl-6,7,8,9-tetrahydropyrimido[1,2-a]pyrimidin-4-one 2-dimethylamino-N-{3-[(S)-1-hydroxy-2-((S)-8-morpholin-4-yl-6-oxo-2-trifluoromethyl-3,4-dihydro-2H,6H-pyrimido[1,2-a]pyrimidin-1-yl)ethyl]phenyl}acetamide 9-[(S)-2-hydroxy-2-(2-methoxyphenyl)ethyl]-2-morpholin-4-yl-8-(S)-trifluoromethyl-6,7,8,9-tetrahydropyrimido[1,2-a]pyrimidin-4-one 9-[(S)-2-(4-fluoro-2-methoxyphenyl)-2-hydroxyethyl]-2-morpholin-4-yl-8-(S)-trifluoromethyl-6,7,8,9-tetrahydropyrimido[1,2-a]pyrimidin-4-one 9-[(S)-2-(4-chloro-2-methoxyphenyl)-2-hydroxyethyl]-2-morpholin-4-yl-8-(S)-trifluoromethyl-6,7,8,9-tetrahydropyrimido[1,2-a]pyrimidin-4-one 9-[(S)-2-(2-chloro-4-methoxyphenyl)-2-hydroxyethyl]-2-morpholin-4-yl-8-(S)-trifluoromethyl-6,7,8,9-tetrahydropyrimido[1,2-a]pyrimidin-4-one 9-(2-hydroxy-3-phenylpropyl)-2-morpholin-4-yl-8-(S)-trifluoromethyl-6,7,8,9-tetrahydropyrimido[1,2-a]pyrimidin-4-one 9-[2-(4-hydroxyphenyl)ethyl]-2-morpholin-4-yl-8-(S)-trifluoromethyl-6,7,8,9-tetrahydropyrimido[1,2-a]pyrimidin-4-one and also the addition salts with inorganic and organic acids or with inorganic and organic bases, of said products of formula (I).

A subject of the present invention is also any process for preparing the products of formula (I) as defined above.

The products according to the invention can be prepared using conventional organic chemistry methods.

Preparation of Compounds of Formula (I)

General schemes 1 and 2 below illustrate the methods used for preparing the products of formula (I). In this respect, they cannot constitute a limitation of the scope of the invention, as regards the methods for preparing the claimed compounds.

The products of formula (I) as defined above according to the present invention may thus in particular be prepared according to the processes described in schemes 1 and 2.

A subject of the present invention is thus also the process for preparing products of formula (I) according to scheme 1 as defined hereinafter.

A subject of the present invention is thus also the process for preparing products of formula (I) according to general scheme 2 as defined hereinafter.

General scheme 1:

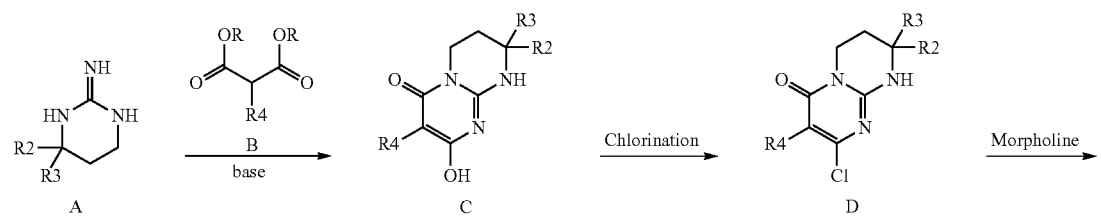

-continued

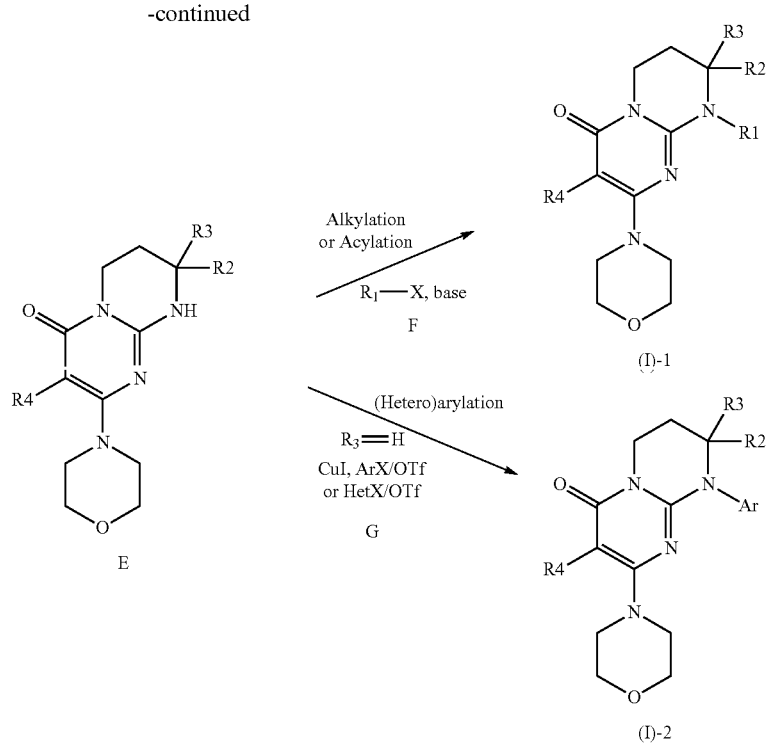

In general scheme 1:

The guanidines A are either commercially available or are prepared according to the processes described in Lochead, A. W. et al. (EP1460076 2002), Lochead, A. W. et al. (EP1340761 2003), Lochead, A. W. et al. (EP1454909 2004) and Lochead, A. W. et al. (WO2005058908 2005).

The compounds C can be obtained by condensation of a guanidine A with a dialkyl (preferably diethyl) malonate B, in the presence of a base such as sodium methoxide, at a temperature of between 60° C. and 100° C., according to the conditions described, for example, by Badawey E.-S. A. M. et al. (Eur J Med Chem, 1998, 33(5), 349-361).

The compounds D can be obtained from a compound C by treatment with a chlorinating agent such as phosphorus oxychloride, in the absence of solvent, at a temperature of between 20° C. and 120° C., or in the presence of a solvent such as dichloroethane, at a temperature of between 20° C. and the boiling point of the solvent, for instance under the conditions described by Yamashita, A. et al. (Syn. Commun. (2004), 34(5), 795-803).

The compounds E can be obtained from a compound D by reaction with morpholine, in the absence of solvent, at a temperature of between 20° C. and 120° C., or in the presence of a solvent such as acetonitrile, at a temperature of between 20° C. and the reflux temperature of the solvent, as described, for example, by Aliabiev S. B. (Lett. Org. Chem. (2007), 4(4), 273-280.

The compounds (I)-1 can be obtained by means of an alkylation or acylation reaction, by addition of a compound F (R1-X with R1=L-aryl or heteroaryl as defined above and X=Cl, Br, I or OTf in the case of an alkylation and X=Cl in the case of an acylation) to a mixture of a compound E and of a base such as sodium hydride or caesium carbonate in excess, in a solvent such as tetrahydrofuran, N,N-dimethylformamide or acetonitrile, at a temperature of between 0° C. and 80° C., as described, for example, by Ting P. C. et al. (J. Med. Chem. (1990), 33(10), 2697-2706) in the case of the alkylation reaction.

According to the procedure described by E. P. Seest et al., in Tet. Assymetry 17 (2006) 2154-2182, the compounds F corresponding to chiral 1-aryl-2-chloroethanols or 1-heteroaryl-2-chloroethanols were synthesized from the corresponding chloroketone derivatives, which are themselves derived from the chlorination, under standard conditions, of the commercially available acetyl derivatives.

The compounds (I)-2 can be obtained by reaction of a compound E with an aryl or heteroaryl halide (X=Cl, Br or I) or triflate G, in the presence of a coupling agent such as copper iodide, in the presence or absence of a copper ligand such as (+/-)-trans-1,2-diaminocyclohexane or 4,7-dimethoxy-1,10-phenanthroline, in the presence of a base such as potassium phosphate, in a solvent such as N-methylpyrrolidone or N,N-dimethylformamide, under microwave irradiation, at a temperature between 100° C. and 200° C., as described, for example, by Lianbo Z. et al. (J. Org. Chem. (2009), 74(5), 2200-2202).

Alternatively, the compounds (I)-1 can be obtained according to general scheme 2.

General scheme 2:

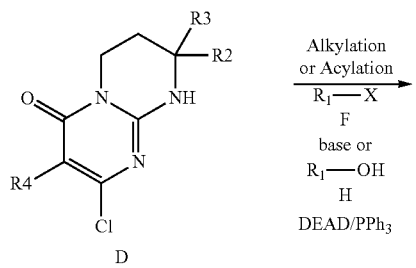

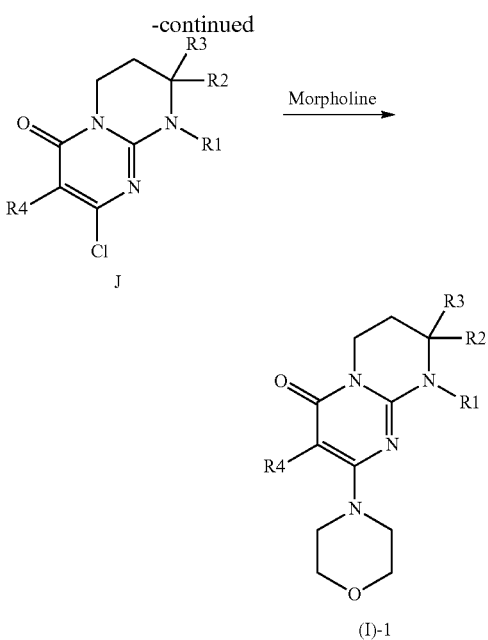

(I)-1

The compounds (I)-1 can be obtained from a compound J by reaction with morpholine, in the absence of solvent at a temperature of between 20° C. and 120° C., or in the presence of a solvent such as acetonitrile, at a temperature of between 20° C. and the reflux temperature of the solvent, as described, for example, by Aliabiev S. B. (Lett. Org. Chem. (2007), 4(4), 273-280.

The compounds J can be obtained by means of an alkylation or acylation reaction, by addition of a compound F (R1-X with R1=L-aryl or heteroaryl as defined above and X=Cl, Br, I or OTf in the case of an alkylation and X=Cl in the case of an acylation) to a mixture of a compound E and of a base such as sodium hydride or caesium carbonate in excess, in a solvent such as tetrahydrofuran, N,N-dimethylformamide or acetonitrile, at a temperature of between 0° C. and 80° C., as described, for example, by Ting P. C. et al. (J. Med. Chem. (1990), 33(10), 2697-2706) in the case of the alkylation reaction.

Alternatively, the compounds J can be obtained by means of a Mitsunobu reaction between a compound D and an alcohol H, in the presence of diethyl azodicarboxylate and of triphenylphosphine (optionally supported on a resin), in a solvent such as tetrahydrofuran, at a temperature of between 0° C. and 65° C., as described, for example, by O. Mitsunobu et al. (Synthesis (1981), 1-28).

When R2 is different from R3 and if the synthesis is not stereoselective, the enantiomers or the possible diastereoisomers of the synthesis intermediates or of the compounds (H) can be separated by chromatography on a chiral support.

The following examples of products of formula (I) illustrate the invention without, however, limiting it.

Among the starting products of formula A or B, some are known and can be obtained either commercially or according to the usual methods known to those skilled in the art, for example starting from commercially available products.

It is understood, for those skilled in the art, that, in order to implement the processes according to the invention, described above, it may be necessary to introduce protective groups for amino, carboxyl and alcohol functions in order to prevent side reactions.

The following non-exhaustive list of examples of protection of reactive functions may be mentioned:
hydroxyl groups can be protected, for example, with alkyl radicals such as tert-butyl, trimethylsilyl, tert-butyldimethylsilyl, methoxymethyl, tetrahydropyranyl, benzyl or acetyl,
amino groups can be protected, for example, with acetyl, trityl, benzyl, tert-butoxycarbonyl, BOC, benzyloxycarbonyl or phthalimido radicals or other radicals known in peptide chemistry.

Acid functions can be protected, for example, in the form of esters formed with readily cleavable esters such as benzyl or tert-butyl esters, or esters known in peptide chemistry.

A list of various protective groups that can be used will be found in the manuals known to those skilled in the art, and for example in patent BF 2 499 995.

It may be noted that it is possible, if desired and if necessary, to subject intermediate products or products of formula (I) thus obtained by means of the processes indicated above, in order to obtain other intermediates or other products of formula (I), to one or more conversion reactions known to those skilled in the art, such as, for example:

a) a reaction for esterification of an acid function,
b) a reaction for saponification of an ester function to give an acid function,
c) a reaction for reduction of the free or esterified carboxyl function to give an alcohol function,
d) a reaction for conversion of an alkoxy function to give a hydroxyl function, or else of a hydroxyl function to give an alkoxy function,
e) a reaction for removal of the protective groups that the protected reactive functions may be carrying,
f) a reaction for salification with an inorganic or organic acid or with a base so as to obtain the corresponding salt,
g) a reaction for resolving the racemic forms to give resolved products,
said products of formula (I) thus obtained being in all the possible racemic, enantiomeric and diastereoisomeric isomer forms.

The reactions a) to g) can be carried out under the usual conditions known to those skilled in the art, such as, for example, those indicated hereinafter.

a) The products described above may, if desired, be the subject, on the possible carboxyl functions, of esterification reactions which can be carried out according to the usual methods known to those skilled in the art.

b) The possible conversions of ester functions to give acid functions of the products described above may, if desired, be carried out under the usual conditions known to those skilled in the art, in particular by acid or alkaline hydrolysis, for example with sodium hydroxide or potassium hydroxide in an alcohol medium such as, for example, in methanol, or else with hydrochloric acid or sulphuric acid.

The saponification reaction can be carried out according to the usual methods known to those skilled in the art, such as, for example, in a solvent such as methanol or ethanol, dioxane or dimethoxyethane, in the presence of sodium hydroxide or of potassium hydroxide.

c) The possible free or esterified carboxyl functions of the products described above may, if desired, be reduced to give alcohol functions by means of the methods known to those skilled in the art: the possible esterified carboxyl functions may, if desired, be reduced to give alcohol functions by means of the methods known to those skilled in the art, and in particular with lithium aluminium hydride in a solvent such as, for example, tetrahydrofuran, or else dioxane or ethyl ether.

The possible free carboxyl functions of the products described above may, if desired, be reduced to give alcohol functions in particular with boron hydride.

d) The possible alkoxy functions, such as in particular methoxy functions, of the products described above may, if desired, be converted to hydroxyl functions under the usual conditions known to those skilled in the art, for example with boron tribromide in a solvent such as, for example, methylene chloride, with pyridine hydrobromide or hydrochloride or else with hydrobromic acid or hydrochloric acid in water or trifluoroacetic acid at reflux.

e) The removal of protective groups such as, for example, those indicated above can be carried out under the usual conditions known to those skilled in the art, in particular by acid hydrolysis carried out with an acid such as hydrochloric acid, benzenesulphonic acid, para-toluenesulphonic acid, formic acid or trifluoroacetic acid, or else by catalytic hydrogenation.

The phthalimido group may be removed with hydrazine.

f) The products described above may, if desired, be the subject of salification reactions, for example with an inorganic or organic acid or with an inorganic or organic base, according to the usual methods known to those skilled in the art: such a salification reaction can be carried out, for example, in the presence of hydrochloric acid, or else of tartaric acid, citric acid or methanesulphonic acid, in an alcohol such as, for example, ethanol or methanol.

g) The possible optically active forms of the products described above can be prepared by resolving the racemic mixtures according to the usual methods known to those skilled in the art.

The products of formula (I) as defined above, and also the addition salts thereof with acids, have advantageous pharmacological properties, in particular due to their kinase-inhibiting properties, as is indicated above.

The products of the present invention are in particular of use in tumour therapy.

The products of the invention may also thus increase the therapeutic effects of commonly used antitumour agents.

These properties justify the use thereof in therapy, and a subject of the invention is in particular, as medicaments, the products of formula (I) as defined above, said products of formula (I) being in all the possible racemic, enantiomeric and diastereoisomeric isomer forms, and also the pharmaceutically acceptable addition salts with inorganic and organic acids or with inorganic and organic bases, of said products of formula (I).

A subject of the invention is most particularly, as medicaments, the products corresponding to the following formulae:
- (8S)-9-[2-(4-methoxyphenyl)ethyl]-2-(morpholin-4-yl)-8-(trifluoromethyl)-6,7,8,9-tetrahydro-4H-pyrimido[1,2-a]pyrimidin-4-one
- 9-[2-(4-methoxyphenyl)ethyl]-2-(morpholin-4-yl)-8-(trifluoromethyl)-6,7,8,9-tetrahydro-4H-pyrimido[1,2-a]pyrimidin-4-one
- (8S)-2-(morpholin-4-yl)-9-(2-phenylethyl)-8-(trifluoromethyl)-6,7,8,9-tetrahydro-4H-pyrimido[1,2-a]pyrimidin-4-one
- (8S)-9-benzyl-2-(morpholin-4-yl)-8-(trifluoromethyl)-6,7,8,9-tetrahydro-4H-pyrimido[1,2-a]pyrimidin-4-one
- (8S)-9-[(2S)-2-hydroxy-2-phenylethyl]-2-(morpholin-4-yl)-8-(trifluoromethyl)-6,7,8,9-tetrahydro-4H-pyrimido[1,2-a]pyrimidin-4-one
- (8S)-9-[(2R)-2-hydroxy-2-phenylethyl]-2-(morpholin-4-yl)-8-(trifluoromethyl)-6,7,8,9-tetrahydro-4H-pyrimido[1,2-a]pyrimidin-4-one
- (8S)-9-[(2S)-2-hydroxy-2-(4-methoxyphenyl)ethyl]-2-(morpholin-4-yl)-8-(trifluoromethyl)-6,7,8,9-tetrahydro-4H-pyrimido[1,2-a]pyrimidin-4-one
- (8S)-2-(morpholin-4-yl)-9-[(1R)-1-phenylethyl]-8-(trifluoromethyl)-6,7,8,9-tetrahydro-4H-pyrimido[1,2-a]pyrimidin-4-one
- (8S)-9-[1-(4-methoxyphenyl)ethyl]-2-(morpholin-4-yl)-8-(trifluoromethyl)-6,7,8,9-tetrahydro-4H-pyrimido[1,2-a]pyrimidin-4-one
- (8S)-9-[(1S)-1-(4-bromophenyl)ethyl]-2-(morpholin-4-yl)-8-(trifluoromethyl)-6,7,8,9-tetrahydro-4H-pyrimido[1,2-a]pyrimidin-4-one
- (8S)-9-[(1R)-1-(4-bromophenyl)ethyl]-2-(morpholin-4-yl)-8-(trifluoromethyl)-6,7,8,9-tetrahydro-4H-pyrimido[1,2-a]pyrimidin-4-one
- (8S)-2-(morpholin-4-yl)-9-phenyl-8-(trifluoromethyl)-6,7,8,9-tetrahydro-4H-pyrimido[1,2-a]pyrimidin-4-one
- (8S)-9-(4-fluorophenyl)-2-(morpholin-4-yl)-8-(trifluoromethyl)-6,7,8,9-tetrahydro-4H-pyrimido[1,2-a]pyrimidin-4-one
- (8S)-9-(3-fluorophenyl)-2-(morpholin-4-yl)-8-(trifluoromethyl)-6,7,8,9-tetrahydro-4H-pyrimido[1,2-a]pyrimidin-4-one
- (8S)-9-(2-fluorophenyl)-2-(morpholin-4-yl)-8-(trifluoromethyl)-6,7,8,9-tetrahydro-4H-pyrimido[1,2-a]pyrimidin-4-one
- (8S)-9-[(1R)-1-(3-fluorophenyl)ethyl]-2-(morpholin-4-yl)-8-(trifluoromethyl)-6,7,8,9-tetrahydro-4H-pyrimido[1,2-a]pyrimidin-4-one
- (8S)-9-(4-fluorobenzyl)-2-(morpholin-4-yl)-8-(trifluoromethyl)-6,7,8,9-tetrahydro-4H-pyrimido[1,2-a]pyrimidin-4-one
- (8S)-2-(morpholin-4-yl)-9-(phenylcarbonyl)-8-(trifluoromethyl)-6,7,8,9-tetrahydro-4H-pyrimido[1,2-a]pyrimidin-4-one
- (8S)-2-(morpholin-4-yl)-9-(pyridin-3-yl)-8-(trifluoromethyl)-6,7,8,9-tetrahydro-4H-pyrimido[1,2-a]pyrimidin-4-one
- (8S)-2-(morpholin-4-yl)-9-(pyridin-4-yl)-8-(trifluoromethyl)-6,7,8,9-tetrahydro-4H-pyrimido[1,2-a]pyrimidin-4-one
- (8S)-9-(4-methylphenyl)-2-(morpholin-4-yl)-8-(trifluoromethyl)-6,7,8,9-tetrahydro-4H-pyrimido[1,2-a]pyrimidin-4-one
- (8S)-9-(2-chlorobenzyl)-2-(morpholin-4-yl)-8-(trifluoromethyl)-6,7,8,9-tetrahydro-4H-pyrimido[1,2-a]pyrimidin-4-one
- (8S)-9-(3-fluorobenzyl)-2-(morpholin-4-yl)-8-(trifluoromethyl)-6,7,8,9-tetrahydro-4H-pyrimido[1,2-a]pyrimidin-4-one
- (8S)-9-[2-(2-methoxyphenyl)ethyl]-2-(morpholin-4-yl)-8-(trifluoromethyl)-6,7,8,9-tetrahydro-4H-pyrimido[1,2-a]pyrimidin-4-one
- (8S)-9-[2-(3-methoxyphenyl)ethyl]-2-(morpholin-4-yl)-8-(trifluoromethyl)-6,7,8,9-tetrahydro-4H-pyrimido[1,2-a]pyrimidin-4-one
- (8S)-9-(3-methoxybenzyl)-2-(morpholin-4-yl)-8-(trifluoromethyl)-6,7,8,9-tetrahydro-4H-pyrimido[1,2-a]pyrimidin-4-one
- (8S)-9-(4-methoxyphenyl)-2-(morpholin-4-yl)-8-(trifluoromethyl)-6,7,8,9-tetrahydro-4H-pyrimido[1,2-a]pyrimidin-4-one
- (8S)-9-[(2-fluorophenyl)carbonyl]-2-(morpholin-4-yl)-8-(trifluoromethyl)-6,7,8,9-tetrahydro-4H-pyrimido[1,2-a]pyrimidin-4-one (8S)-9-(3,5-difluorobenzyl)-2-(morpholin-4-yl)-8-(trifluoromethyl)-6,7,8,9-tetrahydro-4H-pyrimido[1,2-a]pyrimidin-4-one (8S)-9-(2,4-difluorobenzyl)-2-(morpholin-4-yl)-8-(trifluoromethyl)-6,7,8,9-tetrahydro-4H-pyrimido[1,2-a]pyrimidin-4-one (8S)-2-(morpholin-4-yl)-9-(2,3,4-trifluorobenzyl)-8-(trifluoromethyl)-6,7,8,9-tetrahydro-4H-pyrimido[1,2-a]pyrimidin-4-one (8S)-9-[(5-chloro-1-benzothiophen-3-yl)methyl]-2-(morpholin-4-yl)-8-(trifluoromethyl)-6,7,8,9-tetrahydro-4H-pyrimido[1,2-a]pyrimidin-4-one (8S)-9-[(1R or 1S)-1-(4-fluorophenyl)ethyl]-2-(morpholin-4-yl)-8-(trifluoromethyl)-6,7,8,9-tetrahydro-4H-pyrinnido[1,2-a]pyrimidin-4-one (8S)-9-[(1R or 1S)-1-(4-fluorophenyl)ethyl]-2-(morpholin-4-yl)-8-(trifluoro-methyl)-6,7,8,9-tetrahydro-4H-pyrimido[1,2-a]pyrimidin-4-one (8S)-9-(3-methylphenyl)-2-(morpholin-4-yl)-8-(trifluoromethyl)-6,7,8,9-tetra-hydro-4H-pyrimido[1,2-a]pyrimidin-4-one (8S)-9-(4-chlorophenyl)-2-(morpholin-4-yl)-8-(trifluoromethyl)-6,7,8,9-tetra-hydro-4H-pyrimido[1,2-a]pyrimidin-4-one (8S)-2-(morpholin-4-yl)-8-(trifluoromethyl)-9-[4-(trifluoromethyl)phenyl]-6,7,8,9-tetrahydro-4H-pyrimido[1,2-a]pyrimidin-4-one (8S)-9-[(1R or 1S)-1-(2-fluorophenyl)ethyl]-2-(morpholin-4-yl)-8-(trifluoromethyl)-6,7,8,9-tetrahydro-4H-pyrimido[1,2-a]pyrimidin-4-one (8S)-9-[(1R or 1S)-1-(2-fluorophenyl)ethyl]-2-(morpholin-4-yl)-8-(trifluoromethyl)-6,7,8,9-tetrahydro-4H-pyrimido[1,2-a]pyrimidin-4-one (8S)-9-[2-(3-fluorophenyl)ethyl]-2-(morpholin-4-yl)-8-(trifluoromethyl)-6,7,8,9-tetrahydro-4H-pyrimido[1,2-a]pyrimidin-4-one (8S)-9-benzyl-3-fluoro-2-(morpholin-4-yl)-8-(trifluoromethyl)-6,7,8,9-tetra-hydro-4H-pyrimido[1,2-a]pyrimidin-4-one (8S)-9-(3,5-difluorophenyl)-2-(morpholin-4-yl)-8-(trifluoromethyl)-6,7,8,9-tetrahydro-4H-pyrimido[1,2-a]pyrimidin-4-one (8S)-9-[(2,6-difluorophenyl)carbonyl]-2-(morpholin-4-yl)-8-(trifluoromethyl)-6,7,8,9-tetrahydro-4H-pyrimido[1,2-a]pyrimidin-4-one (8S)-9-[(2,4-difluorophenyl)carbonyl]-2-(morpholin-4-yl)-8-(trifluoromethyl)-6,7,8,9-tetrahydro-4H-pyrimido[1,2-a]pyrimidin-4-one (8S)-2-(morpholin-4-yl)-9-(phenylacetyl)-8-(trifluoromethyl)-6,7,8,9-tetrahydro-4H-pyrimido[1,2-a]pyrimidin-4-one (8S)-9-[2-(3-chlorophenyl)ethyl]-2-(morpholin-4-yl)-8-(trifluoromethyl)-6,7,8,9-tetrahydro-4H-pyrimido[1,2-a]pyrimidin-4-one 9-((R)-2-benzo[b]thiophen-2-yl-2-hydroxyethyl)-2-morpholin-4-yl-8-(S)-trifluoromethyl-6,7,8,9-tetrahydropyrimido[1,2-a]pyrimidin-4-one 9-[(S)-2-hydroxy-2-(3-hydroxyphenyl)ethyl]-2-morpholin-4-yl-8-(S)-trifluoromethyl-6,7,8,9-tetrahydropyrimido[1,2-a]pyrimidin-4-one 2-dimethylamino-N-{3-[(S)-1-hydroxy-2-((S)-8-morpholin-4-yl-6-oxo-2-trifluoromethyl-3,4-dihydro-2H,6H-pyrimido[1,2-a]pyrimidin-1-yl)ethyl]phenyl}acetamide 9-[(S)-2-hydroxy-2-(2-methoxyphenyl)ethyl]-2-morpholin-4-yl-8-(S)-trifluoromethyl-6,7,8,9-tetrahydropyrimido[1,2-a]pyrimidin-4-one 9-[(S)-2-(4-fluoro-2-methoxyphenyl)-2-hydroxyethyl]-2-morpholin-4-yl-8-(S)-trifluoromethyl-6,7,8,9-tetrahydropyrimido[1,2-a]pyrimidin-4-one 9-[(S)-2-(4-chloro-2-methoxyphenyl)-2-hydroxyethyl]-2-morpholin-4-yl-8-(S)-trifluoromethyl-6,7,8,9-tetrahydropyrimido[1,2-a]pyrimidin-4-one 9-[(S)-2-(2-chloro-4-methoxyphenyl)-2-hydroxyethyl]-2-morpholin-4-yl-8-(S)-trifluoromethyl-6,7,8,9-tetrahydropyrimido[1,2-a]pyrimidin-4-one 9-(2-hydroxy-3-phenylpropyl)-2-morpholin-4-yl-8-(S)-trifluoromethyl-6,7,8,9-tetrahydropyrimido[1,2-a]pyrimidin-4-one 9-[2-(4-hydroxyphenyl)ethyl]-2-morpholin-4-yl-8-(S)-trifluoromethyl-6,7,8,9-tetrahydropyrimido[1,2-a]pyrimidin-4-one and also the pharmaceutically acceptable addition salts with inorganic and organic acids or with inorganic and organic bases, of said products of formula (I).

The invention also relates to pharmaceutical compositions containing, as active ingredient, at least one of the products of formula (I) as defined above or a pharmaceutically acceptable salt of this product or a prodrug of this product, and, where appropriate, a pharmaceutically acceptable carrier.

The invention thus extends to the pharmaceutical compositions containing, as active ingredient, at least one of the medicaments as defined above.

Such pharmaceutical compositions of the present invention may also, where appropriate, contain active ingredients of other antimitotic medicaments, such as in particular those based on taxol, cis-platin, DNA-intercalating agents, and the like.

These pharmaceutical compositions may be administered orally, parenterally or locally by topical application to the skin and the mucous membranes, or by intravenous or intramuscular injection.

These compositions may be solid or liquid and may be in all the pharmaceutical forms commonly used in human medicine, for instance simple or sugar-coated tablets, pills, lozenges, gel capsules, drops, granules, injectable preparations, ointments, creams or gels; they are prepared according to the usual methods. The active ingredient may be incorporated therein in excipients normally used in these pharmaceutical compositions, such as talc, gum Arabic, lactose, starch, magnesium stearate, cocoa butter, aqueous or nonaqueous carriers, fatty substances of animal or plant origin, paraffin derivatives, glycols, various wetting agents, dispersants or emulsifiers, or preservatives.

The usual dosage, which is variable depending on the product used, the individual treated and the condition in question, may, for example, be from 0.05 to 5 g per day in adults, or preferably from 0.1 to 2 g per day.

A subject of the present invention is also the use of products of formula (I) as defined above, for the preparation of a medicament for use in the treatment or prevention of a disease characterized by the disregulation of the activity of a protein or lipid kinase.

Such a medicament may in particular be for use in the treatment or prevention of a disease in a mammal.

A subject of the present invention is in particular the use of a product of formula (I) as defined above, for the preparation of a medicament for use in the prevention or treatment of various diseases, such as cardiovascular diseases, including in particular thrombosis.

A subject of the present invention is in particular the use of a product of formula (I) as defined above, for the preparation of a medicament for use in the prevention or treatment of diseases associated with an uncontrolled proliferation.

A subject of the present invention is thus most particularly the use of a product of formula (I) as defined above, for the preparation of a medicament for use in the treatment or prevention of diseases in oncology, and in particular for use in the treatment of cancers.

Among these cancers, the focus is on the treatment of solid or liquid tumours, and on the treatment of cancers resistant to cytotoxic agents.

The cited products of the present invention may especially be used for the treatment of primary tumours and/or of metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid haematopoietic tumours, in sarcomas, in brain, larynx and lymphatic system cancers, bone and pancreatic cancers, and in hamartomas. Also involved, in particular, are diseases which exhibit genetic anomalies resulting in the activation of the PI3K/AKT/mTOR pathway and/or in the activation of the MAP kinase pathway.

A subject of the present invention is also the use of the products of formula (I) as defined above, for the preparation of medicaments for use in cancer chemotherapy.

A subject of the present invention is thus the products of formula (I) as defined above, for the use thereof in the treatment of cancers.

A subject of the present invention is the products of formula (I) as defined above, for the use thereof in the treatment of solid or liquid tumours.

A subject of the present invention is therefore the products of formula (I) as defined above, for the use thereof in the treatment of cancers resistant to cytotoxic agents.

A subject of the present invention is therefore the products of formula (I) as defined above, for the use thereof in the treatment of primary tumours and/or metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid haematopoietic tumours, in sarcomas, in brain, larynx and lymphatic system cancers, bone and pancreatic cancers, and in hamartomas.

A subject of the present invention is therefore the products of formula (I) as defined above, for the use thereof in cancer chemotherapy.

A subject of the present invention is therefore the products of formula (I) as defined above, for the use thereof in cancer chemotherapy, alone or in combination.

Such medicaments for use in cancer chemotherapy may be used alone or in combination.

The products of the present invention may in particular be administered alone or in combination with chemotherapy or radiotherapy or else in combination, for example, with other therapeutic agents.

Such therapeutic agents may be commonly used antitumour agents.

A therapeutic benefit can in particular be expected by administering the products of the present application in combinations with varied targeted therapies. These targeted therapies are in particular the following: i) therapies which inhibit the MAP kinase signalling pathway, for instance therapies which inhibit RAS, RAF, MEK or ERK; ii) targeted therapies which inhibit the kinases or pseudokinases of the PI3K/AKT/mTOR pathway, for instance EGFR, HER2, HER3, ALK, MET, PI3K, PDK1, AKT, mTOR and S6K.

A subject of the present invention is in particular the use of a product of formula (I) as defined above, for the preparation of a medicament for use in the prevention or treatment of lysosomal diseases such as glycogenosis type II or Pompe disease. Such medicaments for use in the treatment of lysosomal diseases can be used alone or in combination, for example, with other therapeutic agents.

A subject of the present invention is thus the products of formula (I) as defined above, for the prevention or treatment of lysosomal diseases such as glycogenosis type II or Pompe disease.

A subject of the present invention is thus the use of the products of formula (I) as defined above, for the preparation of a medicament for use in the prevention or treatment of lysosomal diseases such as glycogenosis type II or Pompe disease.

A subject of the present invention is thus the use as defined above, in which said products of formula (I) are alone or in combination.

A subject of the present invention is also the use of a product of formula (I) as defined above, for the preparation of a medicament for use in the treatment of parasitic diseases such as malaria, sleeping sickness, Chagas disease or leishmaniasis. Such medicaments for use in the treatment of parasitic infections can be used alone or in combination, for example, with other therapeutic agents.

A subject of the present invention is thus the products of formula (I) as defined above, for the treatment of parasitic diseases such as malaria, sleeping sickness, Chagas disease or leishmaniasis.

A subject of the present invention is thus the use of the products of formula (I) as defined above, for the preparation of a medicament for the treatment of parasitic diseases such as malaria, sleeping sickness, Chagas disease or leishmaniasis.

A subject of the present invention is also, as novel industrial products, the synthesis intermediates of formulae C, D, E and J as defined above and recalled below:

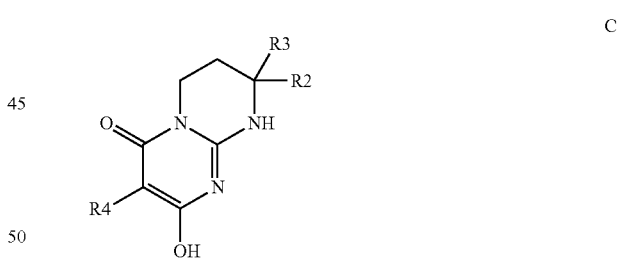

C

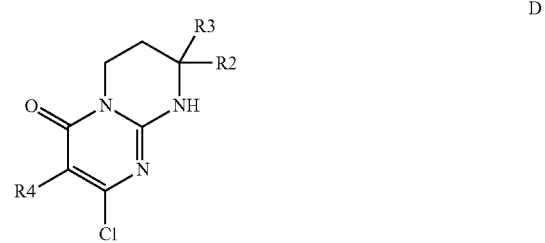

D

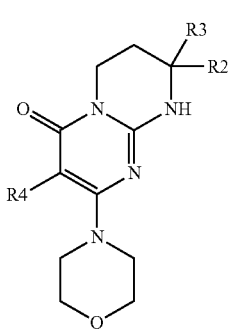

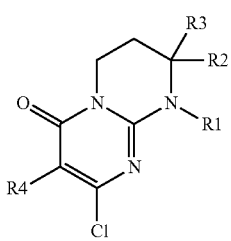

in which R1, R2, R3 and R4 have the meanings indicated in either one of Claims 1 and 2.

The following examples, which are products of formula (I), illustrate the invention without, however, limiting it.

Experimental Section

The nomenclature of the compounds of this present invention was carried out with the ACDLABS software, Version 10.0.

The microwave used is a Biotage apparatus, Initiator™ 2.0, 400 W max, 2450 MHz.

The 1H NMR spectra at 400 MHz and 1H NMR spectra at 500 MHz were performed on a Bruker Avance DRX-400 or Bruker Avance DPX-500 spectrometer with the chemical shifts (δ in ppm) in the solvent dimethyl sulfoxide-$d_6$ (DMSO-$d_6$) referenced at 2.5 ppm at a temperature of 303 K.

The mass spectra (MS) were obtained either by method A or by method B or by method E:

Method A:

Waters HPLC-SQD instrument; ionization: positive and/or negative mode electrospray (ES+/−); chromatographic conditions: column: Acquity BEH C18 1.7 μm-2.1×50 mm; solvents: A: $H_2O$ (0.1% formic acid) B: $CH_3CN$ (0.1% formic acid); column temperature: 50° C.; flow rate: 1 ml/min; gradient (2 min): from 5% to 50% of B in 0.8 min; 1.2 min: 100% of B; 1.85 min: 100% of B; 1.95; 5% of B; retention time=Tr (min).

Method B:

Waters ZQ instrument; ionisation: positive and/or negative mode electrospray (ES+/−); chromatographic conditions: column: XBridge $C_{18}$ 2.5 μm-3×50 mm; solvents: A: $H_2O$ (0.1% formic acid) B: $CH_3CN$ (0.1% formic acid); column temperature: 70° C.; flow rate: 0.9 ml/min; gradient (7 min): from 5% to 100% of B in 5.3 min; 5.5 min: 100% of B; 6.3 min: 5% of B; retention time=Tr (min).

Method E:

Waters HPLC-SQD instrument; ionisation: positive and/or negative mode electrospray (ES+/−); chromatographic conditions: column: Ascentis express C18 2.7 μm-2.1×50 mm; solvents: A: $H_2O$ (0.02% trifluoroacetic acid) B: $CH_3CN$ (0.014% trifluoroacetic acid); column temperature: 55° C.; flow rate: 1 ml/min; gradient: T0 min 2% B, T1 min 98% B, T1.3 min 98% B, T1.33 min 2% B, T1.5 other injection; retention time=Tr (min).

The optical rotations (OR) were measured on a polarimeter model 341 from Perkin Elmer. Wavelength: a line of sodium (589 nanometres).

Purifications by preparative HPLC/MS:

Method C

SunFire C18 reverse phase column (Waters) 30×100, 5μ.

Gradient of acetonitrile (+0.07% TFA) in water (+0.07% TFA)

T0: 20% acetonitrile (+0.07% TFA)
T1: 20% acetonitrile (+0.07% TFA)
T11.5: 95% acetonitrile (+0.07% TFA)
T15: 95% acetonitrile (+0.07% TFA)
T15.5: 20% acetonitrile (+0.07% TFA)
Flow rate: 30 ml/min
Mass: 130_800 AMU=; ESP+, ESP Method D SunFire C18 reverse phase column (Waters) 30×100, 5μ.

Gradient of acetonitrile (+0.07% TFA) in water (+0.07% TFA)

T0: 40% acetonitrile (+0.07% TFA)
T1: 40% acetonitrile (+0.07% TFA)
T11: 95% acetonitrile (+0.07% TFA)
T14.5: 95% acetonitrile (+0.07% TFA)
T15: 10% acetonitrile (+0.07% TFA)
Flow rate: 30 ml/min
Mass: 130_800 AMU=; ESP+, ESP

EXAMPLE 1

(S)-9-[2-(4-methoxyphenyl)ethyl]-2-morpholin-4-yl-8-trifluoromethyl-6,7,8,9-tetrahydropyrimido[1,2-a]pyrimidin-4-one

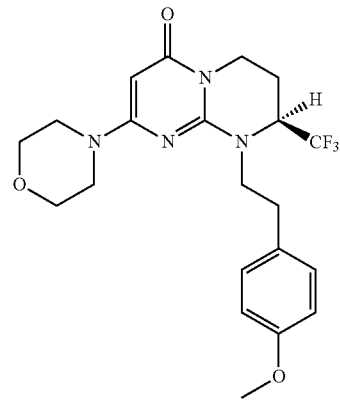 [SMILES: COc1ccc(CCN2c3nc(N4CCOCC4)cc(=O)n3CC[C@H]2C(F)(F)F)cc1]

Stage f: (S)-9-[2-(4-methoxyphenyl)ethyl]-2-morpholin-4-yl-8-trifluoromethyl-6,7,8,9-tetrahydropyrimido[1,2-a]pyrimidin-4-one 0.5 g of caesium carbonate, 0.23 g of 4-methoxyphenethyl bromide and 5 mg of benzyltriethylammonium chloride (BTEAC) are added, at ambient temperature and under an argon atmosphere, to a solution of 150 mg of (S)-2-morpholin-4-yl-8-trifluoromethyl-6,7,8,9-tetrahydropyrimido[1,2-a]pyrimidin-4-one in 5 ml of anhydrous dimethylformamide. The reaction mixture is heated at 80° C. for 18 hours.

After cooling, 10 ml of cold water and 50 ml of ethyl acetate are added to the mixture obtained. The organic phase is separated and then dried over magnesium sulphate, filtered, and concentrated under reduced pressure. The residue obtained is purified by silica chromatography (gradient of 0% to 20% of the eluent $CH_2Cl_2$/MeOH/$NH_4OH$ 28% 38/17/2 in dichloromethane), so as to give 160 mg of (S)-9-[2-(4-methoxyphenyl)ethyl]-2-morpholin-4-yl-8-trifluoromethyl-6,7,8,9-tetrahydropyrimido[1,2-a]pyrimidin-4-one, the characteristics of which are the following:

1H NMR spectrum:

1.82 to 2.05 (m, 1 H); 2.25 to 2.39 (m, 1 H); 2.73 to 2.83 (m, 1 H); 2.88 to 2.99 (m, 1 H); 3.10 to 3.21 (m, 1 H); 3.34 to 3.41 (m, 1 H); 3.43 to 3.46 (m, 4 H); 3.65 (m, 4 H); 3.72 (s, 3 H); 4.03 to 4.23 (m, 2 H); 4.47 to 4.60 (m, 1 H); 4.99 (s, 1 H); 6.87 (d, J=8.6Hz, 2 H); 7.12 (d, J=8.6Hz, 2 vH).

Mass spectrometry: method A

Retention time Tr (min)=0.93

[M+H]+: m/z 439

Optical rotation: OR=+91; C=2.426 mg/0.5 ml MeOH.

Stage e: (S)-2-morpholin-4-yl-8-trifluoromethyl-6,7,8,9-tetrahydro-pyrimido[1,2-a]pyrimidin-4-one

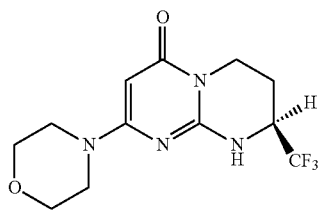 [SMILES: O=c1cc(N2CCOCC2)nc2n1CC[C@@H](C(F)(F)F)N2]

A mixture of 1 g of (S)-2-chloro-8-trifluoromethyl-6,7,8,9-tetrahydro-pyrimido[1,2-a]pyrimidin-4-one and of 15 ml of morpholine is heated at 80° C. After one and a half hours of heating and after verification by LC/MS, the reaction is complete. After cooling, the reaction mixture is concentrated under reduced pressure. 10 ml of cold water and 100 ml of ethyl acetate are added to the residue obtained. The resulting organic phase is separated and then dried over magnesium sulphate, filtered, and concentrated under reduced pressure so as to give 1.2 g of (S)-2-morpholin-4-yl-8-trifluoromethyl-6,7,8,9-tetrahydropyrimido[1,2-a]pyrimidin-4-one, the characteristics of which are the following:

Mass spectrometry: method A

Retention time Tr (min)=0.49

[M+H]+: m/z 305; [M–H]–: m/z 303

Optical rotation: OR=+14.2+/–0.6; C=2.25 mg/0.5 ml MeOH.

Stage d: (S)-2-chloro-8-trifluoromethyl-6,7,8,9-tetrahydropyrimido[1,2-a]pyrimidin-4-one

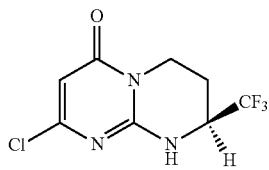

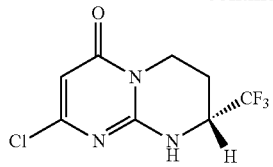

The two enantiomers of (R,S)-2-chloro-8-trifluoromethyl-6,7,8,9-tetrahydropyrimido[1,2-a]pyrimidin-4-one (17 g) are separated by chiral chromatography: stationary phase: Chiralpak AD; mobile phase: EtOH (20%)/heptane (80%).

The laevorotary enantiomer is concentrated so as to give 8.52 g of (R)-2-chloro-8-trifluoromethyl-6,7,8,9-tetrahydropyrimido[1,2-a]pyrimidin-4-one, in the form of a white powder.

The dextrorotary enantiomer is concentrated so as to obtain 8.21 g of (S)-2-chloro-8-trifluoromethyl-6,7,8,9-tetrahydropyrimido[1,2-a]pyrimidin-4-one, in the form of a white powder, the characteristics of which are the following:

Mass spectrometry: method A

Retention time Tr (min)=0.51

[M+H]+: m/z 254; [M–H]–: m/z 252

Optical rotation: OR=+21.3+/–0.5. MeOH.

Stage c: (R,S)-2-chloro-8-trifluoromethyl-6,7,8,9-tetrahydropyrimido[1,2-a]pyrimidin-4-one

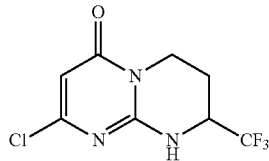 [SMILES: O=c1cc(Cl)nc2n1CCC(C(F)(F)F)N2]

60 ml of phosphorus oxychloride are added, at ambient temperature and under an argon atmosphere, to a suspension of 34 g of (R,S)-2-hydroxy-8-trifluoromethyl-6,7,8,9-tetrahydropyrimido[1,2-a]pyrimidin-4-one in 500 ml of 1,2-dichloroethane. The mixture obtained is then heated to 65° C. After stirring for three hours at 65° C., the reaction is complete according to the verification by LC/MS. After cooling, the reaction mixture is evaporated to dryness under reduced pressure. The residue obtained is taken up with 100 ml of cold water and 400 ml of ethyl acetate. 32% sodium hydroxide is added to the mixture obtained, until pH=6. The resulting organic phase is separated and then dried over magnesium sulphate, filtered, and concentrated under reduced pressure so as to give an orange residue. This residue is purified by silica chromatography (eluent: $CH_2Cl_2$/MeOH: 97/03) so as to give 20 g of (R,S)-2-chloro-8-trifluoromethyl-6,7,8,9-tetrahydropyrimido[1,2-a]pyrimidin-4-one, in the form of a white solid, the characteristics of which are the following:

Mass spectrometry: method A

Retention time Tr (min)=0.51

[M+H]+: m/z 254; [M–H]–: m/z 252.

Stage b: (R,S)-2-hydroxy-8-trifluoromethyl-6,7,8,9-tetrahydro-pyrimido[1,2-a]pyrimidin-4-one

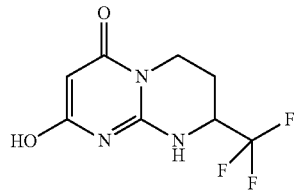 [SMILES: O=c1cc(O)nc2n1CCC(C(F)(F)F)N2]

10 g of 6-trifluoromethyl-1,4,5,6-tetrahydropyrimidin-2-ylamine hydrochloride and 10 g of sodium methoxide are added to a mixture of 50 ml of diethyl malonate. The mixture obtained is brought to 100° C. for 75 minutes. The heterogeneous mixture thickens and turns yellow with a small amount of gas being given off. After cooling, the reaction mixture is evaporated to dryness under reduced pressure. The residue obtained is triturated with ethyl ether. The solid formed is filtered off on a sintered glass filter and then taken up with 20 ml of cold water. 12 N hydrochloric acid is added to the thick suspension obtained, until pH=5-6. The suspension obtained is filtered through sintered glass and the insoluble material is rinsed with ethyl ether so as to give 11.5 g of (R,S)-2-hydroxy-8-trifluoromethyl-6,7,8,9-tetrahydro-pyrimido[1,2-a]pyrimidin-4-one, in the form of a white solid, the characteristics of which are the following:

Mass spectrometry: method A
Retention time Tr (min)=0.26
[M+H]+: m/z 236; [M−H]−: m/z 234.

Stage a: (R,S)-6-trifluoromethyl-1,4,5,6-tetrahydro-pyrimidin-2-ylamine hydrochloride

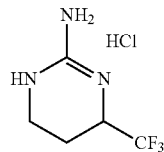

In an autoclave, a mixture of 1.1 g of Pd/C at 10%, 22 g of 2-amino-4-(trifluoromethyl)pyrimidine dissolved in 200 ml of water, 50 ml of methanol and 50 ml of 12N HCl are hydrogenated, under 3 bar, at 22° C., for 24 hours. The resulting mixture is then filtered and the filtrate is concentrated under reduced pressure. The residue obtained is oven-dried, in the presence of $P_2O_5$, so as to give 27 g of (R,S)-6-trifluoromethyl-1,4,5,6-tetrahydropyrimidin-2-ylamine hydrochloride, in the form of a grey solid, the characteristics of which are the following:

Mass spectrometry: method A
Retention time Tr (min)=0.17
[M+H]+: m/z 168.

EXAMPLE 2

(R,S)-9-[2-(4-methoxyphenyl)ethyl]-2-morpholin-4-yl-8-trifluoromethyl-6,7,8,9-tetrahydropyrimido[1,2-a]pyrimidin-4-one

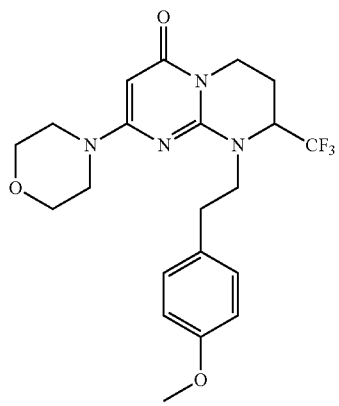 [SMILES: COc1ccc(CCN2c3nc(N4CCOCC4)cc(=O)n3CCC2C(F)(F)F)cc1]

Stage b: (R,S)-9-[2-(4-methoxyphenyl)ethyl]-2-morpholin-4-yl-8-trifluoro-methyl-6,7,8,9-tetrahydropyrimido[1,2-a]pyrimidin-4-one 0.5 g of caesium carbonate, 0.23 g of 4-methoxyphenethyl bromide and 10 mg of benzyltriethylammonium chloride (BTEAC) are added, at ambient temperature and under an argon atmosphere, to a solution of 120 mg of (R,S)-2-morpholin-4-yl-8-trifluoromethyl-6,7,8,9-tetrahydropyrimido[1,2-a]pyrimidin-4-one in 5 ml of anhydrous dimethylformamide. The resulting mixture is heated at 80° C. for 18 hours.

After cooling, the reaction mixture is concentrated under reduced pressure. The residue obtained is taken up with 50 ml of ethyl acetate and the solution obtained is washed with 3 ml of water. The organic phase is separated and then dried over magnesium sulphate, filtered, and evaporated under reduced pressure. After purification by silica chromatography (gradient of 0% to 20% of the eluent $CH_2Cl_2$/MeOH/$NH_4OH$ 28% 38/17/2 in dichloromethane), 80 mg of (R,S)-(9-[2-(4-methoxyphenyl)ethyl]-2-morpholin-4-yl-8-trifluoromethyl-6,7,8,9-tetrahydropyrimido[1,2-a]pyrimidin-4-one are obtained, the characteristics of which are the following:

1H NMR spectrum:

1.85 to 2.02 (m, 1 H); 2.27 to 2.35 (m, 1 H); 2.72 to 2.84 (m, 1 H); 2.88 to 2.98 (m, 1 H); 3.09 to 3.20 (m, 1 H); 3.37 to 3.42 (m, 1 H); 3.45 (m, 4 H);

3.63 to 3.67 (m, 4 H); 3.72 (s, 3 H); 4.08 (m, 1 H); 4.14 to 4.21 (m, 1 H); 4.51 to 4.63 (m, 1 H); 5.00 (s, 1 H); 6.88 (d, J=8.6 Hz, 2 H); 7.13 (d, J=8.6 Hz, 2 H).

Mass spectrometry: method A
Retention time Tr (min)=0.93
[M+H]+: m/z 439.

Stage a: (R,S)-2-morpholin-4-yl-8-trifluoromethyl-6,7,8,9-tetrahydro-pyrimido[1,2-a]pyrimidin-4-one

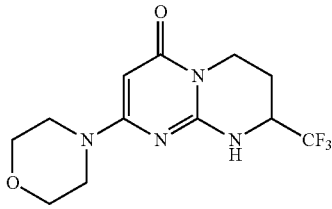 [SMILES: O=c1cc(N2CCOCC2)nc2n1CCC(C(F)(F)F)N2]

A mixture of 220 mg of (R,S)-2-chloro-4-yl-8-trifluoromethyl-6,7,8,9-tetrahydropyrimido[1,2-a]pyrimidin-4-one in 5 ml of morpholine is heated to 80° C. After heating for one and a half hours, the reaction is complete according to the verification by LC/MS. After cooling, the reaction mixture is concentrated under reduced pressure. The residue obtained is purified by silica chromatography (gradient of 5% to 20% of the eluent CH$_2$Cl$_2$/MeOH/NH$_4$OH 28% 38/17/2 in dichloromethane) so as to give 270 mg of (R,S)-2-morpholin-4-yl-8-trifluoromethyl-6,7,8,9-tetrahydropyrimido[1,2-a]pyrimidin-4-one, the characteristics of which are the following:
Mass spectrometry: method B
Retention time Tr (min)=2.53
[M+H]+: m/z 305; [M−H]−: m/z 303.

EXAMPLE 3

(S)-2-morpholin-4-yl-9-phenethyl-8-trifluoromethyl-6,7,8,9-tetrahydropyrimido[1,2-a]pyrimidin-4-one

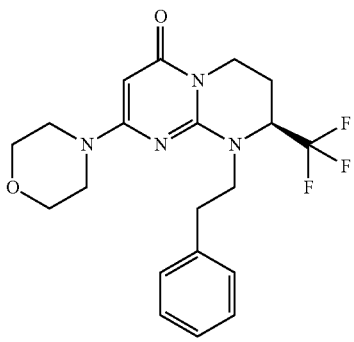 [SMILES: O=c1cc(N2CCOCC2)nc2n1CC[C@@H](C(F)(F)F)N2CCc1ccccc1]

Stage a:
(R,S)-2-morpholin-4-yl-9-phenethyl-8-trifluoromethyl-6,7,8,9-tetrahydropyrimido[1,2-a]pyrimidin-4-one is prepared according to the procedure described in Example 2, using 80 mg of (R,S)-2-morpholin-4-yl-8-trifluoromethyl-6,7,8,9-tetrahydropyrimido[1,2-a]pyrimidin-4-one and 240 mg of (2-bromoethyl)benzene. After purification by silica chromatography (eluent: a gradient of 5% to 20% of the eluent CH$_2$Cl$_2$/MeOH/NH$_4$OH 28% 38/17/2 in dichloromethane), 75 mg of (R,S)-2-morpholin-4-yl-9-phenethyl-8-trifluoromethyl-6,7,8,9-tetrahydropyrimido[1,2-a]pyrimidin-4-one are obtained, the characteristics of which are the following:
1H NMR spectrum:
1.85 to 2.01 (m, 1 H); 2.27 to 2.35 (m, 1 H); 2.86 (m, 1 H); 2.95 to 3.05 (m, 1 H); 3.11 to 3.21 (m, 1 H); 3.39 to 3.49 (m, 5 H); 3.63 to 3.68 (m, 4 H); 4.08 to 4.23 (m, 2 H); 4.53 to 4.62 (m, 1 H); 5.00 (s, 1 H); 7.18 to 7.25 (m, 3 H); 7.29 to 7.34 (m, 2 H).

Mass spectrometry: method A
Retention time Tr (min)=0.95
[M+H]+: m/z 409.
Stage b:
The two enantiomers of (R,S)-2-morpholin-4-yl-9-phenethyl-8-trifluoromethyl-6,7,8,9-tetrahydropyrimido[1,2-a]pyrimidin-4-one are separated by chiral chromatography: Chiralpak IC 20 μm column; elution 75% heptane/20% EtOH/5% MeOH.
The dextrorotary enantiomer is concentrated so as to obtain 27 mg of (S)-2-morpholin-4-yl-9-phenethyl-8-trifluoromethyl-6,7,8,9-tetrahydropyrimido-[1,2-a]pyrimidin-4-one, the characteristics of which are the following:
1H NMR spectrum:
1.94 (m, 1 H); 2.23 to 2.35 (m, 1 H); 2.83 to 2.91 (m, 1 H); 2.96 to 3.04 (m, 1 H); 3.16 (m, 1 H); 3.40 to 3.52 (m, 5 H); 3.65 (m, 4 H); 4.07 to 4.21 (m, 2 H); 4.50 to 4.62 (m, 1 H); 5.00 (s, 1 H); 7.18 to 7.25 (m, 3 H); 7.29 to 7.35 (m, 2 H).
Mass spectrometry: method A
Retention time Tr (min)=0.95
[M+H]+: m/z 409
Optical rotation: OR=positive sign (+40); C=1.093 mg/0.5 ml DMSO.

The chromatographic purification also results in 30 mg of the laevorotary enantiomer, (R)-2-morpholin-4-yl-9-phenethyl-8-trifluoromethyl-6,7,8,9-tetrahydropyrimido[1,2-a]pyrimidin-4-one.

EXAMPLE 4

(S)-9-benzyl-2-morpholin-4-yl-8-trifluoromethyl-6,7,8,9-tetrahydropyrimido[1,2-a]pyrimidin-4-one

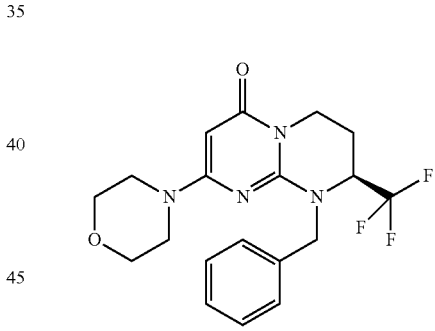

Stage b:
The two enantiomers of (R,S)-9-benzyl-2-morpholin-4-yl-8-trifluoromethyl-6,7,8,9-tetrahydropyrimido[1,2-a]pyrimidin-4-one are separated by chiral chromatography: 6×35 cm column; mobile phase: 60% EtOH/40% heptane.
The dextrorotary enantiomer is concentrated so as to give 36 mg of (S)-9-benzyl-2-morpholin-4-yl-8-trifluoromethyl-6,7,8,9-tetrahydro-pyrimido[1,2-a]pyrimidin-4-one, the characteristics of which are the following:
1H NMR spectrum:
2.10 to 2.25 (m, 1 H); 2.35 to 2.43 (m, 1 H); 3.19 to 3.27 (m, 5 H); 3.39 to 3.53 (m, 4 H); 4.16 to 4.27 (m, 1 H); 4.51 (d, J=15.9 Hz, 1 H); 4.57 to 4.72 (m, 1 H); 4.96 (s, 1 H); 5.23 (d, J=15.9 Hz, 1 H); 7.20 to 7.27 (m, 3 H); 7.28 to 7.34 (m, 2 H).
Mass spectrometry: method A
Retention time Tr (min)=0.88
[M+H]+: m/z 395
Optical rotation: OR=+16.3+/−0.7. C=1.960 mg/0.5 ml DMSO.

The chromatographic purification above also results in 38 mg of the laevorotary enantiomer, (R)-9-benzyl-2-morpholin-4-yl-8-trifluoromethyl-6,7,8,9-tetrahydropyrimido[1,2-a]pyrimidin-4-one.

Stage a: (R,S)-9-benzyl-2-morpholin-4-yl-8-trifluoromethyl-6,7,8,9-tetrahydropyrimido[1,2-a]pyrimidin-4-one

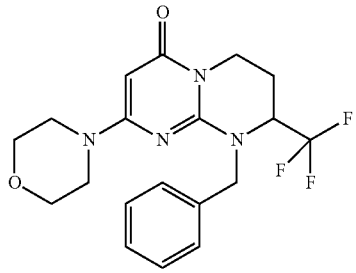 [SMILES: O=c1cc(N2CCOCC2)nc2n1CCC(C(F)(F)F)N2Cc1ccccc1]

The product is prepared according to the procedure described in Example 2, using 140 mg of (R,S)-2-morpholin-4-yl-8-trifluoromethyl-6,7,8,9-tetrahydropyrimido[1,2-a]pyrimidin-4-one and 0.270 ml of benzyl bromide. After purification by silica chromatography (gradient of 5% to 20% of the eluent $CH_2Cl_2$/MeOH/$NH_4OH$ 28% 38/17/2 in dichloromethane), 32 mg of (R,S)-9-benzyl-2-morpholin-4-yl-8-trifluoromethyl-6,7,8,9-tetrahydro-pyrimido[1,2-a]pyrimidin-4-one are obtained, the characteristics of which are the following:

1H NMR spectrum:
2.11 to 2.25 (m, 1 H); 2.35 to 2.44 (m, 1 H); 3.17 to 3.27 (m, 5 H); 3.40 to 3.53 (m, 4 H); 4.18 to 4.29 (m, 1 H); 4.51 (d, J=15.9 Hz, 1 H); 4.58 to 4.72 (m, 1 H); 4.96 (s, 1 H); 5.22 (d, J=15.9 Hz, 1 H); 7.20 to 7.27 (m, 3 H); 7.28 to 7.36 (m, 2 H).

Mass spectrometry: method A
Retention time Tr (min)=0.88
[M+H]+: m/z 395.

EXAMPLE 5

9-((S)-2-hydroxy-2-phenylethyl)-2-morpholin-4-yl-8-(S)-trifluoromethyl-6,7,8,9-tetrahydropyrimido[1,2-a]pyrimidin-4-one

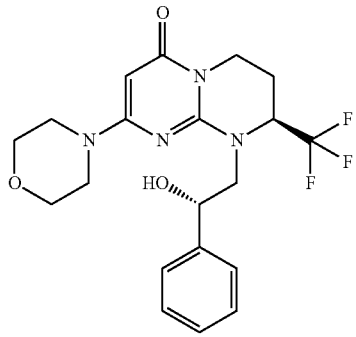 [SMILES: O=c1cc(N2CCOCC2)nc2n1CC[C@@H](C(F)(F)F)N2C[C@@H](O)c1ccccc1]

The product is prepared according to the procedure described in Example 2, using 135 mg of (R,S)-2-morpholin-4-yl-8-trifluoromethyl-6,7,8,9-tetrahydropyrimido[1,2-a]pyrimidin-4-one and 342 mg of (S)-2-chloro-1-phenylethanol. After purification by silica chromatography (gradient of 5% to 20% of the eluent $CH_2Cl_2$/MeOH/$NH_4OH$ 28% 38/17/2 in dichloromethane), 26 mg of 9-((S)-2-hydroxy-2-phenylethyl)-2-morpholin-4-yl-8-(R)-trifluoro-methyl-6,7,8,9-tetrahydropyrimido[1,2-a]pyrimidin-4-one and 18 mg of (S)-9-((S)-2-hydroxy-2-phenylethyl)-2-morpholin-4-yl-8-trifluoromethyl-6,7,8,9-tetrahydropyrimido[1,2-a]pyrimidin-4-one are obtained, the characteristics of which are the following:

1H NMR spectrum:
2.24 (m, 1 H); 2.36 to 2.46 (m, 1 H); 3.08 (dd, J=10.0 and 14.2 Hz, 1 H); 3.17 to 3.27 (m, 1 H); 3.40 to 3.48 (m, 4 H); 3.63 to 3.69 (m, 4 H); 4.17 to 4.32 (m, 2 H); 4.74 to 4.85 (m, 1 H); 4.99 (m, 1 H); 5.02 (s, 1 H); 5.67 (d, J=5.1 Hz, 1 H); 7.22 to 7.44 (m, 5 H).

Mass spectrometry: method A
Retention time Tr (min)=0.85
[M+H]+: m/z 425; [M−H+ $HCO_2H$]−: m/z 469
Optical rotation: OR=+7.4+/−0.6; C=1.959 mg/0.5 ml $CH_3OH$.

EXAMPLE 6

9-(R)-2-hydroxy-2-phenylethyl)-2-morpholin-4-yl-8-(S)-trifluoromethyl-6,7,8,9-tetrahydropyrimido[1,2-a]pyrimidin-4-one

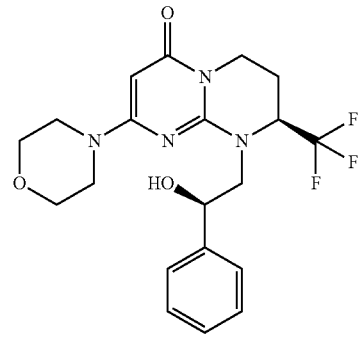 [SMILES: O=c1cc(N2CCOCC2)nc2n1CC[C@@H](C(F)(F)F)N2C[C@H](O)c1ccccc1]

The product is prepared according to the procedure described in Example 2, using 135 mg of (R,S)-2-morpholin-4-yl-8-trifluoromethyl-6,7,8,9-tetrahydropyrimido[1,2-a]pyrimidin-4-one and 342 mg of (R)-2-chloro-1-phenylethanol. After purification by silica chromatography (gradient of 5% to 20% of the eluent $CH_2Cl_2$/MeOH/$NH_4OH$ 28% 38/17/2 in dichloromethane), 25 mg of 9-((R)-2-hydroxy-2-phenylethyl)-2-morpholin-4-yl-8-(S)-trifluoro-methyl-6,7,8,9-tetrahydropyrimido[1,2-a]pyrimidin-4-one are obtained, the characteristics of which are the following:

1H NMR spectrum:
1.40 to 1.56 (m, 1 H); 2.05 to 2.17 (m, 1 H); 3.05 to 3.20 (m, 2 H); 3.36 to 3.47 (m, 4 H); 3.62 to 3.67 (m, 4 H); 3.84 to 3.94 (m, 1 H); 3.96 to 4.03 (m, 1 H); 4.54 (dd, J=6.0 and 13.8 Hz, 1 H); 4.96 (s, 1 H); 4.99 to 5.04 (m, 1 H); 5.56 (broad s, 1 H); 7.18 to 7.37 (m, 5 H).

Mass spectrometry: method A
Retention time Tr (min)=0.73
[M+H]+: m/z 425; [M−H+$HCO_2H$]−: m/z 469
Optical rotation: OR=+63.3+/−1.4 in MeOH.

In the purification above, 20 mg of 9-((R)-2-hydroxy-2-phenylethyl)-2-morpholin-4-yl-8-(R)-trifluoromethyl-6,7,8,9-tetrahydropyrimido[1,2-a]pyrimidin-4-one are also obtained.

EXAMPLE 7

(8S)-9-[(2S)-2-hydroxy-2-(4-methoxyphenyl)ethyl]-2-(morpholin-4-yl)-8-(trifluoromethyl)-6,7,8,9-tetrahydro-4H-pyrimido[1,2-a]pyrimidin-4-one

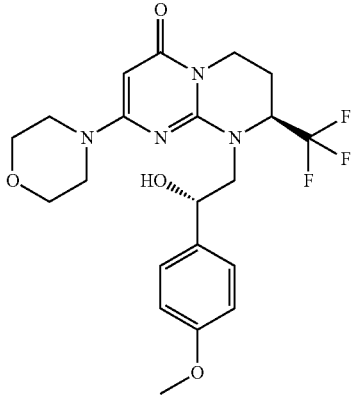 [SMILES: COc1ccc([C@H](O)CN2c3nc(N4CCOCC4)cc(=O)n3CC[C@H]2C(F)(F)F)cc1]

The product is prepared according to the procedure described in Example 2, using 135 mg of (R,S)-2-morpholin-4-yl-8-trifluoromethyl-6,7,8,9-tetrahydropyrimido[1,2-a]pyrimidin-4-one and 760 mg of (S)-2-chloro-1-(4-methoxyphenyl)ethanol. After purification by silica chromatography (gradient of 5% to 20% of the eluent $CH_2Cl_2/MeOH/NH_4OH$ 28% 38/17/2 in dichloromethane), 66 mg of (8S)-9-[(2S)-2-hydroxy-2-(4-methoxy-phenyl)ethyl]-2-(morpholin-4-yl)-8-(trifluoromethyl)-6,7,8,9-tetrahydro-4H-pyrimido[1,2-a]pyrimidin-4-one are obtained, the characteristics of which are the following:

1H NMR spectrum:
2.14 to 2.29 (m, 1 H); 2.35 to 2.44 (m, 1 H); 3.06 (dd, J=9.8 and 13.9 Hz, 1 H); 3.14 to 3.27 (m, 1 H); 3.37 to 3.50 (m, 4 H); 3.62 to 3.69 (m, 4 H); 3.74 (s, 3 H); 4.14 to 4.28 (m, 2 H); 4.79 (m, 1 H); 4.90 to 4.98 (m, 1 H); 5.01 (s, 1 H); 5.57 (d, J=4.9 Hz, 1 H); 6.93 (d, J=8.6 Hz, 2 H); 7.25 (d, J=8.6 Hz, 2 H).

Mass spectrometry: method A
Retention time Tr (min)=0.84
[M+H]+: m/z 499
Optical rotation: OR=+4; C=1.397 mg/0.5 ml in $CH_3OH$.
36 mg of (8R)-9-[(2S)-2-hydroxy-2-(4-methoxyphenyl)ethyl]-2-(morpholin-4-yl)-8-(trifluoromethyl)-6,7,8,9-tetrahydro-4H-pyrimido[1,2-a]pyrimidin-4-one are also obtained.

EXAMPLE 8

(8S)-2-(morpholin-4-yl)-9-[(1R or 1S)-1-phenylethyl]-8-(trifluoromethyl)-6,7,8,9-tetrahydro-4H-pyrimido[1,2-a]pyrimidin-4-one

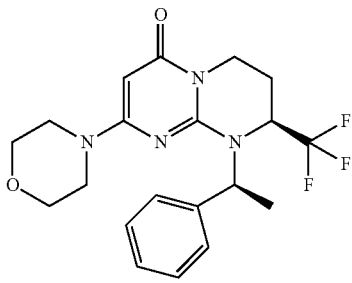 [SMILES: C[C@@H](c1ccccc1)N1c2nc(N3CCOCC3)cc(=O)n2CC[C@H]1C(F)(F)F]

The product is prepared according to the procedure described in Example 1f, using 135 mg of (S)-2-morpholin-4-yl-8-trifluoromethyl-6,7,8,9-tetrahydropyrimido[1,2-a]pyrimidin-4-one (Example 1d) in 5 ml of acetonitrile, and 520 mg of (1-bromoethyl)benzene. After purification by silica chromatography (gradient of 5% to 20% of the eluent $CH_2Cl_2/MeOH/NH_4OH$ 28% 38/17/2 in dichloromethane), 23 mg of (8S)-2-(morpholin-4-yl)-9-[1-phenylethyl]-8-(trifluoromethyl)-6,7,8,9-tetrahydro-4H-pyrimido[1,2-a]pyrimidin-4-one are obtained, in the form of a single diastereoisomer of undetermined configuration on the phenethyl chain, the characteristics of which are the following:

1H NMR spectrum:
1.65 (d, J=7.0 Hz, 3 H); 1.72 to 1.84 (m, 1 H); 2.29 to 2.38 (m, 1 H); 3.15 to 3.26 (m, 5 H); 3.43 to 3.55 (m, 4 H); 4.08 (m, 1 H); 4.31 to 4.44 (m, 1 H); 4.96 (s, 1 H); 5.67 (q, J=7.0 Hz, 1 H); 7.23 to 7.40 (m, 5 H).

Mass spectrometry: method A
Retention time Tr (min)=4.07
[M+H]+: m/z 409
Optical rotation: OR=+54.5+/−0.6; C=1.594 mg/0.5 ml $CH_3OH$.

EXAMPLE 9

(8S)-9-[(1R and 1S)-1-(4-methoxyphenyl)ethyl]-2-(morpholin-4-yl)-8-(trifluoromethyl)-6,7,8,9-tetrahydro-4H-pyrimido[1,2-a]pyrimidn-4-one

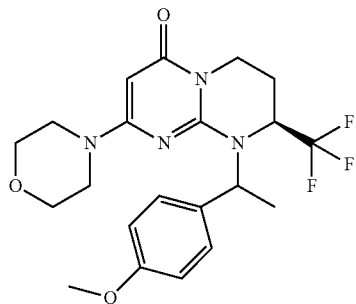 [SMILES: COc1ccc(C(C)N2c3nc(N4CCOCC4)cc(=O)n3CC[C@H]2C(F)(F)F)cc1]

In a round-bottomed flask, 130 mg of (S)-2-chloro-8-trifluoromethyl-6,7,8,9-tetrahydropyrimido[1,2-a]pyrimidin-4-one (Example 1d) are introduced into 3 ml of tetrahydrofuran, 250 mg of resin-supported triphenylphosphine (3 mmol/g) and 116 mg of 1-(4-methoxyphenyl)ethanol. 0.12 ml of diethyl azodicarboxylate is then added dropwise. After the addition, the reaction mixture is stirred for 18 hours at ambient temperature. 250 mg of resin-supported triphenylphosphine (3 mmol/g) are then added to the reaction mixture. After stirring for a further 18 hours at ambient temperature, the resulting mixture is filtered through a Millex filter and the filtrate obtained is then concentrated under reduced pressure.

The residue is dissolved in 5 ml of morpholine and the resulting mixture is heated at 80° C. for 2 hours. The reaction mixture is concentrated under reduced pressure. After purification by silica chromatography (gradient of 0% to 20% of the eluent $CH_2Cl_2/MeOH/NR_4OH$ 28% 38/17/2 in dichloromethane), 40 mg of (8S)-9-[1-(4-methoxyphenyl)ethyl]-2-(morpholin-4-yl)-8-(trifluoromethyl)-6,7,8,9-tetrahydro-4H-pyrimido[1,2-a]pyrimidin-4-one are obtained, in the form of a 60/40 mixture of the two diastereoisomers, the characteristics of which are the following:

1H NMR spectrum:
1.61 (d, J=7.1 Hz, 1.8 H); 1.68 (d, J=7.1 Hz, 1.2 H); 2.09 to 2.47 (m, 2 H); 3.10 to 3.65 (m partially masked, 9 H); 3.72 (s, 1.2 H); 3.74 (s, 1.8 H); 3.85 to 4.34 (m, 1.6 H); 4.68 to 4.87 (m, 0.4 H); 4.93 (s, 0.4 H); 4.98 (s, 0.6 H); 5.47 (q, J=7.1 Hz, 0.4 H); 5.79 (q, J=7.1 Hz, 0.6 H); 6.86 (d, J=8.6 Hz, 0.8 H); 6.92 (d, J=8.6 Hz, 1.2 H); 7.26 (d, J=8.6 Hz, 2 H).

Mass spectrometry: method A

Retention time Tr (min)=0.94 and 0.89 (60/40 mixture of the two diastereoisomers).

[M+H]+: m/z 439.

EXAMPLE 10

(8S)-9-[R1R or 1S)-1-(4-bromophenyl)ethyl]-2-(morpholin-4-yl)-8-(trifluoromethyl)-6,7,8,9-tetrahydro-4H-pyrimido[1,2-a]pyrimidin-4-one

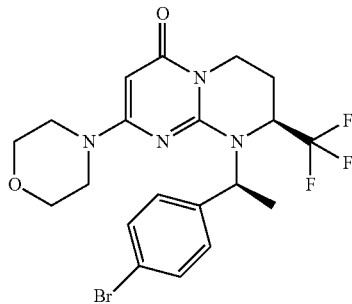 [SMILES: C[C@@H](c1ccc(Br)cc1)N1c2nc(N3CCOCC3)cc(=O)n2CC[C@H]1C(F)(F)F]

The product is prepared according to the procedure described in Example 9, using 300 mg of (S)-2-chloro-8-trifluoromethyl-6,7,8,9-tetrahydro-pyrimido[1,2-a]pyrimidin-4-one in 6 ml of tetrahydrofuran, 600 mg of resin-supported triphenylphosphine (3 mmol/g) and 354 mg of 1-(4-bromophenyl)ethanol. 0.28 ml of diethyl azodicarboxylate is then added dropwise. After the addition, the reaction mixture is stirred for 18 hours at ambient temperature. 600 mg of resin-supported triphenylphosphine (3 mmol/g) are then added to the reaction mixture. After stirring for a further 18 hours at ambient temperature, the resulting mixture is filtered through a Millex filter and the filtrate obtained is then concentrated under reduced pressure.

The evaporation residue is dissolved in 5 ml of morpholine and the mixture obtained is stirred at ambient temperature for 4 days. The reaction mixture is then concentrated under reduced pressure. After purification by silica chromatography (gradient of 0 to 20% of the eluent CH$_2$Cl$_2$/MeOH/NH$_4$OH 28% 38/17/2 in dichloromethane), 15 mg of one of the diastereoisomers of (8S)-9-[1-(4-bromophenyl)ethyl]-2-(morpholin-4-yl)-8-(trifluoromethyl)-6,7,8,9-tetrahydro-4H-pyrimido[1,2-a]pyrimidin-4-one (undetermined configuration on the phenethyl chain) are obtained, the characteristics of which are the following:

1H NMR spectrum:

1.73 (d, J=7.1 Hz, 3 H); 2.16 to 2.31 (m, 1 H); 2.39 to 2.47 (m, 1 H);

3.12 to 3.25 (m, 5 H); 3.35 to 3.51 (m, 4 H); 4.15 (m, 1 H); 4.82 to 4.90 (m, 1 H); 4.92 (s, 1 H); 5.33 (q, J=7.1 Hz, 1 H); 7.27 (d, J=8.6 Hz, 2 H); 7.49 (d, J=8.6 Hz, 2 H).

Mass spectrometry: method B

Retention time Tr (min)=4.26

[M+H]+: m/z 487

EXAMPLE 11

(8S)-9-[(1S or 1R)-1-(4-bromophenyl)ethyl]-2-(morpholin-4-yl)-8-(trifluoromethyl)-6,7,8,9-tetrahydro-4H-pyrimido[1,2-a]pyrimidin-4-one

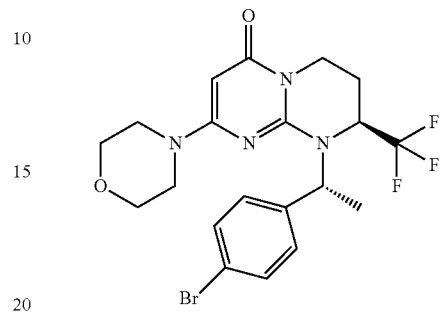

The preceding purification also produces 60 mg of the second diastereoisomer of (8S)-9-[1-(4-bromophenyl)ethyl]-2-(morpholin-4-yl)-8-(trifluoromethyl)-6,7,8,9-tetrahydro-4H-pyrimido[1,2-a]pyrimidin-4-one (undetermined configuration on the phenethyl chain), the characteristics of which are the following:

1H NMR spectrum:

1.64 (d, J=7.1 Hz, 3 H); 1.78 to 1.94 (m, 1 H); 2.30 to 2.40 (m, 1 H); 3.08 to 3.26 (m, 5 H); 3.39 to 3.52 (m, 4 H); 4.11 (m, 1 H); 4.52 (m, 1 H); 4.95 (s, 1 H); 5.50 (q, =7.1 Hz, 1 H); 7.25 (d, J=8.6 Hz, 2 H); 7.53 (d, J=8.6 Hz, 2H).

Mass spectrometry: method B

Retention time Tr (min)=4.37

[M+H]+: m/z 487.

EXAMPLE 12

(8S)-2-(morpholin-4-yl)-9-phenyl-8-(trifluoromethyl)-6,7,8,9-tetrahydro-4H-pyrimido[1,2-a]pyrimidin-4-one

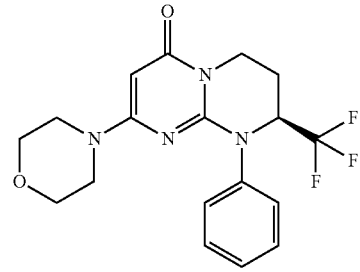

In a microwave tube, 425 mg of (S)-2-morpholin-4-yl-8-trifluoromethyl-6,7,8,9-tetrahydropyrimido[1,2-a]pyrimidin-4-one (Example 1e) are introduced into 1 ml of dimethylformamide, 422 mg of tripotassium phosphate, 380 mg of copper iodide and 2 ml of iodobenzene. The mixture obtained is heated in a microwave oven for 30 minutes at 150° C. The reaction mixture is then centrifuged. The separated supernatant is then rinsed with ethyl acetate and then evaporated to dryness. The residue is taken up with ethyl acetate and the solution obtained is washed with water. The organic phase is separated and then dried over magnesium sulphate, filtered, and concentrated under vacuum. After purification by silica chromatography (gradient of 5% to 15% of the eluent CH$_2$Cl$_2$/MeOH/NH$_4$OH 28% 38/17/2 in dichloromethane), 150 mg of (8S)-2-(morpholin-4-yl)-9-phenyl-8-(trifluoromethyl)-6,7,8,9-tetrahydro-4H-pyrimido[1,2-a]pyrimidin-4-one are obtained, the characteristics of which are the following:

1H NMR spectrum:
2.40 to 2.48 (m, 2 H); 3.00 to 3.13 (m, 4 H); 3.31 to 3.37 (m, 1 H); 3.38 to 3.48 (m, 4 H); 4.33 to 4.40 (m, 1 H); 4.93 (m, 1 H); 4.99 (s, 1 H); 7.28 to 7.37 (m, 3 H); 7.43 (t, J=7.7 Hz, 2 H).

Mass spectrometry: method A
Retention time Tr (min)=0.83
[M+H]+: m/z 381.

EXAMPLE 13

(8S)-9-(4-fluorophenyl)-2-(morpholin-4-yl)-8-(trifluoromethyl)-6,7,8,9-tetrahydro-4H-pyrimido[1,2-a]pyrimidin-4-one

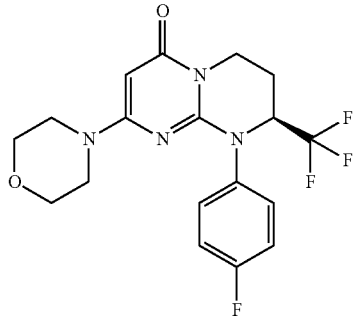 [SMILES: O=c1cc(N2CCOCC2)nc2n1CC[C@@H](C(F)(F)F)N2c1ccc(F)cc1]

The product is prepared according to the procedure described in Example 12, using 140 mg of (S)-2-morpholin-4-yl-8-trifluoromethyl-6,7,8,9-tetrahydropyrimido[1,2-a]pyrimidin-4-one (Example 1e) and 0.66 ml of 1-fluoro-4-iodobenzene. After purification by silica chromatography (gradient of 5% to 15% of the eluent CH$_2$Cl$_2$/MeOH/NH$_4$OH 28% 38/17/2 in dichloromethane), 125 mg of (8S)-9-(4-fluorophenyl)-2-(morpholin-4-yl)-8-(trifluoromethyl)-6,7,8,9-tetrahydro-4H-pyrimido[1,2-a]pyrimidin-4-one are obtained, the characteristics of which are the following:

1H NMR spectrum:
2.41 to 2.48 (m, 2 H); 3.01 to 3.15 (m, 4 H); 3.33 to 3.37 (m, 1 H); 3.40 to 3.50 (m, 4 H); 4.35 (m, 1 H); 4.82 to 4.94 (m, 1 H); 5.00 (s, 1 H); 7.25 (t, J=8.8 Hz, 2 H); 7.40 (dd, J=5.6 and 8.8 Hz, 2 H).

Mass spectrometry: method A
Retention time Tr (min)=0.86
[M+H]+: m/z 399.

EXAMPLE 14

(8S)-9-(3-fluorophenyl)-2-(morpholin-4-yl)-8-(trifluoromethyl)-6,7,8,9-tetrahydro-4H-pyrimido[1,2-a]pyrimidin-4-one

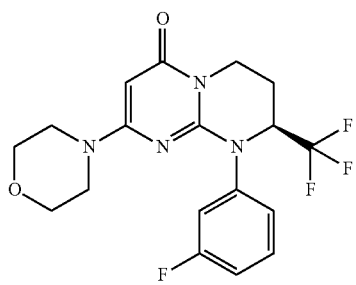 [SMILES: O=c1cc(N2CCOCC2)nc2n1CC[C@@H](C(F)(F)F)N2c1cccc(F)c1]

The product is prepared according to the procedure described in Example 12, using 140 mg of (S)-2-morpholin-4-yl-8-trifluoromethyl-6,7,8,9-tetrahydropyrimido[1,2-a]pyrimidin-4-one (Example 1e) and 0.66 ml of 1-fluoro-3-iodobenzene. After purification by silica chromatography (gradient of 5% to 15% of the eluent CH$_2$Cl$_2$/MeOH/NH$_4$OH 28% 38/17/2 in dichloromethane), 60 mg of (8S)-9-(3-fluorophenyl)-2-(morpholin-4-yl)-8-(trifluoromethyl)-6,7,8,9-tetrahydro-4H-pyrimido[1,2-a]pyrimidin-4-one are obtained, the characteristics of which are the following:

1H NMR spectrum:
2.41 to 2.48 (m, 2 H); 3.03 to 3.15 (m, 4 H); 3.25 to 3.27 (m, 1 H); 3.42 to 3.49 (m, 4 H); 4.32 to 4.41 (m, 1 H); 4.93 to 5.00 (m, 1 H); 5.02 (s, 1 H); 7.14 to 7.24 (m, 2 H); 7.30 (td, J=2.2 and 10.5 Hz, 1H); 7.46 (dt, J=6.7 and 8.1 Hz, 1 H).

Mass spectrometry: method A
Retention time Tr (min)=0.86
[M+H]+: m/z 399.

EXAMPLE 15

(8S)-9-(2-fluorophenyl)-2-(morpholin-4-yl)-8-(trifluoromethyl)-6,7,8,9-tetrahydro-4H-pyrimido[1,2-a]pyrimidin-4-one

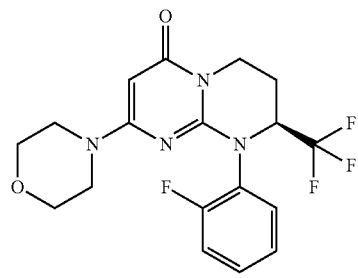 [SMILES: O=c1cc(N2CCOCC2)nc2n1CC[C@@H](C(F)(F)F)N2c1ccccc1F]

The product is prepared according to the procedure described in Example 12, using 140 mg of (S)-2-morpholin-4-yl-8-trifluoromethyl-6,7,8,9-tetrahydropyrimido[1,2-a]pyrimidin-4-one (Example 1e) and 0.66 ml of 1-fluoro-2-iodobenzene. After purification by silica chromatography (gradient of 5% to 15% of the eluent CH$_2$Cl$_2$/MeOH/NH$_4$OH 28% 38/17/2 in dichloromethane), 12 mg of (8S)-9-(2-fluorophenyl)-2-(morpholin-4-yl)-8-(trifluoromethyl)-6,7,8,9-tetrahydro-4H-pyrimido[1,2-a]pyrimidin-4-one are obtained, the characteristics of which are the following:

1H NMR spectrum:
2.37 to 2.47 (m, 2 H); 3.05 to 3.09 (m, 5 H); 3.41 to 3.47 (m, 4 H); 4.35 to 4.44 (m, 1 H); 4.89 (m, 1 H); 5.02 (s, 1 H); 7.24 to 7.33 (m, 2 H); 7.36 to 7.45 (m, 1 H); 7.51 (m, 1 H).

Mass spectrometry: method A
Retention time Tr (min)=0.83
[M+H]+: m/z 399.

EXAMPLE 16

(8S)-9-[(1R or 1S)-1-(3-fluorophenyl)ethyl]-2-(morpholin-4-yl)-8-(trifluoromethyl)-6,7,8,9-tetrahydro-4H-pyrimido[1,2-a]pyrimidin-4-one

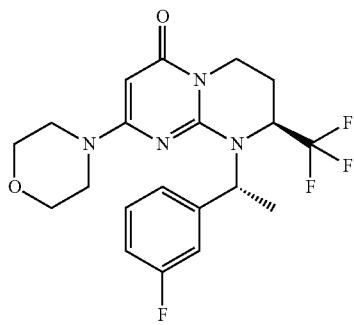 [SMILES: C[C@H](c1cccc(F)c1)N1c2nc(N3CCOCC3)cc(=O)n2CC[C@H]1C(F)(F)F]

Stage b:

In a round-bottomed flask, a mixture of 300 mg of (S)-2-chloro-1-[1-(3-fluorophenyl)ethyl]-8-trifluoromethyl-1,6,7,8-tetrahydropyrimido[1,2-a]pyrimidin-4-one and 3 ml of morpholine is heated at 80° C. for 30 minutes. After cooling, the reaction mixture is concentrated under reduced pressure. The residue is taken up with ethyl acetate and water. The organic phase is separated and then dried over magnesium sulphate, filtered, and concentrated under reduced pressure. After purification by silica chromatography (eluent: $CH_2Cl_2$/MeOH 97.5/2.5), 152 mg of (8S)-9-[(1-(3-fluorophenyl)ethyl]-2-(morpholin-4-yl)-8-(trifluoromethyl)-6,7,8,9-tetrahydro-4H-pyrimido[1,2-a]pyrimidin-4-one are obtained, in the form of a single diastereoisomer (undetermined configuration on the phenethyl chain), the characteristics of which are the following:

1H NMR spectrum:
1.66 (d, J=7.0 Hz, 3 H); 1.80 to 1.95 (m, 1 H); 2.33 to 2.41 (m, 1 H); 3.09 to 3.28 (m, 5 H); 3.40 to 3.52 (m, 4 H); 4.06 to 4.16 (m, 1 H); 4.56 (m, 1 H); 4.95 (s, 1 H); 5.51 (q, J=7.0 Hz, 1 H); 7.00 to 7.17 (m, 3 H); 7.33 to 7.42 (m, 1 H).

Mass spectrometry: method A
Retention time Tr (min)=0.94
[M+H]+: m/z 427.

Stage a:

In a round-bottomed flask, 400 mg of (S)-2-chloro-8-trifluoromethyl-6,7,8,9-tetrahydropyrimido[1,2-a]pyrimidin-4-one (Example 1d) are introduced into 20 ml of tetrahydrofuran, 1.6 g of resin-supported triphenylphosphine (3 mmol/g) and 663 mg of 1-(3-fluorophenyl)ethanol. The reaction mixture is then stirred at ambient temperature for 5 minutes, before the addition of 0.790 ml of diethyl azodicarboxylate. After stirring for 1 hour at ambient temperature, the reaction mixture is filtered and the filtrate is concentrated under reduced pressure.

The residue is taken up with ethyl acetate and water. The organic phase is separated and then dried over magnesium sulphate, filtered, and concentrated under reduced pressure. After purification by silica chromatography (eluent: $CH_2Cl_2$/EtOAc 96/04), 150 mg of (S)-2-chloro-1-[1-(3-fluorophenyl)ethyl]-8-trifluoromethyl-1,6,7,8-tetrahydropyrimido[1,2-a]pyrimidin-4-one are obtained, in the form of a single diastereoisomer (undetermined configuration on the phenethyl chain), the characteristics of which are the following:

Mass spectrometry: method A
Retention time Tr (min)=1.11
[M+H]+: m/z 376; [M−H]−: m/z 253 (base peak).

EXAMPLE 17

(8S)-9-(4-fluorobenzyl)-2-(morpholin-4-yl)-8-(trifluoromethyl)-6,7,8,9-tetrahydro-4H-pyrimido[1,2-a]pyrimidin-4-one

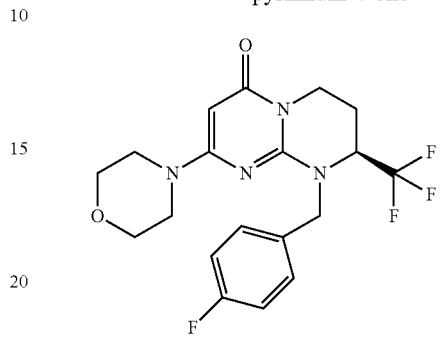

0.536 g of caesium carbonate and 0.44 ml of 1-(bromomethyl)-4-fluorobenzene are added, under an argon atmosphere, to a solution of 300 mg of (S)-2-morpholin-4-yl-8-trifluoromethyl-6,7,8,9-tetrahydro-pyrimido[1,2-a]pyrimidin-4-one (Example 1e) in 3 ml of acetonitrile. The resulting mixture is then heated at 80° C. for 2 hours. The reaction mixture is then evaporated under reduced pressure and the residue obtained is then purified by silica chromatography (eluent: $CH_2Cl_2$/MeOH 98/02) so as to give 61 mg of (8S)-9-(4-fluorobenzyl)-2-(morpholin-4-yl)-8-(trifluoromethyl)-6,7,8,9-tetrahydro-4H-pyrimido[1,2-a]pyrimidin-4-one, in the form of a white solid, the characteristics of which are the following:

1H NMR spectrum:
2.09 to 2.25 (m, 1 H); 2.34 to 2.44 (m, 1 H); 3.18 to 3.32 (m, 5 H); 3.41 to 3.53 (m, 4 H); 4.21 (m, 1 H); 4.51 (d, J=15.2 Hz, 1 H); 4.60 to 4.72 (m, 1 H); 4.96 (s, 1 H); 5.17 (d, J=15.2 Hz, 1 H); 7.13 (t, J=8.7 Hz, 2 H); 7.30 (dd, J=5.4 and 8.7 Hz, 2 H).

Mass spectrometry: method A
Retention time Tr (min)=0.89
[M+H]+: m/z 413.

EXAMPLE 18

(S)-9-Benzoyl-2-morpholin-4-yl-8-trifluoromethyl-6,7,8,9-tetrahydropyrimido[1,2-a]pyrimidin-4-one

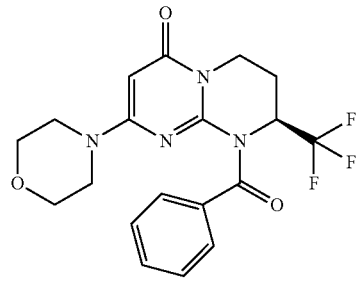 [SMILES: O=C(c1ccccc1)N1c2nc(N3CCOCC3)cc(=O)n2CC[C@H]1C(F)(F)F]

35.7 mg of sodium hydride and then, after 10 minutes of stirring, 0.135 ml de of benzoyl chloride are added, under an argon atmosphere, to a solution of 300 mg of (S)-2-morpholin-4-yl-8-trifluoromethyl-6,7,8,9-tetrahydropyrimido[1,2-a]pyrimidin-4-one (Example 1e) in 3 ml of tetrahydrofuran.

After stirring for six hours at ambient temperature, a saturated solution of sodium bicarbonate and ethyl acetate are added to the reaction mixture. The organic phase is separated and then successively washed with a saturated solution of sodium chloride, dried over magnesium sulphate, filtered and concentrated under reduced pressure. The residue obtained is purified by silica chromatography (eluent: $CH_2Cl_2$) so as to give 74 mg of (S)-9-benzoyl-2-morpholin-4-yl-8-trifluoromethyl-6,7,8,9-tetrahydropyrimido[1,2-a]pyrimidin-4-one, in the form of a white solid, the characteristics of which are the following:

1H NMR spectrum:

2.20 to 2.31 (m, 1 H); 2.68 to 2.82 (m, 3 H); 2.86 to 2.96 (m, 2 H); 3.15 to 3.44 (m partially masked, 4 H); 3.75 to 3.87 (m, 1 H); 4.17 to 4.30 (m, 1 H); 5.15 (s, 1 H); 5.38 to 5.53 (m, 1 H); 7.37 to 7.43 (m, 2 H); 7.45 to 7.53 (m, 3 H).

Mass spectrometry: method B

Retention time Tr (min)=3.59

[M+H]+: m/z 409

Optical rotation: OR=−15.8+/−0.8; C=1.650 mg/0.5 ml DMSO.

EXAMPLE 19

(S)-2-morpholin-4-yl-9-pyridin-3-yl-8-trifluoromethyl-6,7,8,9-tetrahydropyrimido[1,2-a]pyrimidin-4-one

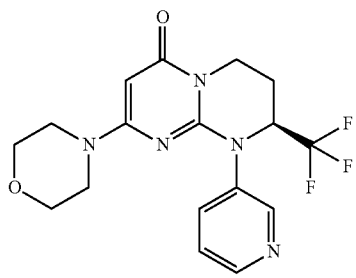 [SMILES: O=c1cc(N2CCOCC2)nc2n1CC[C@@H](C(F)(F)F)N2c1cccnc1]

The product is prepared according to the procedure described in Example 12, using 200 mg of (S)-2-morpholin-4-yl-8-trifluoromethyl-6,7,8,9-tetrahydropyrimido[1,2-a]pyrimidin-4-one (Example 1e) and 380 mg of 3-iodopyridine. After purification by silica chromatography (elution gradient of $CH_2Cl_2$ to $CH_2Cl_2$/MeOH 96/04), 48 mg of (S)-2-morpholin-4-yl-9-pyridin-3-yl-8-trifluoromethyl-6,7,8,9-tetrahydropyrimido[1,2-a]pyrimidin-4-one are obtained, in the form of a yellow solid, the characteristics of which are the following:

1H NMR spectrum:

2.44 to 2.48 (m, 2 H); 3.00 to 3.13 (m, 4 H); 3.31 to 3.37 (m, 1 H); 3.41 to 3.47 (m, 4 H); 4.37 (d, J=16.1 Hz, 1 H); 4.97 to 5.09 (m, 2 H); 7.48 (dd, J=4.9 and 8.3 Hz, 1 H); 7.80 to 7.85 (m, 1 H); 8.50 (dd, J=1.4 and 4.9 Hz, 1 H); 8.57 (d, J=2.2 Hz, 1 H).

Mass spectrometry: method A

Retention time Tr (min)=0.55

[M+H]+: m/z 382

Optical rotation: OR=−40+/−1.6, C=0.2% in DMSO.

EXAMPLE 20

(S)-2-morpholin-4-yl-9-pyridin-4-yl-8-trifluoromethyl-6,7,8,9-tetrahydropyrimido[1,2-a]pyrimidin-4-one

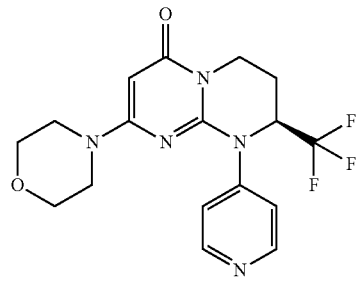 [SMILES: O=c1cc(N2CCOCC2)nc2n1CC[C@@H](C(F)(F)F)N2c1ccncc1]

The product is prepared according to the procedure described in Example 12, using 200 mg of (S)-2-morpholin-4-yl-8-trifluoromethyl-6,7,8,9-tetrahydropyrimido[1,2-a]pyrimidin-4-one (Example 1e) and 380 mg of 4-iodopyridine. After purification by silica chromatography (elution gradient from $CH_2Cl_2$ to $CH_2Cl_2$/MeOH 96/04), 26 mg of (S)-2-morpholin-4-yl-9-pyridin-4-yl-8-trifluoromethyl-6,7,8,9-tetrahydropyrimido[1,2-a]pyrimidin-4-one are obtained, in the form of a yellow solid, the characteristics of which are the following:

1H NMR spectrum:

2.43 to 2.48 (m, 2 H); 3.07 to 3.19 (m, 4 H); 3.33 to 3.39 (m, 1 H); 3.45 to 3.50 (m, 4 H); 4.30 to 4.38 (m, 1 H); 5.06 (s, 1 H); 5.09 to 5.17 (m, 1 H); 7.45 (d, J=6.1 Hz, 2 H); 8.62 (d, J=6.1 Hz, 2 H).

Mass spectrometry: method A

[M+H]+: m/z 382; [M−H]−: m/z 380

Retention time Tr (min)=0.42

Optical rotation: OR=−31 +/−1.3, C=0.2% in DMSO.

EXAMPLE 21

(8S)-9-(4-methylphenyl)-2-(morpholin-4-yl)-8-(trifluoro-methyl)-6,7,8,9-tetrahydro-4H-pyrimido[1,2-a]pyrimidin-4-one

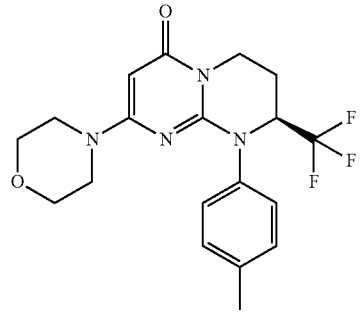 [SMILES: Cc1ccc(N2c3nc(N4CCOCC4)cc(=O)n3CC[C@H]2C(F)(F)F)cc1]

The product is prepared according to the procedure described in Example 12, using 100 mg of (8S)-2-morpholin-4-yl-8-trifluoromethyl-6,7,8,9-tetrahydropyrimido[1,2-a]pyrimidin-4-one (Example 1e) and 100 mg of 1-iodo-4-methylbenzene. After purification by silica chromatography (eluent: $CH_2Cl_2$/MeOH 98/02), 23 mg of (8S)-9-(4-methylphenyl)-2-(morpholin-4-yl)-8-(trifluoromethyl)-6,7,8,9- tetrahydro-4H-pyrimido[1,2-a]pyrimidin-4-one are obtained in the form of a cream solid, the characteristics of which are the following:

¹H NMR spectrum:
2.32 (s, 3 H); 2.44 (m, 2 H); 2.97 to 3.15 (m, 4 H); 3.33 to 3.50 (m partially masked, 5 H); 4.34 (m, 1 H); 4.86 (m, 1 H); 4.98 (s, 1 H); 7.22 (s, 4 H).

Mass spectrometry: method A
Retention time Tr (min)=0.90
[M+H]+: m/z 395.

EXAMPLE 22

(8S)-9-(2-chlorobenzyl)-2-(morpholin-4-yl)-8-(trifluoro-methyl)-6,7,8,9-tetrahydro-4H-pyrimido[1,2-a]pyrimidin-4-one

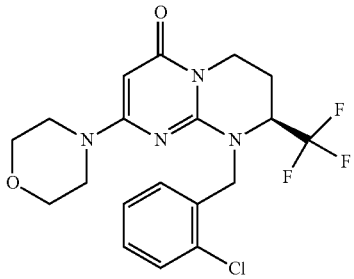 [SMILES: O=c1cc(N2CCOCC2)nc2n1CC[C@@H](C(F)(F)F)N2Cc1ccccc1Cl]

214 mg of caesium carbonate and 74 mg of 1-(bromomethyl)-2-chlorobenzene are added to a solution of 100 mg of (8S)-2-(morpholin-4-yl)-8-(trifluoromethyl)-6,7,8,9-tetrahydro-4H-pyrimido[1,2-a]pyrimidin-4-one (Example 1e) in 2 ml of dimethylformamide. After 16 hours at a temperature in the region of 20° C., the reaction medium is run into water. The organic phase is separated and the aqueous phase is extracted with ethyl acetate. The combined organic phases are concentrated to dryness under reduced pressure. The residue is purified by preparative HPLC/MS (Method C). After evaporation of the acetonitrile and lyophilization, 94 mg of (8S)-9-(2-chloro-benzyl)-2-(morpholin-4-yl)-8-(trifluoromethyl)-6,7,8,9-tetrahydro-4H-pyrimido[1,2-a]pyrimidin-4-one are obtained in the form of an oil, the characteristics of which are the following:

¹H NMR spectrum:
2.29 to 2.66 (m, 2 H); 3.09 to 3.18 (m, 4 H); 3.23 to 3.50 (m partially masked, 5 H); 4.27 (m, 1 H); 4.68 (d, J=16.6 Hz, 1 H); 4.74 (m, 1 H); 4.96 (s, 1 H); 5.12 (d, J=16.6 Hz, 1 H); 7.16 to 7.22 (m, 1 H); 7.24 to 7.32 (m, 2 H); 7.41 to 7.48 (m, 1 H).

Mass spectrometry: method A
Retention time Tr (min)=0.96
[M+H]+: m/z 429.

EXAMPLE 23

(8S)-9-(3-fluorobenzyl)-2-(morpholin-4-yl)-8-(trifluoromethyl)-6,7,8,9-tetrahydro-4H-pyrimido[1,2-a]pyrimidin-4-one

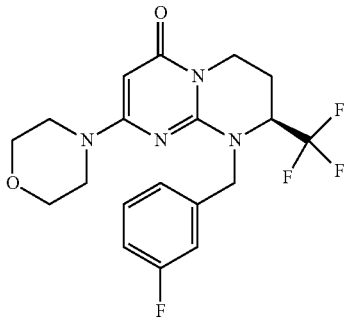 [SMILES: O=c1cc(N2CCOCC2)nc2n1CC[C@@H](C(F)(F)F)N2Cc1cccc(F)c1]

The product is prepared according to the procedure described in Example 22, using 100 mg of (8S)-2-(morpholin-4-yl)-8-(trifluoromethyl)-6,7,8,9-tetrahydro-4H-pyrimido[1,2-a]pyrimidin-4-one, 214 mg of caesium carbonate and 68 mg of 1-(bromomethyl)-3-fluorobenzene. After purification by preparative HPLC/MS (Method C), 102 mg of (8S)-9-(3-fluorobenzyl)-2-(morpholin-4-yl)-8-(trifluoromethyl)-6,7,8,9-tetrahydro-4H-pyrimido[1,2-a]-pyrimidin-4-one are obtained in the form of an oil, the characteristics of which are the following:

¹H NMR spectrum:
2.17 to 2.45 (m, 2 H); 3.15 to 3.31 (m, 5 H); 3.39 to 3.49 (m, 4 H); 4.23 (m, 1 H); 4.58 (d, J=16.1 Hz, 1 H); 4.66 to 4.78 (m, 1 H); 4.97 (s, 1 H); 5.13 (d, J=16.1 Hz, 1 H); 6.98 to 7.15 (m, 3 H); 7.35 (dt, J=6.0 and 8.1 Hz, 1 H)

Mass spectrometry: method A
Retention time Tr (min)=0.89
[M+H]+: m/z 413.

EXAMPLE 24

(8S)-9-[2-(2-methoxyphenyl)ethyl]-2-(morpholin-4-yl)-8-(trifluoromethyl)-6,7,8,9-tetrahydro-4H-pyrimido[1,2-a]pyrimidin-4-one

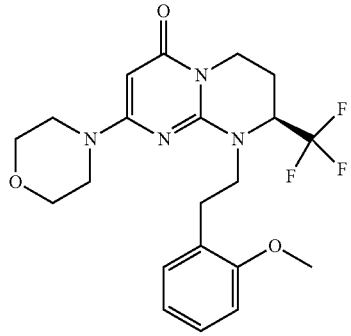 [SMILES: COc1ccccc1CCN1c2nc(N3CCOCC3)cc(=O)n2CC[C@H]1C(F)(F)F]

214 mg of caesium carbonate and 78 mg of 1-(2-bromoethyl)-3-methoxybenzene are added to a solution of 100 mg of (8S)-2-(morpholin-4-yl)-8-(trifluoromethyl)-6,7,8,9-tetrahydro-4H-pyrimido[1,2-a]pyrimidin-4-one (Example 1e) in 2 ml of dimethylformamide. After 18 hours at a temperature of 60° C., 78 mg of 1-(2-bromoethyl)-3-fluorobenzene are added. After 2 hours at a temperature of 60° C., the reaction mixture obtained is run into water. The organic phase is separated and the aqueous phase is extracted with ethyl acetate. The combined organic phases are concentrated to dryness under reduced pressure. The residue is purified by preparative HPLC/MS (Method C). After evaporation of the acetonitrile and lyophilization, 25 mg of (8S)-9-[2-(2-methoxyphenyl)ethyl]-2-(morpholin-4-yl)-8-(trifluoromethyl)-6,7,8,9-tetra-hydro-4H-pyrimido[1,2-a]pyrimidin-4-one are obtained in the form of an oil, the characteristics of which are the following:

¹H NMR spectrum:
1.84 to 2.00 (m, 1 H); 2.25 to 2.35 (m, 1 H); 2.83 to 3.03 (m, 2 H); 3.06 to 3.30 (m, 2 H); 3.44 (m, 4 H); 3.61 to 3.67 (m, 4 H); 3.76 (s, 3H); 4.08 to 4.24 (m, 2H); 4.37 to 4.52 (m, 1H); 4.99 (s, 1H); 6.88 (dt, J=0.9 and 7.6Hz, 1 H); 6.96 (broad d, J=7.9 Hz, 1 H); 7.14 (dd, J=1.5 and 7.6Hz, 1H); 7.18 to 7.26 (m, 1 H)

Mass spectrometry: method A
Retention time Tr (min)=0.98
[M+H]+: m/z 439.

EXAMPLE 25

(8S)-9-[2-(3-methoxyphenyl)ethyl]-2-(morpholin-4-O-8-(trifluoromethyl)-6,7,8,9-tetrahydro-4H-pyrimido[1,2-a]pyrimidin-4-one

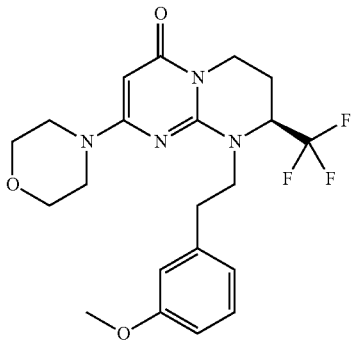 [SMILES: COc1cccc(CCN2c3nc(N4CCOCC4)cc(=O)n3CC[C@H]2C(F)(F)F)c1]

The product is prepared according to the procedure described in Example 24, but using 100 mg of (8S)-2-(morpholin-4-yl)-8-(trifluoromethyl)-6,7,8,9-tetrahydro-4H-pyrimido[1,2-a]pyrimidin-4-one, 78 mg of 1-(2-bromo-ethyl)-3-methoxybenzene and 214 mg of caesium carbonate in 2 ml of dimethylformamide. After reaction for 3 days at a temperature of 60° C., treatment as described in Example 24 and purification by preparative HPLC/MS (Method C), 20 mg of (8S)-9-[2-(3-methoxyphenyl)ethyl]-2-(morpholin-4-yl)-8-(trifluoromethyl)-6,7,8,9-tetrahydro-4H-pyrimido[1,2-a]pyrimidin-4-one are obtained in the form of an oil, the characteristics of which are the following:

$^1$H NMR spectrum:

1.88 to 2.01 (m, 1 H); 2.32 (m, 1 H); 2.74 to 2.90 (m, 1 H); 2.96 (m, 1 H); 3.10 to 3.22 (m, 1 H); 3.26 to 3.39 (m partially masked, 1H); 3.43 to 3.48 (m, 4 H); 3.62 to 3.68 (m, 4 H); 3.73 (s, 3 H); 4.02 to 4.23 (m, 2H); 4.49 to 4.65 (m, 1 H); 5.00 (s, 1 H); 6.70 to 6.88 (m, 3 H); 7.14 to 7.26 (m, 1 H)

Mass spectrometry: method A
Retention time Tr (min)=0.94
[M+H]+: m/z 439.

EXAMPLE 26

(8S)-9-(3-methoxybenzyl)-2-(morpholin-4-yl)-8-(trifluoromethyl)-6,7,8,9-tetrahydro-4H-pyrimido[1,2-a]pyrimidin-4-one

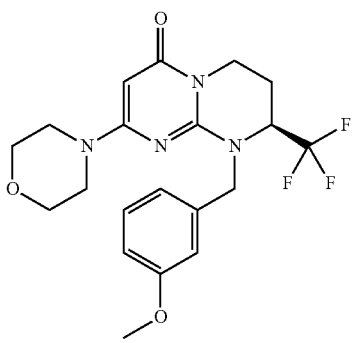 [SMILES: COc1cccc(CN2c3nc(N4CCOCC4)cc(=O)n3CC[C@H]2C(F)(F)F)c1]

The product is prepared according to the procedure described in Example 22, but using 100 mg of (8S)-2-(morpholin-4-yl)-8-(trifluoromethyl)-6,7,8,9-tetrahydro-4H-pyrimido[1,2-a]pyrimidin-4-one, 57 mg of 1-(chloro-methyl)-3-methoxybenzene and 214 mg of caesium carbonate in 2 ml of dimethylformamide. After treatment, the residue is stirred into acetonitrile. The solid is spin-filter-dried, rinsed with diethyl ether and then dried under a vacuum bell jar. 111 mg of (8S)-9-(3-methoxybenzyl)-2-(morpholin-4-yl)-8-(trifluoromethyl)-6,7,8,9-tetrahydro-4H-pyrimido[1,2-a]pyrimidin-4-one are thus obtained in the form of a white solid, the characteristics of which are the following:

$^1$H NMR spectrum:

2.07 to 2.23 (m, 1 H); 2.35 to 2.44 (m, 1 H); 3.19 to 3.28 (m, 5 H); 3.40 to 3.55 (m, 4 H); 3.72 (s, 3 H); 4.22 (m, 1 H); 4.45 (d, J=15.9 Hz, 1 H); 4.56 to 4.70 (m, 1 H); 4.96 (s, 1 H); 5.21 (d, J=15.9 Hz, 1H); 6.75 to 6.88 (m, 3 H); 7.19 to 7.27 (m, 1 H)

Mass spectrometry: method A
Retention time Tr (min)=0.88
[M+H]+: m/z 425.

EXAMPLE 27

(8S)-9-(4-methoxyphenyl)-2-(morpholin-4-yl)-8-(trifluoromethyl)-6,7,8,9-tetrahydro-4H-pyrimido[1,2-a]pyrimidin-4-one

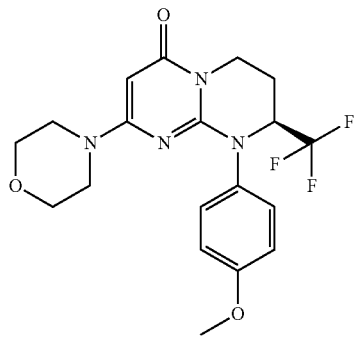

The product is prepared according to the procedure described in Example 12, using 100 mg of (8S)-2-morpholin-4-yl-8-trifluoromethyl-6,7,8,9-tetrahydropyrimido[1,2-a]pyrimidin-4-one (Example 1e), 108 mg of 1-iodo-4-methoxybenzene and 79 mg of 4,7-dimethoxy-1,10-phenanthroline. After purification by silica chromatography (eluent: CH$_2$Cl$_2$/MeOH 98/02), 31 mg of (8S)-9-(4-methoxyphenyl)-2-(morpholin-4-yl)-8-(trifluoromethyl)-6,7,8,9-tetrahydro-4H-pyrimido[1,2-a]pyrimidin-4-one are obtained in the form of a cream foam, the characteristics of which are the following:

$^1$H NMR spectrum:

2.38 to 2.46 (m, 2H); 3.04 to 3.15 (m, 4H); 3.20 to 3.35 (m partially masked, 1H); 3.45 (m, 4H); 3.77 (s, 3H); 4.34 (m, 1H); 4.83 (m, 1H); 4.98 (s, 1H); 6.95 (d, J=8.8Hz, 2H); 7.25 (d, J=8.8Hz, 2H)

Mass spectrometry: method A
Retention time Tr (min)=0.83
[M+H]+: m/z 411.

EXAMPLE 28

(8S)-9-[(2-fluorophenyl)carbonyl]-2-(morpholin-4-yl)-8-(trifluoromethyl)-6,7,8,9-tetrahydro-4H-pyrimido[1,2-a]pyrimidin-4-one

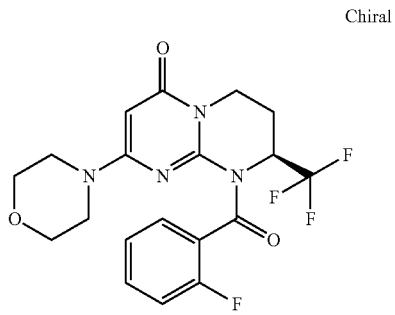 [SMILES: O=C(c1ccccc1F)N1c2nc(N3CCOCC3)cc(=O)n2CC[C@H]1C(F)(F)F]

Chiral

The product is prepared according to the procedure described in Example 18, using 300 mg of (8S)-2-morpholin-4-yl-8-trifluoromethyl-6,7,8,9-tetrahydropyrimido[1,2-a]pyrimidin-4-one (Example 1e), 47 mg of sodium hydride and 156 mg of 2-fluorobenzoyl chloride in 5 ml of tetrahydrofuran. After purification by silica chromatography (eluent: CH$_2$Cl$_2$/MeOH 98/02), 35 mg of (8S)-9-[(2-fluorophenyl)carbonyl]-2-(morpholin-4-yl)-8-(trifluoro-methyl)-6,7,8,9-tetrahydro-4H-pyrimido[1,2-a]pyrimidin-4-one are obtained in the form of a white foam, the characteristics of which are the following:

$^1$H NMR spectrum:

2.13 to 2.26 (m, 1 H); 2.65 to 2.85 (m, 3 H); 2.94 to 3.02 (m, 2 H); 3.20 to 3.40 (m partially masked, 4 H); 3.43 to 3.55 (m, 1 H); 4.42 (m, 1 H); 5.19 (s, 1 H); 5.55 to 5.69 (m, 1 H); 7.18 to 7.31 (m, 2 H); 7.49 to 7.64 (m, 2 H)

Mass spectrometry: method A

Retention time Tr (min)=0.79

[M+H]+: m/z 427.

EXAMPLE 29

(8S)-9-(3,5-difluorobenzyl)-2-(morpholin-4-yl)-8-(trifluoro-methyl)-6,7,8,9-tetrahydro-4H-pyrimido[1,2-a]pyrimidin-4-one

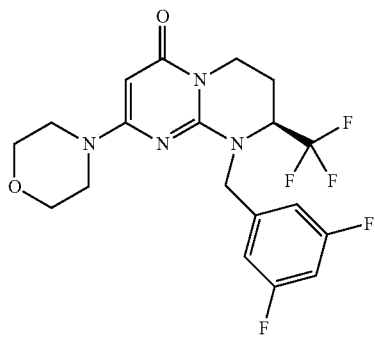 [SMILES: O=c1cc(N2CCOCC2)nc2n1CC[C@@H](C(F)(F)F)N2Cc1cc(F)cc(F)c1]

The product is prepared according to the procedure described in Example 22, using 100 mg of (8S)-2-morpholin-4-yl-8-trifluoromethyl-6,7,8,9-tetrahydropyrimido[1,2-a]pyrimidin-4-one (Example 1e), 214 mg of caesium carbonate and 75 mg of 1-(bromomethyl)-3,5-difluorobenzene in 2 ml of dimethylformamide. After purification by preparative HPLC/MS (Method C), 85 mg of (8S)-9-(3,5-difluorobenzyl)-2-(morpholin-4-yl)-8-(trifluoromethyl)-6,7,8,9-tetrahydro-4H-pyrimido[1,2-a]pyrimidin-4-one are obtained in the form of an oil, the characteristics of which are the following:

$^1$H NMR spectrum:

2.21 to 2.44 (m, 2 H); 3.14 to 3.33 (m, 5 H); 3.36 to 3.52 (m, 4 H); 4.23 (m, 1 H); 4.61 (d, J=16.4Hz, 1 H); 4.68 to 4.81 (m, 1H); 4.98 (s, 1H); 5.07 (d, J=16.4Hz, 1 H); 6.90 to 7.02 (m, 2 H); 7.07 (tt, J=2.3 and 9.3 Hz, 1 H)

Mass spectrometry: method B

Retention time Tr (min)=3.93

[M+H]+: m/z 431.

EXAMPLE 30

(8S)-9-(2,4-difluorobenzyl)-2-(morpholin-4-yl)-8-(trifluoro-methyl)-6,7,8,9-tetrahydro-4H-pyrimido[1,2-a]pyrimidin-4-one

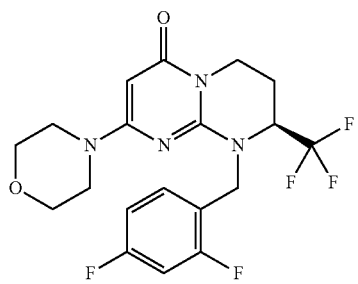 [SMILES: O=c1cc(N2CCOCC2)nc2n1CC[C@@H](C(F)(F)F)N2Cc1ccc(F)cc1F]

The product is prepared according to the procedure described in Example 22, using 100 mg of (8S)-2-morpholin-4-yl-8-trifluoromethyl-6,7,8,9-tetrahydropyrimido[1,2-a]pyrimidin-4-one (Example 1e), 214 mg of caesium carbonate and 75 mg of 1-(bromomethyl)-2,4-difluorobenzene in 2 ml of dimethylformamide. After purification by preparative HPLC/MS (Method C), 86 mg of (8S)-9-(2,4-difluorobenzyl)-2-(morpholin-4-yl)-8-(trifluoromethyl)-6,7,8,9-tetrahydro-4H-pyrimido[1,2-a]pyrimidin-4-one are obtained in the form of an oil, the characteristics of which are the following:

$^1$H NMR spectrum:

2.16 to 2.30 (m, 1 H); 2.35 to 2.45 (m, 1 H); 3.17 to 3.32 (m, 5 H); 3.41 to 3.49 (m, 4 H); 4.22 (dd, J=5.9 and 14.2Hz, 1 H); 4.60 (d, J=16.1 Hz, 1 H); 4.66 to 4.76 (m, 1 H); 4.97 (s, 1 H); 5.11 (d, J=16.1 Hz, 1 H); 7.03 (ddt, J=1.1-2.6 and 9.0 Hz, 1 H); 7.22 (ddd, J=2.6-9.0 and 10.9 Hz, 1 H); 7.30 (dt, J=6.7 and 9.0 Hz, 1 H)

Mass spectrometry: method B

Retention time Tr (min)=3.96

[M+H]+: m/z 431.

EXAMPLE 31

(8S)-2-(morpholin-4-yl)-9-(2,3,4-trifluorobenzyl)-8-(trifluoro-methyl)-6,7,8,9-tetrahydro-4H-pyrimido[1,2-a]pyrimidin-4-one

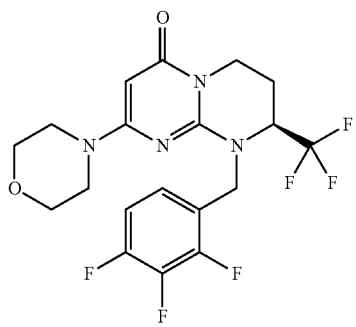 [SMILES: O=c1cc(N2CCOCC2)nc2n1CC[C@@H](C(F)(F)F)N2Cc1ccc(F)c(F)c1F]

The product is prepared according to the procedure described in Example 22, using 100 mg of (8S)-2-morpholin-4-yl-8-trifluoromethyl-6,7,8,9-tetrahydropyrimido[1,2-a]pyrimidin-4-one (Example 1e), 214 mg of caesium carbonate and 82 mg of 1-(bromomethyl)-2,3,4-trifluorobenzene in 2 ml of dimethylformamide. After purification by preparative HPLC/MS (Method C), 76 mg of (8S)-2-(morpholin-4-yl)-9-(2,3,4-trifluorobenzyl)-8-(trifluoromethyl)-6,7,8,9-tetrahydro-4H-pyrimido[1,2-a]pyrimidin-4-one are obtained in the form of an oil, the characteristics of which are the following:

$^1$H NMR spectrum: 1H
2.15 to 2.31 (m, 1 H); 2.35 to 2.44 (m, 1 H); 3.18 to 3.32 (m, 5 H); 3.42 to 3.54 (m, 4 H); 4.22 (dd, J=5.5 and 14.3 Hz, 1 H); 4.65 (d, J=16.1 Hz, 1 H); 4.73 (m, 1 H); 4.98 (s, 1 H); 5.16 (d, J=16.1 Hz, 1H); 7.05 to 7.17 (m, 1 H); 7.20 to 7.32 (m, 1 H)

Mass spectrometry: method B
Retention time Tr (min)=4.08
[M+11]+: m/z 449.

EXAMPLE 32

(8S)-9-[(5-chloro-1-benzothiophen-3-yl)methyl]-2-(morpholin-4-yl)-8-(trifluoromethyl)-6,7,8,9-tetrahydro-4H-pyrimido[1,2-a]pyrimidin-4-one

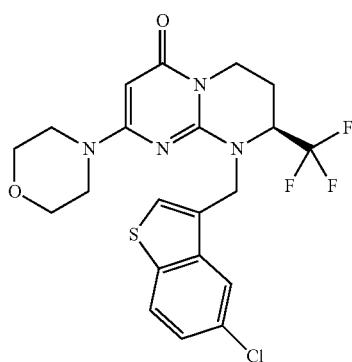 [SMILES: O=c1cc(N2CCOCC2)nc2n1CC[C@@H](C(F)(F)F)N2Cc1csc2ccc(Cl)cc12]

The product is prepared according to the procedure described in Example 22, using 100 mg of (8S)-2-morpholin-4-yl-8-trifluoromethyl-6,7,8,9-tetrahydropyrimido[1,2-a]pyrimidin-4-one (Example 1e), 214 mg of caesium carbonate and 95 mg of 3-(bromomethyl)-5-chloro-1-benzothiophene in 2 ml of dimethylformamide. After purification by preparative HPLC/MS (Method C), 72 mg of (8S)-9-[(5-chloro-1-benzothiophen-3-yl)methyl]-2-(morpholin-4-yl)-8-(trifluoromethyl)-6,7,8,9-tetrahydro-4H-pyrimido[1,2-a]pyrimidin-4-one are obtained in the form of an oil, the characteristics of which are the following:

$^1$H NMR spectrum:
2.13 to 2.25 (m, 1 H); 2.34 to 2.43 (m, 1 H); 3.16 to 3.32 (m, 5 H); 3.35 to 3.48 (m, 4 H); 4.21 (dd, J=6.0 and 14.3 Hz, 1 H); 4.62 to 4.74 (m, 2 H); 5.00 (s, 1 H); 5.52 (d, J=16.1 Hz, 1 H); 7.42 (dd, J=2.0 and 8.6 Hz, 1 H); 7.67 (s, 1 H); 8.01 (d, J=2.0 Hz, 1 H); 8.03 (d, J=8.6 Hz, 1 H)

Mass spectrometry: method B
Retention time Tr (min)=4.42
[M+H]+: m/z 485.

EXAMPLE 33

(8S)-9-[(1R or 1S)-1-(4-fluorophenyl)ethyl]-2-(morpholin-4-yl)-8-(trifluoromethyl)-6,7,8,9-tetrahydro-4H-pyrimido[1,2-a]pyrimidin-4-one

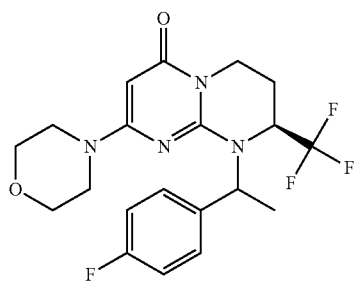 [SMILES: CC(c1ccc(F)cc1)N1c2nc(N3CCOCC3)cc(=O)n2CC[C@H]1C(F)(F)F]

Stage a:

The two diastereoisomers of (8S)-9-[(1R and 1S)-1-(4-fluoro-phenyl)ethyl]-2-(morpholin-4-yl)-8-(trifluoromethyl)-6,7,8,9-tetrahydro-4H-pyrimido[1,2-a]pyrimidin-4-one are separated by chiral chromatography: Chiralpak IC 20 µm column; elution: 70% heptane 30% EtOH, using 130 mg of a 70/30 mixture of the two diastereoisomers.

The first diastereoisomer is concentrated so as to obtain 42 mg of (8S)-9-[(1R or 1S)-1-(4-fluorophenyl)ethyl]-2-(morpholin-4-yl)-8-(trifluoro-methyl)-6,7,8,9-tetrahydro-4H-pyrimido[1,2-a]pyrimidin-4-one in the form of a colourless solid, the characteristics of which are the following:

$^1$H NMR spectrum (400 MHz):
1.72 (d, J=6.8 Hz, 3 H); 2.22 (m, 1 H); 2.43 (m, 1 H); 3.14 to 3.27 (m, 5 H); 3.39 to 3.54 (m, 4 H); 4.13 (dd, J=5.6 and 14.4 Hz, 1 H); 4.80 to 4.88 (m, 1 H); 4.93 (s, 1 H); 5.43 (q, J=6.8 Hz, 1 H); 7.12 (t, J=8.8 Hz, 2 H); 7.36 (dd, J=5.6 and 8.8 Hz, 2 H)

Mass spectrometry: method A
Retention time Tr (min)=0.95
[M+H]+: m/z 427.

Stage b (8S)-9-[(1R and 1S)-1-(4-fluorophenyl)
ethyl]-2-(morpholin-4-yl)-8-(trifluoromethyl)-6,7,8,
9-tetrahydro-4H-pyrimido[1,2-a]pyrimidin-4-one

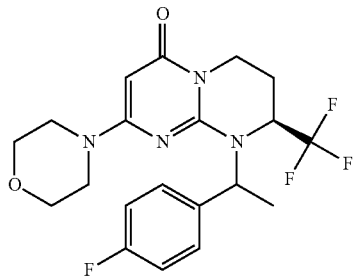 [SMILES: CC(c1ccc(F)cc1)N1c2nc(N3CCOCC3)cc(=O)n2CC[C@H]1C(F)(F)F]

The mixture of (8S)-9-[(1R and 1S)-1-(4-fluorophenyl)
ethyl]-2-(morpholin-4-yl)-8-(trifluoromethyl)-6,7,8,9-tetrahydro-4H-pyrimido[1,2-a]-pyrimidin-4-one is prepared according to the procedure described in Example 24, using 500 mg of (8S)-2-(morpholin-4-yl)-8-(trifluoromethyl)-6,7,8,9-tetrahydro-4H-pyrimido[1,2-a]pyrimidin-4-one, 1 g of caesium carbonate and 391 mg of 1-(1-chloroethyl)-4-fluorobenzene in 20 ml of acetonitrile. After purification by silica chromatography (eluent: CH$_2$Cl$_2$/MeOH 97/3), 130 mg of (8S)-9-[(1R and 1S)-1-(4-fluorophenyl)ethyl]-2-(morpholin-4-yl)-8-(trifluoro-methyl)-6,7,8,9-tetrahydro-4H-pyrimido[1,2-a]pyrimidin-4-one are obtained in the form of a 70/30 mixture of two diastereoisomers, the characteristics of which are the following:

$^1$H NMR spectrum:

It is a 70-30 mixture of two isomers, with: 1.65 (d, J=7.0 Hz, 2.1 H); 1.72 (d, J=7.0 Hz, 0.9 H); 1.75 to 1.86 (m, 0.7 H); 2.25 to 2.48 (m, 1.3 H); 3.12 to 3.27 (m, 5 H); 3.40 to 3.56 (m, 4 H); 4.00 to 4.22 (m, 1 H); 4.42 (m, 0.7 H); 4.80 to 4.87 (m, 0.3 H); 4.93 (s, 0.3 H); 4.96 (s, 0.7 H); 5.44 (q, J=7.0 Hz, 0.3 H); 5.65 (q, J=7.0 Hz, 0.7 H); 7.06 to 7.21 (m, 2 H); 7.32 to 7.40 (m, 2 H).

EXAMPLE 34

(8S)-9-[(1R or 1S)-1-(4-fluorophenyl)ethyl]-2-(morpholin-4-yl)-8-(trifluoromethyl)-6,7,8,9-tetrahydro-4H-pyrimido[1,2-a]pyrimidin-4-one The previous purification (Example 33, stage a) also results in 85 mg of (8S)-9-[(1R or 1S)-1-(4-fluorophenyl)ethyl]-2-(morpholin-4-yl)-8-(trifluoro-methyl)-6,7,8,9-tetrahydro-4H-pyrimido[1,2-a]pyrimidin-4-one in the form of a colourless solid, the characteristics of which are the following:

$^1$H NMR spectrum:

1.65 (d, J=7.0 Hz, 3 H); 1.69 to 1.86 (m, 1 H); 2.29 to 2.37 (m, 1 H); 3.14 to 3.28 (m, 5 H); 3.44 to 3.58 (m, 4 H); 4.08 (dd, J=5.9 and 14.7 Hz, 1 H); 4.42 (m, 1 H); 4.96 (s, 1 H); 5.64 (q, J=7.0 Hz, 1 H); 7.17 (t, J=8.8 Hz, 2 H); 7.35 (dd, J=5.6 and 8.8 Hz, 2 H)

Mass spectrometry: method A

Retention time Tr (min)=0.95

[M+H]+: m/z 427.

EXAMPLE 35

(8S)-9-(3-methylphenyl)-2-(morpholin-4-yl)-8-(trifluoro-methyl)-6,7,8,9-tetrahydro-4H-pyrimido[1,2-a]pyrimidin-4-one Chiral

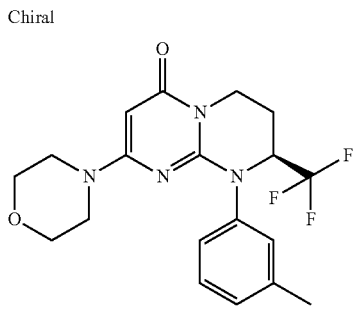 [SMILES: Cc1cccc(N2c3nc(N4CCOCC4)cc(=O)n3CC[C@H]2C(F)(F)F)c1]

The product is prepared according to the procedure described in Example 12, but using 250 mg of (8S)-2-morpholin-4-yl-8-trifluoromethyl-6,7,8,9-tetrahydropyrimido[1,2-a]pyrimidin-4-one (Example 1e) in 4 ml of dimethylformamide, 251 mg of 1-iodo-3-methylbenzene, 349 mg of tripotassium phosphate, 156 mg of copper iodide and 93 mg of (1S,2S)-cyclo-hexane-1,2-diamine. After 1 hour at 150° C. under microwave irradiation and silica column purification of the resulting reaction mixture (elution gradient of CH$_2$Cl$_2$ to CH$_2$Cl$_2$/MeOH 98/02), 195 mg of (8S)-9-(3-methylphenyl)-2-(morpholin-4-yl)-8-(trifluoromethyl)-6,7,8,9-tetrahydro-4H-pyrimido[1,2-a]-pyrimidin-4-one are obtained in the form of a green solid, the characteristics of which are the following:

$^1$H NMR spectrum:

2.31 (s, 3 H); 2.37 to 2.47 (m, 2 H); 3.02 to 3.16 (m, 4 H); 3.19 to 3.39 (m partially masked, 1 H); 3.40 to 3.53 (m, 4 H); 4.28 to 4.40 (m, 1 H); 4.93 (m, 1 H); 4.99 (s, 1 H); 7.13 (m, 2 H); 7.19 (broad s, 1 H); 7.29 (t, J=7.5 Hz, 1 H)

Mass spectrometry: method A

Retention time Tr (min)=0.90

[M+H]+: m/z 395.

EXAMPLE 36

(8S)-9-(4-chlorophenyl)-2-(morpholin-4-yl)-8-(trifluoro-methyl)-6,7,8,9-tetrahydro-4H-pyrimido[1,2-a]pyrimidin-4-one Chiral

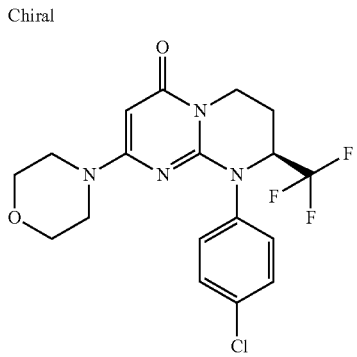 [SMILES: O=c1cc(N2CCOCC2)nc2n1CC[C@@H](C(F)(F)F)N2c1ccc(Cl)cc1]

The product is prepared according to the procedure described in Example 12, but using 250 mg of (8S)-2-morpholin-4-yl-8-trifluoromethyl-6,7,8,9-tetrahydropyrimido[1,2-a]pyrimidin-4-one (Example 1e), 274 mg of 1-chloro-4- iodobenzene, 349 mg of tripotassium phosphate, 156 mg of copper iodide and 93 mg of (1S,2S)-cyclohexane-1,2-diamine. After 1 hour at 150° C. under microwave irradiation and silica column purification of the resulting reaction mixture (elution gradient of CH$_2$Cl$_2$ to CH$_2$Cl$_2$/MeOH 98/02), 145 mg of (8S)-9-(4-chlorophenyl)-2-(morpholin-4-yl)-8-(trifluoromethyl)-6,7,8,9-tetrahydro-4H-pyrimido[1,2-a]pyrimidin-4-one are obtained in the form of a green foam, the characteristics of which are the following:

$^1$H NMR spectrum:

2.41 to 2.47 (m, 2 H); 3.07 to 3.12 (m, 4 H); 3.20 to 3.43 (m partially masked, 1 H); 3.46 (m, 4 H); 4.35 (m, 1 H); 4.94 (m, 1 H); 5.01 (s, 1 H); 7.39 (d, J=8.8Hz, 2 H); 7.49 (d, J=8.8Hz, 2 H)

Mass spectrometry: method A

Retention time Tr (min)=0.94;

[M+H]+: m/z 415.

EXAMPLE 37

(8S)-2-(morpholin-4-yl)-8-(trifluoromethyl)-9-[4-(trifluoro-methyl)phenyl]-6,7,8,9-tetrahydro-4H-pyrimido[1,2-a]pyrimidin-4-one

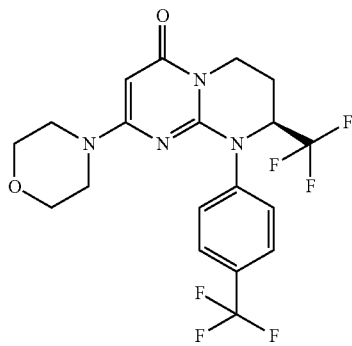 [SMILES: O=c1cc(N2CCOCC2)nc2n1CC[C@@H](C(F)(F)F)N2c1ccc(C(F)(F)F)cc1]

The product is prepared according to the procedure described in Example 12, but using 250 mg of (8S)-2-morpholin-4-yl-8-trifluoromethyl-6,7,8,9-tetrahydropyrimido[1,2-a]pyrimidin-4-one (Example 1e), 313 mg of 1-iodo-4-(trifluoromethyl)benzene, 349 mg of tripotassium phosphate, 156 mg of copper iodide and 93 mg of (1S,2S)-cyclohexane-1,2-diamine. After 1 hour at 150° C. under microwave irradiation and silica column purification of the resulting reaction mixture (elution gradient of CH$_2$Cl$_2$ to CH$_2$Cl$_2$/MeOH 98/02), 120 mg of (8S)-2-(morpholin-4-yl)-8-(trifluoromethyl)-9-[4-(trifluoromethyl)-phenyl]-6,7,8,9-tetrahydro-4H-pyrimido[1,2-a]pyrimidin-4-one are obtained in the form of a greenish solid, the characteristics of which are the following:

$^1$H NMR spectrum (400 MHz):

2.42 to 2.53 (m partially masked, 2 H); 3.01 to 3.13 (m, 4 H); 3.22 to 3.39 (m partially masked, 1 H); 3.41 to 3.46 (m, 4 H); 4.37 (m, 1 H); 5.03 (s, 1 H); 5.05 (m, 1 H); 7.62 (d, J=8.6 Hz, 2 H); 7.81 (d, J=8.6 Hz, 2 H)

Mass spectrometry: Method A

Retention time Tr (min)=0.98

[M+H]+: m/z 449.

EXAMPLE 38

(8S)-9-[(1R or 1S)-1-(2-fluorophenyl)ethyl]-2-(morpholin-4-yl)-8-(trifluoromethyl)-6,7,8,9-tetrahydro-4 H-pyrimido[1,2-a]pyrimidin-4-one Stage c:

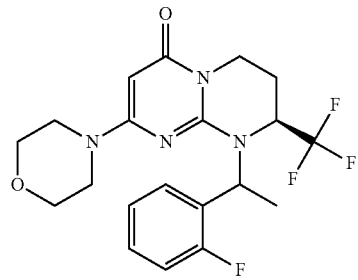 [SMILES: CC(c1ccccc1F)N1c2nc(N3CCOCC3)cc(=O)n2CC[C@H]1C(F)(F)F]

The two diastereoisomers of (8S)-9-[(1R and 1S)-1-(2-fluorophenyl)-ethyl]-2-(morpholin-4-yl)-8-(trifluoromethyl)-6,7,8,9-tetrahydro-4 H-pyrimido-[1,2-a]pyrimidin-4-one are separated by chiral chromatography (Chiralpak AD 20 µm column; elution: 80% heptane 10% EtOH 10% MeOH) using 70 mg of a 70/30 mixture of the two diastereoisomers.

41.5 mg of (8S)-9-[(1R or 1S)-1-(2-fluorophenyl)ethyl]-2-(morpholin-4-yl)-8-(trifluoromethyl)-6,7,8,9-tetrahydro-4 H-pyrimido[1,2-a]pyrimidin-4-one are thus obtained, the characteristics of which are the following:

$^1$ H NMR spectrum (400 MHz):

1.62 (d, J=7.2 Hz, 3 H); 1.68 to 1.85 (m, 1 H); 2.30 to 2.39 (m, 1 H); 3.20 to 3.42 (m, 5 H); 3.50 to 3.65 (m, 4 H); 4.03 (m, 1 H); 4.22 to 4.36 (m, 1H); 4.99 (s, 1 H); 6.05 (q, J=7.2 Hz, 1 H); 7.14 to 7.29 (m, 2 H); 7.35 to 7.43 (m, 1 H); 7.47 (m, 1 H)

Mass spectrometry: method B

Retention time Tr (min)=4.02

[M+H]+: m/z 427

Optical rotation: OR=+33; C=2.543 mg/ml DMSO.

Stage b: (8S)-9-[(1R and 1S)-1-(2-fluorophenyl)ethyl]-2-(morpholin-4-yl)-8-(trifluoromethyl)-6,7,8,9-tetrahydro-4 H-pyrimido[1,2-a]pyrimidin-4-one

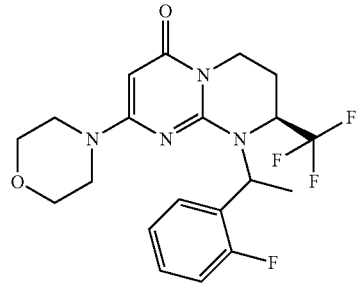 [SMILES: CC(c1ccccc1F)N1c2nc(N3CCOCC3)cc(=O)n2CC[C@H]1C(F)(F)F]

The product can be prepared according to the procedure described in Example 17, but using 500 mg of (8S)-2-(morpholin-4-yl)-8-(trifluoromethyl)-6,7,8,9-tetrahydro-4 H-pyrimido[1,2-a]pyrimidin-4-one, 1 g of caesium carbonate and 391 mg of 1-(1-chloroethyl)-2-fluorobenzene (see stage a below) in 22 ml of acetonitrile. After silica column purification (eluent: CH$_2$Cl$_2$/MeOH 97/03), 70 mg of a 70/30 mixture of the two diastereoisomers of (8S)-9-[(1R and 1S)-1-(2-fluorophenyl)ethyl]-2-(morpholin-4-yl)-8-(trifluoro-methyl)-6,7,8,9-tetrahydro-4 H-pyrimido[1,2-a]pyrimidin-4-one are obtained in the form of a pale yellow powder, the characteristics of which are the following:

Retention time Tr (min)=0.93 and 0.90: 70%–30% mixture of isomers;

[M+H]+: m/z 427.

Stage a: 1-(1-chloroethyl)-2-fluorobenzene

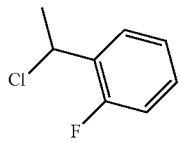

767 mg of thionyl chloride are added to a solution of 1 g of commercial 1-(2-fluorophenyl)ethanol in 20 ml of chloroform. After stirring overnight at a temperature in the region of 20° C., the reaction mixture is washed with a saturated aqueous solution of sodium bicarbonate and then dried over anhydrous magnesium sulphate, filtered and concentrated to dryness under reduced pressure. 780 mg of 1-(1-chloroethyl)-2-fluorobenzene are thus obtained, said product being used as it is in the next stage.

EXAMPLE 39

(8S)-9-[(1R or 1S)-1-(2-fluorophenyl)ethyl]-2-(morpholin-4-yl)-8-(trifluoromethyl)-6,7,8,9-tetrahydro-4 H-pyrimido[1,2-a]pyrimidin-4-one

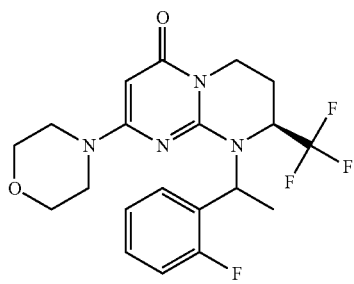 [SMILES: CC(c1ccccc1F)N1c2nc(N3CCOCC3)cc(=O)n2CC[C@H]1C(F)(F)F]

The previous purification (Example 38, stage c) also results in 17.9 mg of (8S)-9-[(1R or 1S)-1-(2-fluorophenyl)ethyl]-2-(morpholin-4-yl)-8-(trifluoro-methyl)-6,7,8,9-tetrahydro-4 H-pyrimido[1,2-a]pyrimidin-4-one, in the form of an amber solid, the characteristics of which are the following:

[1] H NMR spectrum (400 MHz):

1.69 (d, J=7.0 Hz, 3 H); 1.97 to 2.12 (m, 1 H); 2.36 to 2.46 (m, 1 H); 3.15 to 3.35 (m partially masked, 5 H); 3.43 to 3.59 (m, 4 H); 4.09 (m, 1 H); 4.72 (m, 1 H); 4.93 (s, 1 H); 5.73 (q, J=7.0 Hz, 1 H); 7.07 to 7.25 (m, 2 H); 7.28 to 7.40 (m, 1 H); 7.51 (m, 1 H)

Mass spectrometry: method B

Retention time Tr (min)=3.93

[M+H]+: m/z 427

Optical rotation: OR=−96.3+/−1.4; C=2.812 mg/0.5 ml DMSO.

EXAMPLE 40

(8S)-9-[2-(3-fluorophenyl)ethyl]-2-(morpholin-4-yl)-8-(trifluoromethyl)-6,7,8,9-tetrahydro-4 H-pyrimido[1,2-a]pyrimidin-4-one

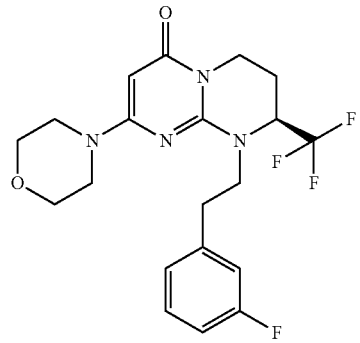 [SMILES: O=c1cc(N2CCOCC2)nc2n1CC[C@@H](C(F)(F)F)N2CCc1cccc(F)c1]

296 mg of sodium hydroxide in 2.5 ml of water, 33 mg of tetrabutylammonium hydrogen sulphate and 200 mg of 1-(2-bromoethyl)-3-fluorobenzene are added to a solution of 150 mg of (8S)-2-(morpholin-4-yl)-8-(trifluoromethyl)-6,7,8,9-tetrahydro-4 H-pyrimido[1,2-a]pyrimidin-4-one in 2.5 ml of toluene. After one hour under microwave irradiation (power 100 watts on a CEM discover apparatus) at 60° C. and then one hour again at 60° C. and twice six hours at 70° C., the reaction mixture is diluted with ethyl acetate. The resulting mixture is washed with water. The organic phase is separated and then concentrated to dryness under reduced pressure. After purification of the resulting residue by preparative HPLC/MS (method D), 43 mg of (8S)-9-[2-(3-fluorophenyl) ethyl]-2-(morpholin-4-yl)-8-(trifluoromethyl)-6,7,8,9-tetrahydro-4 H-pyrimido[1,2-a]pyrimidin-4-one are obtained, the characteristics of which are the following:

[1] H NMR spectrum (400 MHz):

1.87 to 2.05 (m, 1 H); 2.29 to 2.38 (m, 1 H); 2.82 to 3.24 (m, 3 H); 3.38 to 3.50 (m, 5 H); 3.60 to 3.66 (m, 4 H); 4.11 to 4.25 (m, 2 H); 4.50 to 4.69 (m, 1 H); 4.99 (s, 1 H); 6.96 to 7.15 (m, 3 H); 7.28 to 7.41 (m, 1 H)

Mass spectrometry: method B

Retention time Tr (min)=4.10

[M+H]+: m/z 427.

EXAMPLE 41

(8S)-9-benzyl-3-fluoro-2-(morpholin-4-yl)-8-(trifluoro-methyl)-6,7,8,9-tetrahydro-4 H-pyrimido[1,2-a]pyrimidin-4-one Chiral

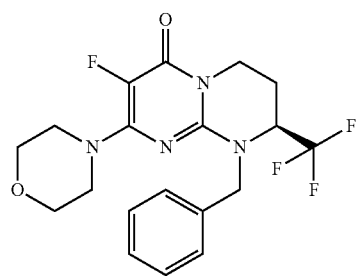

Stage e:

4 g of caesium carbonate and 796 mg of benzyl bromide are added to a suspension of 1 g of (8S)-3-fluoro-2-(morpholin-4-yl)-8-(trifluoromethyl)-6,7,8,9-tetrahydro-4 H-pyrimido[1,2-a]pyrimidin-4-one in 11.8 ml of acetonitrile. After stirring overnight at a temperature in the region of 20° C., the suspension obtained is filtered and the resulting filtrate is concentrated to dryness under reduced pressure. The oily yellow residue is purified on a silica column (eluent: CH$_2$Cl$_2$/MeOH 98/02). The fractions of interest are combined and concentrated to dryness under reduced pressure. The residue is taken up with diethyl ether, spin-filter-dried and then dried under vacuum. 600 mg of (8S)-9-benzyl-3-fluoro-2-(morpholin-4-yl)-8-(trifluoromethyl)-6,7,8,9-tetra-hydro-4 H-pyrimido[1,2-a]pyrimidin-4-one are thus obtained in the form of a white powder, the characteristics of which are the following:

$^1$ H NMR spectrum (400 MHz):
2.17 to 2.30 (m, 1 H); 2.39 to 2.46 (m, 1 H); 3.31 to 3.52 (m, 9 H); 4.23 (m, 1 H); 4.55 (d, J=16.1 Hz, 1 H); 4.61 to 4.73 (m, 1 H); 5.13 (d, J=16.1 Hz, 1 H); 7.20 to 7.26 (m, 3 H); 7.28 to 7.36 (m, 2 H)

Mass spectrometry: method B
Retention time Tr (min)=4.01
[M+H]+: m/z 413.

Stage d: (8S)-3-fluoro-2-(morpholin-4-yl)-8-(trifluoromethyl)-6,7,8,9-tetra-hydro-4 H-pyrimido[1,2-a]pyrimidin-4-one

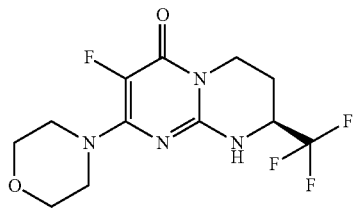 [SMILES: O=c1c(F)c(N2CCOCC2)nc2n1CC[C@@H](C(F)(F)F)N2]

The product can be prepared according to the procedure described in Example 16, stage b, but using 1 g of (8S)-2-chloro-3-fluoro-8-(trifluoromethyl)-6,7,8,9-tetrahydro-4 H-pyrimido[1,2-a]pyrimidin-4-one in 5 ml of acetonitrile, and 1.6 ml of morpholine. After a period overnight at 65° C., 1.1 g of (8S)-3-fluoro-2-(morpholin-4-yl)-8-(trifluoromethyl)-6,7,8,9-tetrahydro-4 H-pyrimido[1,2-a]pyrimidin-4-one are obtained in the form of a beige powder, the characteristics of which are the following:

Mass spectrometry: Method A
Retention time Tr (min)=0.56
[M+H]+: m/z 323; [M−H]−: m/z 321.

Stage c (8S)-3-fluoro-2-chloro-8-(trifluoromethyl)-6,7,8,9-tetrahydro-4 H-pyrimido[1,2-a]pyrimidin-4-one

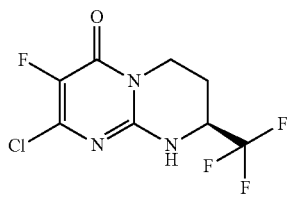 [SMILES: O=c1c(F)c(Cl)nc2n1CC[C@@H](C(F)(F)F)N2]

The enantiomers of (8R,8S)-2-chloro-3-fluoro-8-(trifluoromethyl)-6,7,8,9-tetrahydro-4 H-pyrimido[1,2-a]pyrimidin-4-one are separated by chiral chromatography (Chiralpak AD 20 µm 80×350 mm 250 ml/min 254 nm; 5% EtOH 5% MeOH 90% heptane+0.1% TEA), using 6.8 g of a racemic mixture.

The dextrorotary enantiomer is concentrated so as to obtain 3.13 g of (8S)-2-chloro-3-fluoro-8-(trifluoromethyl)-6,7,8,9-tetrahydro-4 H-pyrimido[1,2-a]pyrimidin-4-one, in the form of a white solid, the characteristics of which are the following:

Mass spectrometry: Method A
Retention time Tr (min)=0.62
[M+H]+: m/z 272; [M−H]−: m/z 270
Optical rotation: OR=+19.6+/−0.6; C=2.488 mg/0.5 ml CH$_3$OH.

Stage b (8R,8S)-2-chloro-3-fluoro-8-(trifluoromethyl)-6,7,8,9-tetrahydro-4 H-pyrimido[1,2-a]pyrimidin-4-one

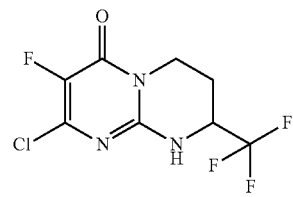 [SMILES: O=c1c(F)c(Cl)nc2n1CCC(C(F)(F)F)N2]

8 ml of phosphorus trichloride are added to a solution of 6.5 g of (8R,8S)-3-fluoro-2-hydroxy-8-(trifluoromethyl)-6,7,8,9-tetrahydro-4 H-pyrimido[1,2-a]pyrimidin-4-one in 20 ml of 1,2-dichloroethane. After stirring for 4 hours at a temperature of 65° C. and a return to a temperature in the region of 20° C., the reaction mixture is concentrated to dryness under reduced pressure. The residue is diluted in 150 ml of ethyl acetate and 10 ml of ice-cold water. A concentrated sodium hydroxide solution is added, at a temperature of between 0° C. and 10° C., until a pH of between 6 and 7 is obtained. The solid formed is filtered off so as to give 3.5 g of a beige solid S1. The filtrate is separated by settling out, and the organic phase is dried over anhydrous magnesium sulphate, filtered and concentrated to dryness under reduced pressure. After silica column purification of the residue (eluent:CH$_2$Cl$_2$/MeOH 97/03), 3.3 g of a pale yellow solid S2 are obtained. The two solids S1 and S2 are combined so as to give 6.8 g of (8R,8S)-2-chloro-3-fluoro-8-(trifluoromethyl)-6,7,8,9-tetrahydro-4 H-pyrimido[1,2-a]pyrimidin-4-one, in the form of a pale yellow powder, the characteristics of which are the following:

Mass spectrometry: Method B
Retention time Tr (min)=2.90
[M+H]+: m/z 272; [M−H]−: m/z 270.

Stage a (8R,8S)-3-fluoro-2-hydroxy-8-(trifluoromethyl)-6,7,8,9-tetra-hydro-4 H-pyrimido[1,2-a]pyrimidin-4-one

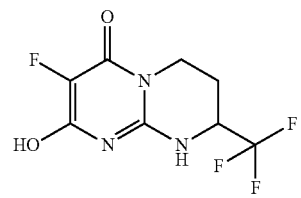 [SMILES: O=c1c(F)c(O)nc2n1CCC(C(F)(F)F)N2]

5.6 g of sodium methoxide are added to a suspension of 7 g of 6-(trifluoromethyl)-1,4,5,6-tetrahydropyrimidin-2-amine hydrochloride (Example 1, stage a) in 35 ml of dimethyl fluoropropanedioate. After the suspension has been stirred for 3 hours at a temperature of 100° C., the medium obtained is concentrated to dryness under reduced pressure. The residue is taken up in diethyl ether and then spin-filter-dried under vacuum. The solid obtained is taken up in 14 ml of water and the resulting mixture is cooled in ice before acidification to pH 5-6 through the addition of concentrated hydrochloric acid (25%). After stirring for 2 hours at a temperature of 0° C. and then overnight at a temperature in the region of 20° C., the suspension is filtered and then the solid is spin-filter-dried and vacuum-dried over $P_2O_5$. 6.5 g of (8R,8S)-3-fluoro-2-hydroxy-8-(trifluoromethyl)-6,7,8,9-tetrahydro-4 H-pyrimido[1,2-a]pyrimidin-4-one are obtained in the form of a yellow powder, the characteristics of which are the following:

Mass spectrometry: Method A

Retention time Tr (min)=0.28

[M+H]+: m/z 254; [M−H]−: m/z 252.

EXAMPLE 42

(8S)-9-(3,5-difluorophenyl)-2-(morpholin-4-yl)-8-(trifluoro-methyl)-6,7,8,9-tetrahydro-4 H-pyrimido[1,2-a]pyrimidin-4-one

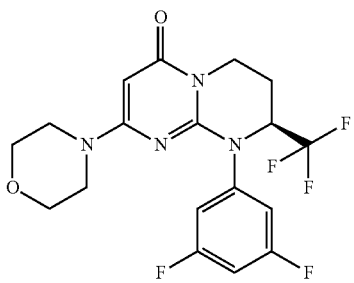

The product is prepared according to the procedure described in Example 12, but using 250 mg of (8S)-2-morpholin-4-yl-8-trifluoromethyl-6,7,8,9-tetrahydropyrimido[1,2-a]pyrimidin-4-one (Example 1e), 276 mg of 1,3-difluoro-5-iodobenzene, 349 mg of tripotassium phosphate, 156 mg of copper iodide and 93 mg of (1S,2S)-cyclohexane-1,2-diamine. After 1 hour at 150° C. under microwave irradiation and silica column purification of the reaction mixture (elution gradient of $CH_2Cl_2$ to $CH_2Cl_2$/MeOH 98/02), 91 mg of (8S)-9-(3,5-difluorophenyl)-2-(morpholin-4-yl)-8-(trifluoromethyl)-6,7,8,9-tetra-hydro-4 H-pyrimido[1,2-a]pyrimidin-4-one are obtained in the form of an ochre foam, the characteristics of which are the following:

$^1$ H NMR spectrum (400 MHz):

2.45 (m, 2 H); 3.07 to 3.16 (m, 4 H); 3.32 to 3.37 (m, 1 H); 3.45 to 3.55 (m, 4 H); 4.36 (m, 1 H); 5.01 (m, 1 H); 5.04 (s, 1 H); 7.18 to 7.34 (m, 3 H)

Mass spectrometry: method A

Retention time Tr (min)=0.95

[M+H]+: m/z 417; [M−H+ $HCO_2$ H]−: m/z 461.

EXAMPLE 43

(8S)-9-[(2,6-difluorophenyl)carbonyl]-2-(morpholin-4-yl)-8-(trifluoromethyl)-6,7,8,9-tetrahydro-4 H-pyrimido[1,2-a]pyrimidin-4-one

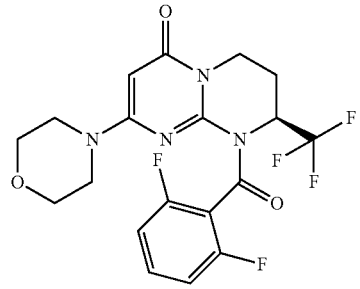 [SMILES: O=C(c1c(F)cccc1F)N1c2nc(N3CCOCC3)cc(=O)n2CC[C@H]1C(F)(F)F]

The product is prepared according to the procedure described in Example 18, using 300 mg of (8S)-2-morpholin-4-yl-8-trifluoromethyl-6,7,8,9-tetrahydropyrimido[1,2-a]pyrimidin-4-one (Example 1e), 47 mg of sodium hydride and 174 mg of 2,6-difluorobenzoyl chloride in 4 ml of tetrahydrofuran. After three successive purifications by silica chromatography (eluent: $CH_2Cl_2$/MeOH; gradient of 100/0 to 98/02 then 98/1 and 98/2), 22 mg of (8S)-9-[(2,6-difluorophenyl)carbonyl]-2-(morpholin-4-yl)-8-(trifluoromethyl)-6,7,8,9-tetrahydro-4 H-pyrimido[1,2-a]pyrimidin-4-one are obtained in the form of a white solid, the characteristics of which are the following:

$^1$ H NMR spectrum (400 MHz):

2.06 to 2.23 (m, 1 H); 2.69 to 2.79 (m, 1 H); 2.91 (m, 2 H); 3.06 (m, 2 H); 3.18 to 3.34 (m partially masked, 1 H); 3.37 to 3.50 (m, 4 H); 4.52 to 4.61 (m, 1 H); 5.23 (s, 1 H); 5.62 to 5.86 (m, 1 H); 7.04 to 7.35 (m, 2 H); 7.50 to 7.67 (m, 1 H)

Mass spectrometry: method A

Retention time Tr (min)=0.93

[M+H]+: m/z 445.

EXAMPLE 44

(8S)-9-[(2,4-difluorophenyl)carbonyl]-2-(morpholin-4-yl)-8-(trifluoromethyl)-6,7,8,9-tetrahydro-4 H-pyrimido[1,2-a]pyrimidin-4-one

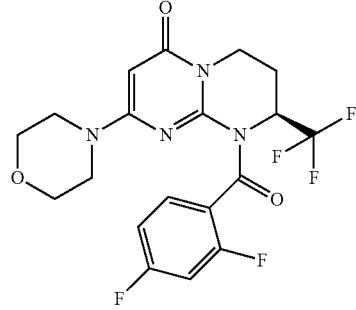 [SMILES: O=C(c1ccc(F)cc1F)N1c2nc(N3CCOCC3)cc(=O)n2CC[C@H]1C(F)(F)F]

The product is prepared according to the procedure described in Example 18, using 300 mg of (8S)-2-morpholin-4-yl-8-trifluoromethyl-6,7,8,9-tetrahydropyrimido[1,2-a]pyrimidin-4-one (Example 1e), 47 mg of sodium hydride and 174 mg of 2,4-difluorobenzoyl chloride in 4 ml of tetrahydrofuran. After two successive purifications by silica chromatography (eluent: $CH_2Cl_2$/MeOH, gradient of 100/0 to 98/02 then 99/01), 24 mg of (8S)-9-[(2,4-difluorophenyl)carbonyl]-2-(morpholin-4-yl)-8-(trifluoromethyl)-6,7,8,9-tetra-hydro-4 H-pyrimido[1,2-a]pyrimidin-4-one are obtained in the form of a colourless lacquer, the characteristics of which are the following:

$^1$ H NMR spectrum (400 MHz):

2.20 (m, 1 H); 2.67 to 2.77 (m, 1 H); 2.81 to 2.91 (m, 2 H); 3.03 (m, 2 H); 3.24 to 3.45 (m partially masked, 2 H); 3.37 to 3.46 (m, 2 H); 3.52 (m, 1 H); 4.30 to 4.48 (m, 1 H); 5.21 (s, 1 H); 5.53 to 5.67 (m, 1 H); 7.18 (dt, J=2.5 and 8.6 Hz, 1 H); 7.35 (ddd, J=2.5 and 9.3 and 11.2 Hz, 1 H); 7.61 to 7.71 (m, 1 H)

Mass spectrometry: method A

Retention time Tr (min)=0.94

[M+H]+: m/z 445.

EXAMPLE 45

(8S)-2-(morpholin-4-yl)-9-(phenylacetyl)-8-(trifluoromethyl)-6,7,8,9-tetrahydro-4 H-pyrimido[1,2-a]pyrimidin-4-one

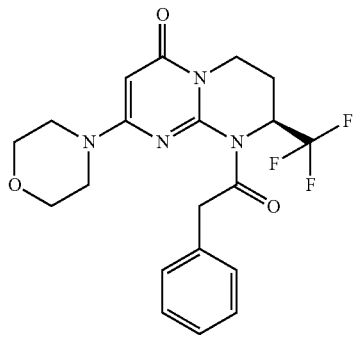 [SMILES: O=C(Cc1ccccc1)N1c2nc(N3CCOCC3)cc(=O)n2CC[C@H]1C(F)(F)F]

The product is prepared according to the procedure described in Example 18, using 300 mg of (8S)-2-morpholin-4-yl-8-trifluoromethyl-6,7,8,9-tetrahydropyrimido[1,2-a]pyrimidin-4-one (Example 1e), 47 mg of sodium hydride and 152 mg of phenylacetyl chloride in 4 ml of tetrahydrofuran. After two successive purifications by silica chromatography (eluent: $CH_2Cl_2$/MeOH; gradient of 100/0 to 98/02 then $CH_2Cl_2$/EtOAc 95/05), 12 mg of (8S)-2-(morpholin-4-yl)-9-(phenylacetyl)-8-(trifluoromethyl)-6,7,8,9-tetrahydro-4 H-pyrimido[1,2-a]pyrimidin-4-one are obtained in the form of a colourless lacquer, the characteristics of which are the following:

$^1$ H NMR spectrum (400 MHz):

1.91 (m, 1 H); 2.59 to 2.69 (m, 1 H); 2.88 (m, 1 H); 3.33 to 3.45 (m, 4 H); 3.60 (m, 4 H); 4.07 (d, J=16.0 Hz, 1 H); 4.16 (d, J=16.0 Hz, 1 H); 4.43 to 4.52 (m, 1 H); 5.30 (s, 1 H); 5.48 to 5.61 (m, 1 H); 7.11 (d, J=7.7 Hz, 2 H); 7.17 to 7.23 (t, J=7.7 Hz, 1 H); 7.28 (t, J=7.7 Hz, 2 H)

Mass spectrometry: method A

Retention time Tr (min)=0.99;

[M+H]+: m/z 423;

[M−H]−: m/z 421; base peak: m/z 303.

EXAMPLE 46

(8S)-9-[2-(3-chlorophenyl)ethyl]-2-(morpholin-4-yl)-8-(trifluoromethyl)-6,7,8,9-tetrahydro-4 H-pyrimido[1,2-a]pyrimidin-4-one

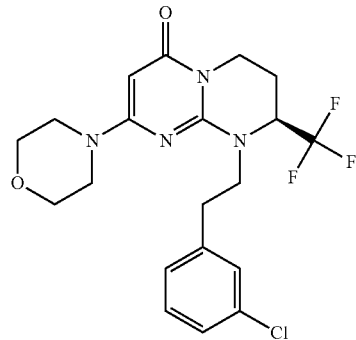 [SMILES: O=c1cc(N2CCOCC2)nc2n1CC[C@@H](C(F)(F)F)N2CCc1cccc(Cl)c1]

The product is prepared according to the procedure described in Example 40, using 150 mg of (8S)-2-(morpholin-4-yl)-8-(trifluoromethyl)-6,7,8,9-tetrahydro-4 H-pyrimido[1,2-a]pyrimidin-4-one in 2.5 ml of toluene are added 296 mg of sodium hydroxide in 2.5 ml of water, 33 mg of tetrabutylammonium hydrogen sulphate and 216 mg of 1-(2-bromoethyl)-3-chlorobenzene. After 44 hours at 60° C. After cooling, the reaction mixture is diluted with ethyl acetate. The organic phase is separated and the aqueous phase is extracted with ethyl acetate. The combined organic phases are concentrated to dryness under reduced pressure and the residue is purified by preparative HPLC/MS (Method D). 42 mg of (8S)-9-[2-(3-chloro-phenyl)ethyl]-2-(morpholin-4-yl)-8-(trifluoromethyl)-6,7,8,9-tetrahydro-4 H-pyrimido[1,2-a]pyrimidin-4-one are thus obtained, the characteristics of which are the following:

$^1$ H NMR spectrum (400 MHz):

1.91 to 2.05 (m, 1 H); 2.34 (m, 1 H); 2.81 to 2.92 (m, 1 H); 2.94 to 3.04 (m, 1 H); 3.17 (m, 1 H); 3.38 to 3.50 (m, 5 H); 3.65 (m, 4 H); 4.09 to 4.22 (m, 2 H); 4.57 to 4.71 (m, 1 H); 4.99 (s, 1 H); 7.17 (d, J=7.8 Hz, 1 H); 7.25 to 7.38 (m, 3 H)

Mass spectrometry: method A

Retention time Tr (min)=1.03

[M+H]+: m/z 443; [M−H+ $HCO_2$ H]−: m/z 487.

EXAMPLE 47

Pharmaceutical Composition

Tablets corresponding to the following formulation were prepared:

Product of Example 1 . . . 0.2 g

Excipient for a tablet having a final weight of . . . 0.1 g (details of the excipient: lactose, talc, starch, magnesium stearate).

Example 1 is taken by way of example of a pharmaceutical preparation, it being possible for this preparation to be carried out, if desired, with other products of formula (I) according to the present invention, and in particular as examples in the present application, among Examples 2 to 46 and 48 to 56.

The products of the table below are products of formula (I) as defined above, and constitute examples 48 to 56 of the present invention. These products from 48 to 56 are prepared as indicated above in the experimental section.

| Example | Name | Mass spectrometry: Method E | |
|---|---|---|---|
| | | Tr (min) | [M + H]+: m/z |
| Example 48 | 9-((R)-2-Benzo[b]thiophen-2-yl-2-hydroxyethyl)-2-morpholin-4-yl-8-(S)-trifluoromethyl-6,7,8,9-tetrahydro-pyrimido[1,2-a]pyrimidin-4-one | 0.83 | m/z 481 |
| Example 49 | 9-[(S)-2-Hydroxy-2-(3-hydroxyphenyl)ethyl]-2-morpholin-4-yl-8-(S)-trifluoromethyl-6,7,8,9-tetrahydropyrimido[1,2-a]pyrimidin-4-one | 0.63 | m/z 441 |
| Example 50 | 2-Dimethylamino-N-{3-[(S)-1-hydroxy-2-((S)-8-morpholin-4-yl-6-oxo-2-trifluoromethyl-3,4-dihydro-2H,6H-pyrimido[1,2-a]pyrimidin-1-yl)ethyl]phenyl}acetamide | 0.51 | m/z 525 |
| Example 51 | 9-[(S)-2-Hydroxy-2-(2-methoxyphenyl)ethyl]-2-morpholin-4-yl-8-(S)-trifluoromethyl-6,7,8,9-tetrahydropyrimido[1,2-a]pyrimidin-4-one | 0.74 | m/z 455 |
| Example 52 | 9-[(S)-2-(4-Fluoro-2-methoxyphenyl)-2-hydroxyethyl]-2-morpholin-4-yl-8-(S)-trifluoromethyl-6,7,8,9-tetrahydro-pyrimido[1,2-a]pyrimidin-4-one | 0.76 | m/z 473 |
| Example 53 | 9-[(S)-2-(4-Chloro-2-methoxyphenyl)-2-hydroxyethyl]-2-morpholin-4-yl-8-(S)-trifluoromethyl-6,7,8,9-tetrahydro-pyrimido[1,2-a]pyrimidin-4-one | 0.81 | m/z 489 |
| Example 54 | 9-[(S)-2-(2-Chloro-4-methoxyphenyl)-2-hydroxyethyl]-2-morpholin-4-yl-8-(S)-trifluoromethyl-6,7,8,9-tetrahydro-pyrimido[1,2-a]pyrimidin-4-one | 0.78 | m/z 489 |
| Example 55 | 9-(2-Hydroxy-3-phenylpropyl)-2-morpholin-4-yl-8-(S)-trifluoromethyl-6,7,8,9-tetrahydropyrimido[1,2-a]pyrimidin-4-one | 0.74 | m/z 439 |
| Example 56 | 9-[2-(4-Hydroxyphenyl)ethyl]-2-morpholin-4-yl-8-(S)-trifluoromethyl-6,7,8,9-tetrahydropyrimido[1,2-a]pyrimidin-4-one | 0.68 | m/z 425 |

Pharmacological Section:
Experimental Protocols
In Vitro Experimental Procedures The inhibitory activity of the molecules on AKT phosphorylation is measured either by western blotting using the technique described below, or by the MSD Multi-spot Biomarker detection technique from Meso Scale Discovery also described below. It was demonstrated, on one set of molecules, that both techniques give compatible results.

Study of pAKT Expression in Pc3Human Prostate Carcinoma Cells Measured by Western Blotting (Test A):

This test is based on measuring the expression of the AKT protein phosphorylated on serine 473. The phosphorylation of AKT (pAKT) is measured by western blotting in the PC3 human prostate carcinoma line (ATCC CRL-1435), using an antibody that specifically recognises pAKT-S473.

On day 1, the PC3 cells are seeded into 6-well plates (TPP, #92006) at the concentration of $0.8 \times 10^6$ cells/well in 1800 µl of DMEM medium (DMEM Gibco #11960-044) containing 10% of foetal calf serum (SVF Gibco, #10500-056) and 1% glutamine (L-Glu Gibco #25030-024), and incubated at 37° C., 5% $CO_2$, overnight.

On day 2, the cells are incubated in the presence or absence of the test products for 1 to 2 hours at 37° C. in the presence of 5% $CO_2$. The molecules, diluted in dimethyl sulphoxide (DMSO Sigma #D2650), are added from a 10-times concentrated stock solution, the final percentage of DMSO being 0.1%. The molecules are tested either at a single concentration of less than or equal to 10 µM, or at increasing concentrations in a range that can extend from less than 1 nM to 10 µM.

After this incubation, the cells are lysed for the preparation of the proteins. After the culture medium has been drawn off, the cells are rinsed with 1 ml of PBS (DPBS Gibco, #14190-094), recovered by scraping in 200 µl of complete HNTG buffer and transferred into a 96-well plate (Greiner #651201), and lysed for 1 h on ice. The HNTG buffer is composed of the following mixture: 50 mM hepes, 150 mM NaCl, 1% triton, 10% glycerol, with extemporaneous addition of one Mini Protease Inhibitor Cocktail tablet (Roche 1836153) and of one Phosphatase Inhibitor Cocktail tablet (Roche104906837001) per 10 ml of buffer.

The lysate is centrifuged for 10 min at 6000 rpm. 155 µl of supernatant are recovered. 150 µl are incubated for denaturation for 5 min at 95° C. in the presence of 4× NuPAGE LDS Sample Buffer diluted 4-fold (InVitrogen ref NP0007) and of 10× NuPAGE Sample Reducing Agent diluted 10-fold (InVitrogen ref NP0009). These samples are then frozen at −20° C. 5 µl are assayed by the microBCA technique according to the technical bulletin of the MicroBCA Protein Assay Kit (Pierce #23235).

For protein separation, 20 µg of proteins are loaded on to a NU-PAGE 4-12% Bis Tris Gel, 12 well (InVitrogen ref NP0322BOX) and the migration is carried out for 1 h 30 in 20×NU-PAGE MOPS SDS Running Buffer diluted 20-fold (InVitrogen ref NP0001), at 150 volts.

The gel is then transferred on to an Invitrolon PVDF membrane (Invitrogen #LC2007) permeabilised beforehand for a few seconds in ethanol (Ethanol Fischer Scientific #E/0600DF/15).

The transfer is carried out in a Biorad tank at 30 volts overnight or at 60 volts for 3 hours, in the presence of 20× NUPAGE Transfer Buffer diluted 20-fold (InVitrogen ref NP0006).

The membrane is then saturated in saturating solution composed of TBS (10× Tris Buffered Saline, Sigma #T5912, diluted 10-fold), 0.1% Tween 20 (Sigma #P5927) and 3% BSA (Bovine Serum Albumin Fraction V, Sigma #A4503) for 6 h after overnight transfer or else for 1 h after transfer for a period of 3 h.

The primary antibodies are diluted to 1/1000th for the anti-phospho AKT-Ser473 antibody (193H2, rabbit monoclonal, cat#4058 from Cell Signaling Technology) Abcam), in saturating solution composed of PBS, 0.1% Tween 20 and 3% BSA, and then shaken overnight at 4° C.

Two rinses for 5 min in washing solution composed of TBS and 0.1% Tween 20 are carried out before hybridisation of the secondary antibodies.

The secondary antibodies are diluted to 1/10000th for the rabbit anti-Mouse IgG HRP antibody (W402 Promega) and to 1/10000th for the goat anti-Rabbit IgG HRP antibody (W401 Promega) in saturating solution, and then shaken for 1 h at ambient temperature.

Two rinses for 30 min in washing solution are carried out and then a rinse for 5 min in $H_2O$ is carried out in order to eliminate the remaining Tween 20.

The revealing solution is prepared volume-for-volume according to the technical bulletin of the Western Lightning Chemiluminescence Reagent Plus (Western Lightning Chemiluminescence Reagent Plus Perkin Elmer #NEL104).

The membrane is placed in the revealing solution for 1 min, drained, inserted between two transparent plates and then placed in the measuring device for reading the luminescence and the quantification of the signal. The luminescence is read with the FujiFilm device (Ray Test).

The FUJI device measures the total luminescence signal obtained (AU) for each band selected. It then subtracts the background noise (BG) proportional to the size of the band selected (Area), said background noise being calculated from a specific background noise band, with a view to obtaining the specific signal (AU-BG) for each band. The band obtained in the absence of product and in the presence of 0.1% DMSO is considered to be the 100% signal. The software calculates the % specific activity (Ratio) obtained for each band selected as a function of this 100% signal. The percentage inhibition is calculated for each concentration according to the formula (100%-Ratio).

Two independent experiments make it possible to calculate the mean of the percentages of inhibition obtained at a given concentration for the products tested only at one concentration.

Where appropriate, the activity of the products is translated into approximate IC50, obtained from a dose-response curve of various concentrations tested and representing the dose giving 50% of specific inhibition (absolute $IC_{50}$). Two independent experiments make it possible to calculate the mean of the $IC_{50}$ values.

Study of pAKT Expression in PC3Human Prostate Carcinoma Cells Measured by the MSD Multi-Spot Biomarker Detection Technique from Meso Scale Discovery (Test B):

This test is based on measuring the expression of the AKT protein phosphorylated on serine 473 (P-AKT-S473), in the PC3 human prostate carcinoma line, by means of the technique based on a sandwich immunoassay using the MSD Multi-spot Biomarker Detection kit from Meso Scale Discovery: phospho-Akt (Ser473) whole cell lysate kit (#K151CAD) or phospho-Akt (Ser473)/Total Akt whole cell lysate kit (#K15100D). The primary antibody specific for P-AKT-S473 (Kit #K151CAD) is coated onto an electrode in each well of the 96-well plates of the MSD kit: after the addition of a protein lysate to each well, the signal is visualised by adding a secondary detection antibody labelled with an electrochemiluminescent compound. The procedure followed is that described in the kit.

On day 1, the PC3 cells are seeded into 96-well plates (TPP, #92096) at the concentration of 35 000 cells/well in 200 μl of DMEM medium (DMEM Gibco #11960-044) containing 10% of foetal calf serum (FCS Gibco, #10500-056) and 1% glutamine (L-Glu Gibco #25030-024), and incubated at 37° C., 5% $OO_2$, overnight.

On day 2, the cells are incubated in the presence or absence of the test products for 1 to 2 h at 37° C. in the presence of 5% of $CO_2$. The molecules, diluted in dimethyl sulphoxide (DMSO Sigma #D2650), are added from a 20-times concentrated stock solution, the final percentage of DMSO being 0.1%. The molecules are tested either at a single concentration of less than or equal to 10 μM, or at increasing concentrations in a range that can extend from less than 1 nM to 10 μM.

After this incubation, the cells are lysed for the preparation of the proteins. For this, after the culture medium has been drawn off, 50 μl of complete Tris Lysis Buffer of the MSD kit containing the protease and phosphatase inhibitor solutions are added to the wells and the cells are lysed for 1 h at 4° C. with shaking. At this stage, the plates containing the lysates can be frozen at −20° C. or at −80° C.

The wells of the 96-well plates of the MSD kit are saturated for 1 h at ambient temperature with the blocking solution of the MSD kit. Four washes are carried out with 150 μl of Tris Wash Buffer of the MSD kit. The lysates previously prepared are transferred into the 96-well multi-spot plates of the MSD kit and incubated for 1 h at ambient temperature, with shaking. Four washes are carried out with 150 μl of Tris Wash Buffer of the MSD kit. 25 μl of the MSD sulfo-tag detection antibody solution are added to the wells and incubated for 1 h at ambient temperature, with shaking. Four washes are carried out with 150 μl of Tris Wash Buffer of the MSD kit. 150 μl of Read Buffer of the MSD kit are added to the wells and the plates are read immediately on the S12400 instrument from Meso Scale Discovery.

The instrument measures a signal for each well. Wells without cells and containing the lysis buffer serve to determine the background noise that will be subtracted from all the measurements (min). The wells containing cells in the absence of product and in the presence of 0.1% DMSO are considered to be the 100% signal (max). The percentage inhibition is calculated for each concentration of test product according to the following formula: $(1-((test-min)/(max-min)))\times 100$.

The activity of the product is translated to $IC_{50}$, obtained from a dose-response curve of the various concentrations tested and representing the dose giving 50% specific inhibition (absolute $IC_{50}$). 2 independent experiments make it possible to calculate the mean of the $IC_{50}$ values.

The inhibitory activity of the molecules on autophagy is measured by the translocation of the LC3 protein from the cytoplasm to the autophagosomes. For this, Hela cells were transfected with a vector encoding the chimeric protein GFP-LC3. A Hela clone stably expressing the GFP-LC3 protein was selected. The translocation of the LC3 protein is determined by measuring the number of cells exhibiting LC3 granulations after a metabolic stress, using an iCyte automatic image analysis cytometer (Compucyte).

Study of the Translocation of the LC3 Protein in Hela Human Cells, Measured by Image Analysis Cytometry (Test C):

On day 1, the Hela GFP-LC3 cells are seeded into 96-well plates coated with poly-D-lysine (Greiner, #655946) at the concentration of 15 000 cells/well in 200 μl of DMEM medium (DMEM Gibco #11960-044) containing 10% of foetal calf serum (FCS Gibco, #10500-056) and 1% glutamine (L-Glu Gibco #25030-024), and incubated at 37° C., 5% $CO_2$, overnight.

On day 2, the cells are washed twice with EBSS (Sigma #E3024). The cells are then incubated in EBSS, 10 μM of hydroxychloroquine and test products for 2 h at 37° C. in the presence of 5% $CO_2$. The molecules are diluted in dimethyl sulphoxide (DMSO Sigma #D2650), the final DMSO percentage being 0.1%. The molecules are tested at increasing concentrations in a range that can extend from 10 nM to 1 µM.

After this incubation, the cells are fixed with 4% paraformaldehyde (Sigma #HT501128 4 L) for 10 min. The cells are then washed twice with PBS and then the nuclei are stained with 2 µg/ml of Hoechst 33342 (Invitrogen #H3570). The 96-well plates are then read with the iCyte image analysis cytometer (Compucyte). The analyser quantifies the number of cells exhibiting LC3 granulations. A cell is considered to be positive when it exhibits at least 4 LC3 granulations. The percentage of cells exhibiting more than 4 granulations is calculated relative to the total number of cells.

The activity of the product is translated to $IC_{50}$, obtained from a dose-response curve of the various concentrations tested and representing the dose giving 50% specific inhibition (absolute $IC_{50}$). Two independent experiments make it possible to calculate the mean of the $IC_{50}$ values.

The results obtained for the products as examples in the experimental section are given in the pharmacological results table below:

Pharmacological Results Table 1:

| Example | Test A* | Test B* | Test C* |
|---|---|---|---|
| Example 1 | 15 | | 11 |
| Example 2 | 315 | | 16 |
| Example 3 | 15 | | 20 |
| Example 4 | 265 | | 569 |
| Example 5 | 10 | 1 | 7 |
| Example 6 | | 23 | 310 |
| Example 7 | | 1 | 5 |
| Example 8 | 75 | | 462 |
| Example 9 | 676 | | |
| Example 10 | 357 | | 249 |
| Example 11 | | 46 | 319 |
| Example 12 | 6596 | | 441 |
| Example 13 | | 25 | 632 |
| Example 14 | | 15 | 337 |
| Example 15 | 2715 | 7 | >1000 |
| Example 16 | 41 | | 187 |
| Example 17 | 350 | | 119 |
| Example 18 | 335 | | >1000 |
| Example 19 | | 39 | >1000 |
| Example 20 | 60 | | >1000 |
| Example 21 | | 24 | 157 |
| Example 22 | | 23 | 785 |
| Example 23 | | 24 | 663 |
| Example 24 | | 9 | 103 |
| Example 25 | | 7 | 38 |
| Example 26 | | 18 | 270 |
| Example 27 | | 10 | 363 |
| Example 28 | | 33 | >10000 |
| Example 29 | | 22 | >1000 |
| Example 30 | | 43 | 212 |
| Example 31 | | 150 | 557 |
| Example 32 | | 33 | 780 |
| Example 33 | | 24 | 221 |
| Example 34 | | 22 | 35 |
| Example 35 | | 20 | 650 |
| Example 36 | | 18 | 157 |
| Example 37 | | 18 | 270 |
| Example 38 | | 2 | 167 |
| Example 39 | | 5 | 237 |
| Example 40 | | 3 | 82 |
| Example 41 | | 4 | 192 |
| Example 42 | | 20 | 310 |
| Example 43 | | 16 | 986 |
| Example 44 | | 108 | >1000 |

-continued

| Example | Test A* | Test B* | Test C* |
|---|---|---|---|
| Example 45 | | 14 | >1000 |
| Example 46 | | 4 | 16 |

*Tests A, B and C: $IC_{50}$ (nM)

Antimalarial Activity Test

The antimalarial activity tests are carried out according to the radioactive micromethod of Desjardins (R. E. Desjardins, C. J. Canfield, J. D. Haynes, J. D. Chulay, Antimicrob. Agents Chemother., 1979, 16, 710-718). The assays are carried out in 96-well microplates (Test Plates Ref. 92696, Techno Plastic Products Ag, Zollstrasse 155, CH-8219 Trasadingen). The *P. falciparum* strains are cultured in solutions of RPM! 1640 supplemented with 5% of human serum with a haematocrit at 2% and a blood parasite concentration at 1.5%. For each assay, the parasites are incubated with selected concentrations of drugs for 48 h at 37° C. in a humid atmosphere and at 5% $CO_2$. Artemisinin, artesunate and also chloroquine diphosphate are used as reference molecules. The first dilution of the drug is prepared at 1 mg/ml in dimethyl sulphoxide. The range of successive daughter solution dilutions is also prepared in dimethyl sulphoxide. Each daughter dilution is then diluted to 1/50th in RPMI 1640 supplemented with 5% of human serum, all of the dilutions being carried out at 37° C. These dilutions are then added to the parasites in culture in the microplates. After addition of the drug, the parasites are in culture in RPMI 1640 containing 5% of human serum and 1% of dimethyl sulphoxide. The growth of the parasites is measured by incorporation of tritiated hypoxanthine (added 24 h after the beginning of the exposure to the drug) compared with the incorporation in the absence of drug.

The activity of the product is translated to % inhibition of the growth of *P. falciparum* (highly chloroquine-resistant strain Fcm29-Cameroon) at 1 µM and 0.1 µM in an in vitro test using infected human erythrocytes.

The results obtained for the products as examples in the experimental section are given in pharmacological results Table 2 below:

Pharmacological Results Table 2:

| Example | P. falciparum % Inhibition 1 µM | P. falciparum % Inhibition 0.1 µM |
|---|---|---|
| Example 1 | 99 | 79 |
| Example 4 | 97 | 19 |
| Example 5 | 92 | 97 |
| Example 12 | 59 | / |
| Example 13 | 52 | / |
| Example 24 | 100 | 40 |
| Example 27 | 36 | / |
| Example 48 | 96 | 89 |
| Example 49 | 99 | 81 |
| Example 50 | 99 | 79 |
| Example 51 | 99 | 75 |
| Example 52 | 99 | 75 |
| Example 53 | 99 | 75 |
| Example 54 | 99 | 83 |
| Example 55 | 93 | 81 |
| Example 56 | 99 | 94 |

The invention claimed is:
1. A product of formula (I):

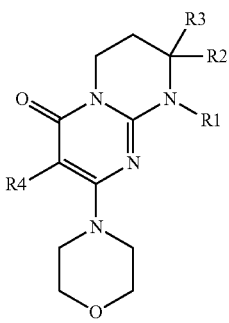

in which:
R1 represents an -L-aryl or -L-heteroaryl radical, such that L represents: either a single bond,
or a linear or branched alkyl radical containing from 1 to 6 carbon atoms and optionally substituted with a hydroxyl radical,
or a CO or —CO-Alkyl-group,
or an L'-X group where L' represents a linear or branched alkyl radical containing from 1 to 6 carbon atoms, and X an oxygen or sulphur atom;
the aryl and heteroaryl radicals being optionally substituted with one or more radicals, which may be identical or different, chosen from halogen atoms and hydroxyl, CN, nitro, —COOH, —COOalkyl, —NRxRy, —CONRxRy, —NRxCORy, —NRxCO₂Rz, —CORy, alkoxy, phenoxy, alkylthio, alkyl, cycloalkyl and heterocycloalkyl radicals;
the alkoxy, phenoxy, alkylthio, alkyl and heterocycloalkyl radicals substituted on the aryl and heteroaryl radicals being themselves optionally substituted with one or more radicals, which may be identical or different, chosen from halogen atoms and NRvRw;
it being possible for the heterocycloalkyl and heteroaryl radicals to additionally contain an oxo radical;
R2 represents a hydrogen atom or an alkyl radical;
R3 represents a hydrogen atom or an alkyl radical optionally substituted with one or more halogen atoms;
R4 represents a hydrogen atom or a halogen atom;
NRxRy being such that Rx represents a hydrogen atom or an alkyl radical and Ry represents a hydrogen atom or a cycloalkyl radical or an alkyl radical optionally substituted with one or more radicals, which may be identical or different, chosen from hydroxyl, alkoxy, NRvRw and heterocycloalkyl radicals; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;
NRvRw being such that Rv represents a hydrogen atom or an alkyl radical and Rw represents a hydrogen atom or a cycloalkyl radical or an alkyl radical optionally substituted with one or more radicals, which may be identical or different, chosen from hydroxyl, alkoxy and heterocycloalkyl radicals; or Rv and Rw form, with the nitrogen atom to which they are attached, a cyclic radical containing from 3 to 10 ring members and optionally one or more other heteroatoms chosen from O, S, NH and N-alkyl, this cyclic radical being optionally substituted;
the cyclic radicals that Rx and Ry or Rv and Rw, respectively, can form with the nitrogen atoms to which they are attached, being optionally substituted with one or more radicals, which may be identical or different, chosen from halogen atoms, and alkyl, hydroxyl, oxo, alkoxy, $NH_2$, NHalkyl and N(alkyl)$_2$ radicals;
Rz represents the values of Ry except for hydrogen;
Rx, Ry and Rz, in the —NRxCORy, —CORy and NRxCO₂Rz radicals, being chosen from the meanings indicated above for Rx, Ry and Rz;
all the above alkyl, alkoxy and alkylthio radicals being linear or branched and containing from 1 to 6 carbon atoms, or
racemic, enantiomeric or diastereoisomeric isomers thereof, or pharmaceutically acceptable salts of said product or racemic, enantiomeric or diastereoisomeric isomers.
2. The product of claim 1, in which:
R1 represents an -L-phenyl or -L-heteroaryl radical, such that L represents:
either a single bond,
or a linear or branched alkyl radical containing from 1 to 6 carbon atoms and optionally substituted with a hydroxyl radical,
or a CO or —CO-Alkyl- group,
or an L'-X group where L' represents a linear or branched alkyl radical containing from 1 to 6 carbon atoms, and X an oxygen or sulphur atom;
the phenyl and heteroaryl radicals being optionally substituted with one or more radicals, which may be identical or different, chosen from halogen atoms and —NRxRy, alkoxy and alkyl radicals;
the alkoxy and alkyl radicals being themselves optionally substituted with one or more radicals chosen from halogen atoms;
R2 represents an alkyl radical;
R3 represents a hydrogen atom or an alkyl radical optionally substituted with one or more halogen atoms;
R4 represents a hydrogen atom or a fluorine atom;
NRxRy being such that Rx represents a hydrogen atom or an alkyl radical and Ry represents a hydrogen atom or an alkyl radical; or Rx and Ry form, with the nitrogen atom to which they are attached, a morpholino radical;
all the above alkyl or alkoxy radicals being linear or branched and containing from 1 to 6 carbon atoms, or racemic, enantiomeric or diastereoisomeric isomers thereof, or pharmaceutically acceptable salts of said product or racemic, enantiomeric or diastereoisomeric isomers.
3. The product of claim 1, corresponding to the following formulae:
-(8S)-9-[2-(4-methoxyphenyl)ethyl]-2-(morpholin-4-yl)-8-(trifluoromethyl)-6,7,8,9-tetrahydro-4H-pyrimido[1,2-a]pyrimidin-4-one
-9-[2-(4-methoxyphenyl)ethyl]-2-(morpholin-4-yl)-8-(trifluoromethyl)-6,7,8,9-tetrahydro-4H-pyrimido [1,2-a]pyrimidin-4-one
-(8S)-2-(morpholin-4-yl)-9-(2-phenylethyl)-8-(trifluoromethyl)-6,7,8,9-tetrahydro-4H-pyrimido [1,2-a]pyrimidin-4-one
-(8S)-9-benzyl-2-(morpholin-4-yl)-8-(trifluoromethyl)-6,7,8,9-tetrahydro-4H-pyrimido[1,2-a]pyrimidin-4-one
-(8S)-9-[(2S)-2-hydroxy-2-phenylethyl]-2-(morpholin-4-yl)-8-(trifluoromethyl)-6,7,8,9-tetrahydro-4H-pyrimido[1,2-a]pyrimidin-4-one

- (8S)-9-[(2R)-2-hydroxy-2-phenylethyl]-2-(morpholin-4-yl)-8-(trifluoromethyl)-6,7,8,9-tetrahydro-4H-pyrimido[1,2-a]pyrimidin-4-one
- (8S)-9-[(2S)-2-hydroxy-2-(4-methoxyphenyl)ethyl]-2-(morpholin-4-yl)-8-(trifluoromethyl)-6,7,8,9-tetrahydro-4H-pyrimido[1,2-a]pyrimidin-4-one
- (8S)-2-(morpholin-4-yl)-9-[(1R)-1-phenylethyl]-8-(trifluoromethyl)-6,7,8,9-tetrahydro-4H-pyrimido [1,2-a]pyrimidin-4-one
- (8S)-9-[1-(4-methoxyphenypethyl]-2-(morpholin-4-yl)-8-(trifluoromethyl)-6,7,8,9-tetrahydro-4H -pyrimido[1,2-a]pyrimidin-4-one
- (8S)-9-[(1S)-1-(4-bromophenyl)ethyl]-2-(morpholin-4-yl)-8-(trifluoromethyl)-6,7,8,9-tetrahydro -4H-pyrimido[1,2-a]pyrimidin-4-one
- (8S)-9-[(1R)-1-(4-bromophenyl)ethyl]-2-(morpholin-4-yl)-8-(trifluoromethyl)-6,7,8,9-tetrahydro -4H-pyrimido[1,2-a]pyrimidin-4-one
- (8S)-2-(morpholin-4-yl)-9-phenyl-8-(trifluoromethyl)-6,7,8,9-tetrahydro-4H-pyrimido[1,2-a]pyrimidin-4-one
- (8S)-9-(4-fluorophenyl)-2-(morpholin-4-yl)-8-(trifluoromethyl)-6,7,8,9-tetrahydro-4H-pyrimido [1,2-a]pyrimidin-4-one
- (8S)-9-(3-fluorophenyl)-2-(morpholin-4-yl)-8-(trifluoromethyl)-6,7,8,9-tetrahydro-4H-pyrimido [1,2-a]pyrimidin-4-one
- (8S)-9-(2-fluorophenyl)-2-(morpholin-4-yl)-8-(trifluoromethyl)-6,7,8,9-tetrahydro-4H-pyrimido [1,2-a]pyrimidin-4-one
- (8S)-9-[(1R)-1-(3-fluorophenyl)ethyl]-2-(morpholin-4-yl)-8-(trifluoromethyl)-6,7,8,9-tetrahydro -4H-pyrimido[1,2-a]pyrimidin-4-one
- (8S)-9-(4-fluorobenzyl)-2-(morpholin-4-yl)-8-(trifluoromethyl)-6,7,8,9-tetrahydro-4H-pyrimido [1,2-a]pyrimidin-4-one
- (8S)-2-(morpholin-4-yl)-9-(phenylcarbonyl)-8-(trifluoromethyl)-6,7,8,9-tetrahydro-4H-pyrimido[1,2-a]pyrimidin-4-one
- (8S)-2-(morpholin-4-yl)-9-(pyridin-3-yl)-8-(trifluoromethyl)-6,7,8,9-tetrahydro-4H-pyrimido [1,2-a]pyrimidin-4-one
- (8S)-2-(morpholin-4-yl)-9-(pyridin-4-yl)-8-(trifluoromethyl)-6,7,8,9-tetrahydro-4H-pyrimido [1,2-a]pyrimidin-4-one
- (8S)-9-(4-methylphenyl)-2-(morpholin-4-yl)-8-(trifluoromethyl)-6,7,8,9-tetrahydro-4H-pyrimido [1,2-a]pyrimidin-4-one
- (8S)-9-(2-chlorobenzyl)-2-(morpholin-4-yl)-8-(trifluoromethyl)-6,7,8,9-tetrahydro-4H-pyrimido [1,2-a]pyrimidin-4-one
- (8S)-9-(3-fluorobenzyl)-2-(morpholin-4-yl)-8-(trifluoromethyl)-6,7,8,9-tetrahydro-4H-pyrimido [1,2-a]pyrimidin-4-one
- (8S)-9-[2-(2-methoxyphenyl)ethyl]-2-(morpholin-4-yl)-8-(trifluoromethyl)-6,7,8,9-tetrahydro-4H -pyrimido[1,2-a]pyrimidin-4-one
- (8S)-9-[2-(3-methoxyphenyl)ethyl]-2-(morpholin-4-yl)-8-(trifluoromethyl)-6,7,8,9-tetrahydro-4H -pyrimido[1,2-a]pyrimidin-4-one
- (8S)-9-(3-methoxybenzyl)-2-(morpholin-4-yl)-8-(trifluoromethyl)-6,7,8,9-tetrahydro-4H-pyrimido [1,2-a]pyrimidin-4-one
- (8S)-9-(4-methoxyphenyl)-2-(morpholin-4-yl)-8-(trifluoromethyl)-6,7,8,9-tetrahydro-4H-pyrimido [1,2-a]pyrimidin-4-one
- (8S)-9-[(2-fluorophenyl)carbonyl]-2-(morpholin-4-yl)-8-(trifluoromethyl)-6,7,8,9-tetrahydro-4H -pyrimido[1,2-a]pyrimidin-4-one
- (8S)-9-(3,5-difluorobenzyl)-2-(morpholin-4-yl)-8-(trifluoromethyl)-6,7,8,9-tetrahydro-4H-pyrimido [1,2-a]pyrimidin-4-one
- (8S)-9-(2,4-difluorobenzyl)-2-(morpholin-4-yl)-8-(trifluoromethyl)-6,7,8,9-tetrahydro-4H-pyrimido [1,2-a]pyrimidin-4-one
- (8S)-2-(morpholin-4-yl)-9-(2,3,4-trifluorobenzyl)-8-(trifluoromethyl)-6,7,8,9-tetrahydro-4H-pyrimido [1,2-a]pyrimidin-4-one
- (8S)-9-[(5-chloro-1-benzothiophen-3-yl)methyl]-2-(morpholin-4-yl)-8-(trifluoromethyl)-6,7,8,9-tetrahydro-4H-pyrimido[1,2-a]pyrimidin-4-one
- (8S)-9-[(1R or 1S)-1-(4-fluorophenyl)ethyl]-2-(morpholin-4-yl)-8-(trifluoromethyl)-6,7,8,9-tetrahydro -4H-pyrimido[1,2-a]pyrimidin-4-one
- (8S)-9-[(1R or 1S)-1-(4-fluorophenyl)ethyl]-2-(morpholin-4-yl)-8-(trifluoromethyl)-6,7,8,9-tetrahydro -4H-pyrimido[1,2-a]pyrimidin-4-one
- (8S)-9-(3-methylphenyl)-2-(morpholin-4-yl)-8-(trifluoromethyl)-6,7,8,9-tetrahydro-4H-pyrimido [1,2-a]pyrimidin-4-one
- (8S)-9-(4-chlorophenyl)-2-(morpholin-4-yl)-8-(trifluoromethyl)-6,7,8,9-tetrahydro-4H-pyrimido [1,2-a]pyrimidin-4-one
- (8S)-2-(morpholin-4-yl)-8-(trifluoromethyl)-9-[4-(trifluoromethyl)phenyl]-6,7,8,9-tetrahydro-4H -pyrimido[1,2-a]pyrimidin-4-one
- (8S)-9-[(1R or 1S)-1-(2-fluorophenyl)ethyl]-2-(morpholin-4-yl)-8-(trifluoromethyl)-6,7,8,9-tetrahydro -4H-pyrimido[1,2-a]pyrimidin-4-one
- (8S)-9-[(1R or 1S)-1-(2-fluorophenyl)ethyl]-2-(morpholin-4-yl)-8-(trifluoromethyl)-6,7,8,9-tetrahydro -4H-pyrimido[1,2-a]pyrimidin-4-one
- (8S)-9-[2-(3-fluorophenyl)ethyl]-2-(morpholin-4-yl)-8-(trifluoromethyl)-6,7,8,9-tetrahydro-4H-pyrimido [1,2-a]pyrimidin-4-one
- (8S)-9-benzyl-3-fluoro-2-(morpholin-4-yl)-8-(trifluoromethyl)-6,7,8,9-tetrahydro-4H-pyrimido [1,2-a]pyrimidin-4-one
- (8S)-9-(3,5-difluorophenyl)-2-(morpholin-4-yl)-8-(trifluoromethyl)-6,7,8,9-tetrahydro-4H-pyrimido [1,2-a]pyrimidin-4-one
- (8S)-9-[(2,6-difluorophenyl)carbonyl]-2-(morpholin-4-yl)-8-(trifluoromethyl)-6,7,8,9-tetrahydro-4H -pyrimido[1,2-a]pyrimidin-4-one
- (8S)-9-[(2,4-difluorophenyl)carbonyl]-2-(morpholin-4-yl)- 8 -(trifluoromethyl)-6,7,8,9-tetrahydro-4H -pyrimido [1 ,2-a]pyrimidin-4-one
- (8 S)-2-(morpholin-4-yl)-9-(phenylacetyl)- 8-(trifluoromethyl)-6,7,8,9-tetrahydro-4H-pyrimido [1,2-a]pyrimidin-4-one
- (8S)-9- [2-(3 -chlorophenypethyl]-2-(morpholin-4-yl)-8-(trifluoromethyl)-6,7,8,9-tetrahydro-4H-pyrimido [1,2-a]pyrimidin-4-one
- 9-((R)-2-benzo [b]thiophen-2-yl-2-hydroxyethyl)-2-morpholin-4-yl-8-(S)-trifluoromethyl-6,7,8,9-tetrahydropyrimido[1,2-a]pyrimidin-4-one
- 9- [(S)-2-hydroxy-2-(3-hydroxyphenyl)ethyl]-2-morpholin-4-yl-8-(S)-trifluoromethyl-6,7,8,9-tetrahydropyrimido [1,2-a]pyrimidin-4-one
- 2-dimethylamino-N-{3 -[(S)-1-hydroxy-2-((S)-8-morpholin-4-yl-6-oxo-2-trifluoromethyl-3,4-dihydro -2H,6H-pyrimido[1,2-a]pyrimidin-1 -yl)ethyl]phenyl}acetamide

- -9-[(S)-2-hydroxy-2-(2-methoxyphenyl)ethyl]-2-morpholin-4-yl-8-(S)-trifluoromethyl-6,7,8,9-tetrahydropyrimido [1,2-a]pyrimidin-4-one
- -9- [(S)-2-(4-fluoro-2-methoxyphenyl)-2-hydroxyethyl]-2-morpholin-4-yl-8 -(S)-trifluoromethyl-6,7,8,9-tetrahydropyrimido [1,2-a]pyrimidin-4-one
- -9-[(S)-2-(4-chloro-2-methoxyphenyl)-2-hydroxyethyl]-2-morpholin-4-yl-8-(S)-trifluoromethyl-6,7,8,9-tetrahydropyrimido [1,2-a]pyrimidin-4-one
- -9-[(S)-2-(2-chloro-4-methoxyphenyl)-2-hydroxyethyl]-2-morpholin-4-yl-8-(S)-trifluoromethyl-6,7,8,9-tetrahydropyrimido[1,2-a]pyrimidin-4-one
- -9-(2-hydroxy-3-phenylpropyl)-2-morpholin-4-yl-8-(S)-trifluoromethyl-6,7,8,9-tetrahydropyrimido [1,2-a]pyrimidin-4-one
- -9-[2-(4-hydroxyphenyl)ethyl]-2-morpholin-4-yl-8-(S)-trifluoromethyl-6,7,8,9-tetrahydropyrimido [1,2-a]pyrimidin-4-one or pharmaceutically acceptable salts thereof.

4. A process for preparing the product according to claim 1, according to scheme 1 as defined hereinafter:

in which the substituents R1, R2, R3 and R4 have the meanings indicated in claim 1 and in which R represents alkyl, and X represents a chlorine, bromine or iodine atom or a sulphonyloxy group such as trifluoromethylsulphonyloxy, Ar is aryl and Het is heteroaryl.

5. A process for preparing the product according to claim 1, according to scheme 2 as defined hereinafter:

Scheme 2:

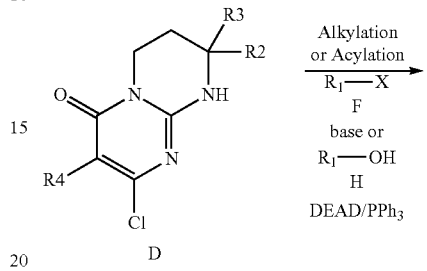

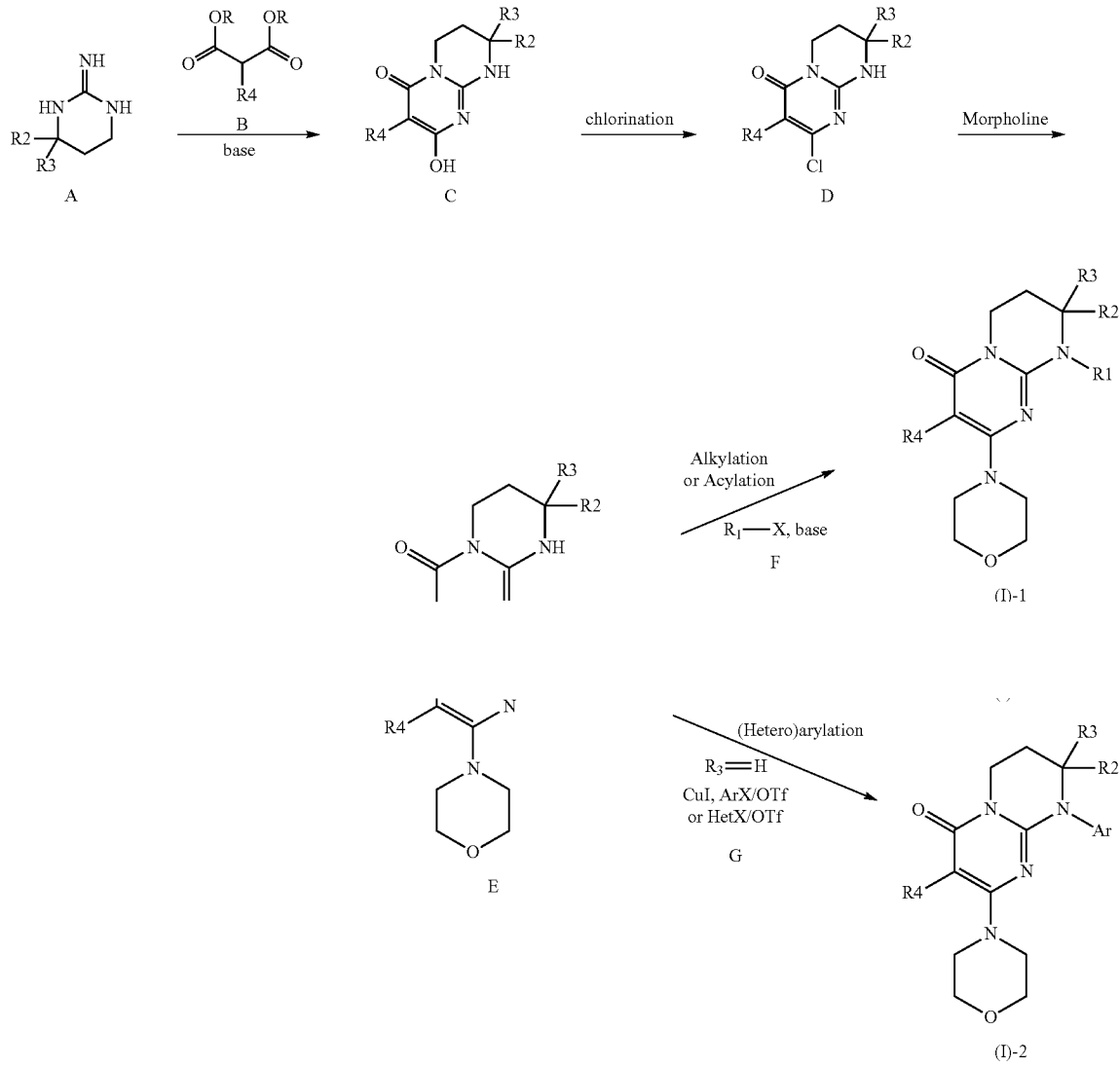

-continued

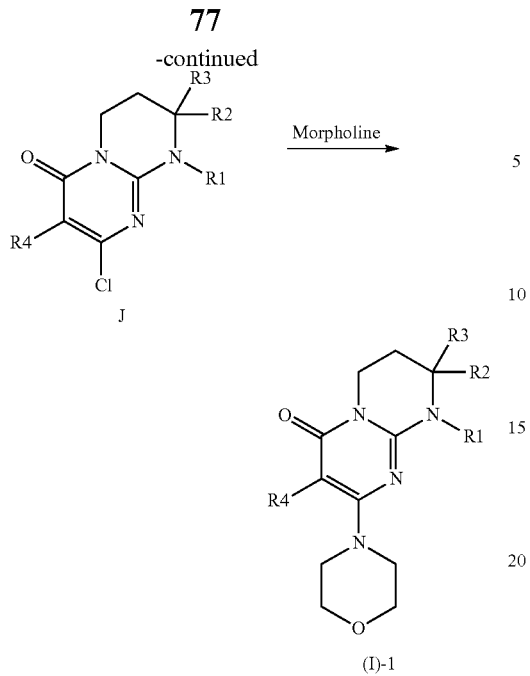

in which the substituents R1, R2, R3 and R4 have the meanings indicated in claim 1, and X represents a chlorine, bromine or iodine atom or a sulphonyloxy group such as trifluoromethylsulphonyloxy.

6. A pharmaceutical composition comprising the product of claim 1 or pharmaceutically acceptable salts thereof.

7. A pharmaceutical composition comprising the product of claim 3, or pharmaceutically acceptable salts thereof.

8. A pharmaceutical composition containing, as active ingredient, at least one product according to claim 1, or a pharmaceutically acceptable salt of said product, and a pharmaceutically acceptable carrier.

9. A method of treating cancers capable of being modulated by inhibition of PI3K/AKT/mTOR pathway in a patient in need thereof comprising administering to said patient a therapeutically effective amount of the product according to claim 1.

10. The method according to claim 9, wherein solid or liquid tumours are treated.

11. The method according to claim 9, wherein said cancers are resistant to cytotoxic agents.

12. The method according to claim 9, comprising treating primary tumours and/or of metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid haematopoietic tumours, in sarcomas, in brain, larynx and lymphatic system cancers, bone and pancreatic cancers, and in hamartomas.

13. The product according to claim 1, wherein said product is an inhibitor of AKT(PKB) phosphorylation.

14. A product having one of the following formulas:

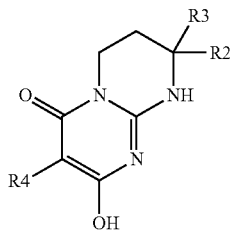

C

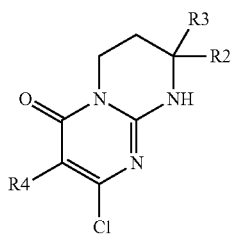

D

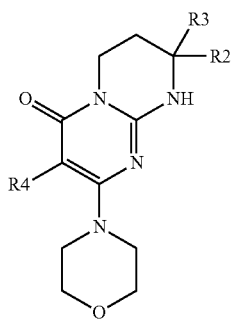

E

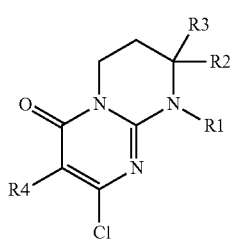

J in which R1, R2, R3 and R4 have the definitions indicated in claim 1.

15. A method of or treating glycogenosis type II or Pompe disease in a patient in need thereof comprising administering to said patient a therapeutically effective amount of the product of claim 1.

16. A method of treating parasitic diseases selected from the group consisting of malaria, sleeping sickness, Chagas disease and leishmaniasis in a patient in need thereof comprising administering to said patient a therapeutically effective amount of the product of claim 1.

17. The method according to claim 16 wherein the parasitic disease is malaria, Chagas disease or leishmaniasis.

* * * * *